United States Patent [19]

Hurwitz et al.

[11] Patent Number: 5,648,243

[45] Date of Patent: Jul. 15, 1997

[54] HUMAN SERUM ALBUMIN EXPRESSION CONSTRUCT

[75] Inventors: David R. Hurwitz, Wyndmoor; Margret Nathan, West Chester, both of Pa.; Moshe Shani, Mobile Post Modyin, Israel

[73] Assignees: Rhone-Poulenc Rorer Pharmaceuticals, Inc., Collegeville, Pa.; Peri Development Applications (1985) Ltd., Israel

[21] Appl. No.: 310,356

[22] Filed: Sep. 21, 1994

Related U.S. Application Data

[63] Continuation of Ser. No. 737,853, Jul. 31, 1991, abandoned.

[51] Int. Cl.$^6$ .............................. C12N 15/14; C12N 15/85
[52] U.S. Cl. ................. 435/69.6; 435/172.3; 435/320.1; 536/23.1; 536/23.5; 536/24.1; 536/24.2
[58] Field of Search ....................... 435/172.1, 172.3, 435/320.1, 69.6, 240.2; 935/10, 36, 35, 53, 63, 93; 800/2, DIG. 1; 536/23.1, 23.5, 24.1, 24.2

*Primary Examiner*—John L. LeGuyader
*Attorney, Agent, or Firm*—Klauber & Jackson

[57] ABSTRACT

The present invention provides DNA constructs comprising a promoter DNA sequence and a DNA sequence coding for human serum albumin. In one embodiment the human serum albumin sequence comprises at least one, but not all, of the introns in the naturally occurring gene encoding for the HSA protein. In another embodiment the DNA constructs comprise a 5' regulatory sequence which directs the expression and secretion of HSA protein in the milk of a transgenic animal. Preferably, the promoter gene is a milk protein promoter sequence such as β-lactoglobulin. The present invention also provides transgenic animals which secrete HSA in the milk of lactating females. The present invention also provides vectors comprising the constructs of the present invention.

19 Claims, 29 Drawing Sheets

FIG. 1B-1

```
CCTTTCCCAGGGACTTCTACACAAGGAAAAAGCTAGAGTTGGTTACTGACTTCTAATAAATGCCTACACAATTTCTAGGAAGTTAAAAGTTGACATAATTTATCCAAGAAAGAATTATTT
CTTAACTTAGAATAGTTCTCTTTTCTTTTCAGATGTAGAGTTTTTCTGGCTTTAGAAAAAAATGCTTGTTTTTCTTCAATGGAAAATAGGCACACTTGTTTTATGTCTGTTCATCTGTAGT
CAGAAAGACAAGTCTGGTATTTCCTTTCAGGACTCCCCTTGAGTCATTAAAAAAAAATCTTCCTATCTATCATCTAGCTTTGATTTTTTCCTCTCTGTGCTTTAT
TAGTTAATTAGTACCCATTTCTGAAGAAGAAATAACATAAGATTATAGAAAATTTCTTCATTGTAAGACTGAATAGAAAAATTTCTTCATTATAAGACTGAGTAGAAAAATA
ATACTTTGTTAGTCTCTGTGCCTATGTGCCATGAGAGGAAATTTGACTACTGGTTTCTCATTGTAAGATAACTGGCTTAGTACTAATTATTGTTCTGTAGTA
TCAGAGAAAGTTGTCTTCCTACTGGTTGAGCTCAGTAGTTCTTCATATTCTGAGCAAAAGGGCAGAGTAGGATAGCTTTTCTGAGGTAGAGATAAGAACCTTGGGTAGGGAAGGAAGA
TTTATGAAATATATTTAAAAAATTATTCCTTGCTTTGTTTTTAGACATAATGTAAATTTAAAGCAACATAAAAGAACATGATTTTCTACTTATTGAAAGAGA
GAAAGGAAAAAAAATATGAAACAGGATGGAAAGAATCCTATGCCTGGTGAAGGTTCTCATAACCTACAGAGAATTTGGGGTCAGCCTGCCTATTGTATATTATGGCAAAGAT
AATCATCATCTCATTTGGGTCCATTTCCTCCTCTCCATCTGCTTAAGTTCCTATCTCTCTTACTTGTTATTTTTGCATTGCTCTATGTCTTTTTCTTAGTTGCATCTGAGGCAACATAGCCTATCTCAGGCTTGAATCACATGTGGGCCAC
AGCAGGAATGGGAACATGGAATTTCTAAGTCCTAAGTATTGTGTGTGTGTGTGTAAGATTAGTTGGTTAGTAATTACTAAACACTGAAACTAAAAATGTTCAAG
TAAAAAGACACAGAAGCCCTAACTCTTCAGTATGATGTCTTATTCTAAGCAAAGTATTTAGTTTGTGTGTAATTACTAAACACTGAAACTAAAAATGTTCAAG
ATGCAAATTTGGGACTTAACATGGTAATAAATACCATGGTAATGAATAAAAGGTACAAATCGTTTAAACTCTTATGTAATTTGATAAGATGTTTTACACAACTTAATCATTGACAAGGTCTTGTGAGA
TGGGAAATTACAGTTAAATTACACAAGGGATTTAGTAGTTACAACAAGGATTTCAAAACAATTTGTCAAGAAGAATATTTGTAATCGGTTGGCAGCCAATGAAATACAAAGATGAGTCTAGTAATA
AACAGTTCCAGATGGTAAATATACACAAGGATTTAGTAGTATATTAGTGCTAAATTCCCTCCGTTGTCCT
                                                          Exon 1 ——(118 bp)
                                                          Cap' Site    -1 Exon 1│Intron
                                                          AGCTTTTCTCTTCTTCTGTCAACCCACACGCCTTTGGCACA GTAAGAAATCCATTTTCTATTGTTCAACTTTTATTCT
       peptide   (pre)              -1 -6 (pro)            -1           -18  Leader
ATCTACAATTATTGGTTAAAGAAGTATATTAGTGCTAAATTCCCTCCGTTGTCCT                  Met lys trp val thr phe
ile ser leu phe leu phe ser ser ala tyr ser Arg gly val phe arg arg Asp ala h│GTAAGAAATCCATTTTCTATTGTTCAACTTTTATTCT
ATT TCC CTT TTT CTC TTT AGC TCC GCT TAT TCG AGG GGT GTG TTT CGT CGA GAT GCA C                      ATG AAG TGG GTA ACC TTT
                                                                                   ——(709 bp)——
```

FIG. 1B-2

```
ATTTCCCAGTAAAATAAAGTTTTAGTAACTCTGCATCTTTAAAGAATTATTTGTCATTTATTTCTAAAATGGCATAGTATTTGTATTTGTGAAGTCTTACAAGGTTATCTTATTAA
TAAAATTCAAACATCCTAGGTAAAAAAAAAAGGTCAGATTTGTTTAGTGACTGTAATTTCTTTTGCGCACTAAGGAAAGTGCAAAGTAACTTAGAGTGACTGAAACTTCACAGAAT
AGGGTGAAGATTGAATTCATAACTATCCCAAAGACCTATCCATTGCACTATGCTTTATTTAAAAACCACAAACCTGTGCTGTTGATCTCATAAATAGAACTTGTATTTATATTATTT
TCATTTTAGTCTGTCTTCTTGGTTGCTGTGTTGATAGACATTAAAAGAGTATTAGATATTATCTAAGTTTGAATATATTTAATATTTTAAAATAGTATTCTTGGTAAT
TGAATTATTCTTCTGTTAAAGGCAGAAGAATAATTGAACATCATCCTGAGTTTTTCTGTAGGAATCAGAGCCCAATATTTGAAACAAATGCATAATCTAAGTCAAATGGAAAGAAAT

-----Intron1|Exon2-----(58 bp)
                                   |is lys ser glu val ala his arg phe lys asp leu
ATAAAAGTAACATTATACTTCTGTTTCTTCAGTATTTAACAATCCTTTTTTTCTTCCCTTGCCCAG|AC AAG AGT GAG GTT GCT CAT CGG TTT AAA GAT TTG -----Exon2|Intron2-----(1,454 bp)
gly glu asn phe lys ala le|
GGA GAA AAT TTC AAA GCC TT|GTAAGTTAAAACAGTGCTGCCTGTAGAGTTTCTGCGTTGAGGAAGATATTCTGAGGAAGTAAAATATTGATGAATCAAATTTAATGTTTCTAATAGTGTTGTTATTATTCTAAAGTGCTTATATTCCTTGTCATCAGGGT
TCAGATTCTAAAACAGTGCTGCCTGTAGAGTTTCTGCGTTGAGGAAGATATTCTGAGGAAGTAAAATATTGATGAATCAAATTTAATGTTTCTAATAGTGTTGTTATTATTCTAAAGTGCTTATATTCCTTGTCATCAGGGT
AGTGCAACTGAGAAACAAAAACTTAAAATGTATTTGTAGTTAATTGCACATGTATATAGTCACATGTTAGTATTGGACAGTACAGCTCTGGAACTTGCTTGGTGG
AAAGGACTTTAATATAGGTTTCCTTTGGTGCAGTGGCAGTCTCGGGCTTCACGCCATTCTCCTGCGCAAACTCCGCTCCCGGGTTCACGCCATTCTCCTGCGCAAACTCCGCTCCCGGGTTCACGCCATTCTCCTGCGCAAACTCCGCTCCCGGGAATATTTAAT|TTTTTTTTTTAAGACAGGGTCTCG
                                                                                                                                                    ******
CTCTGTGCCCAGGCTGGAGTGCAGTGGCGCAATCTCGGCTCACTGCAAACTCCGCTCCCGGGTTCACGCCATTCTCCTGCCTCAGCCTCCCGAGTAGCTGGGACTACAGGCGCCCGCCA
<--------Alu 1
TCACGCCCGGCTAATCTTTGTATTTTTAGTAGAGATGGGGTTTCACCGTGTGCCAGGATGGTCTCAATCTCCTGACATCGTGATCTGCCCACCTCGGCCTCCCAAAGTGCTGGGATTAC      Alu 2-------->
                                                                                                                        AGGAGTGAGTCACCGCCGGCCCGGCTATTTGTATTTTAAATGTTTTTTAATCTAGTAAAAATGAGAAATTGTTTTTTAAAAGTCTACCTAATCCTACAGGCTAATTAAAGACGTGTGTGGGGATC
******                                                                                                                  *******
AGGTGCGGTGGTTCACACCTGTAATCCCAGCACTTTGGAAGGCTGAGGCTGATGCAGGAGGATTGCTTGAGCCCAGGAGTACAGACCAGGCCTGGGCAAGTCTCTTTAAAAAACAAACAAACA
```

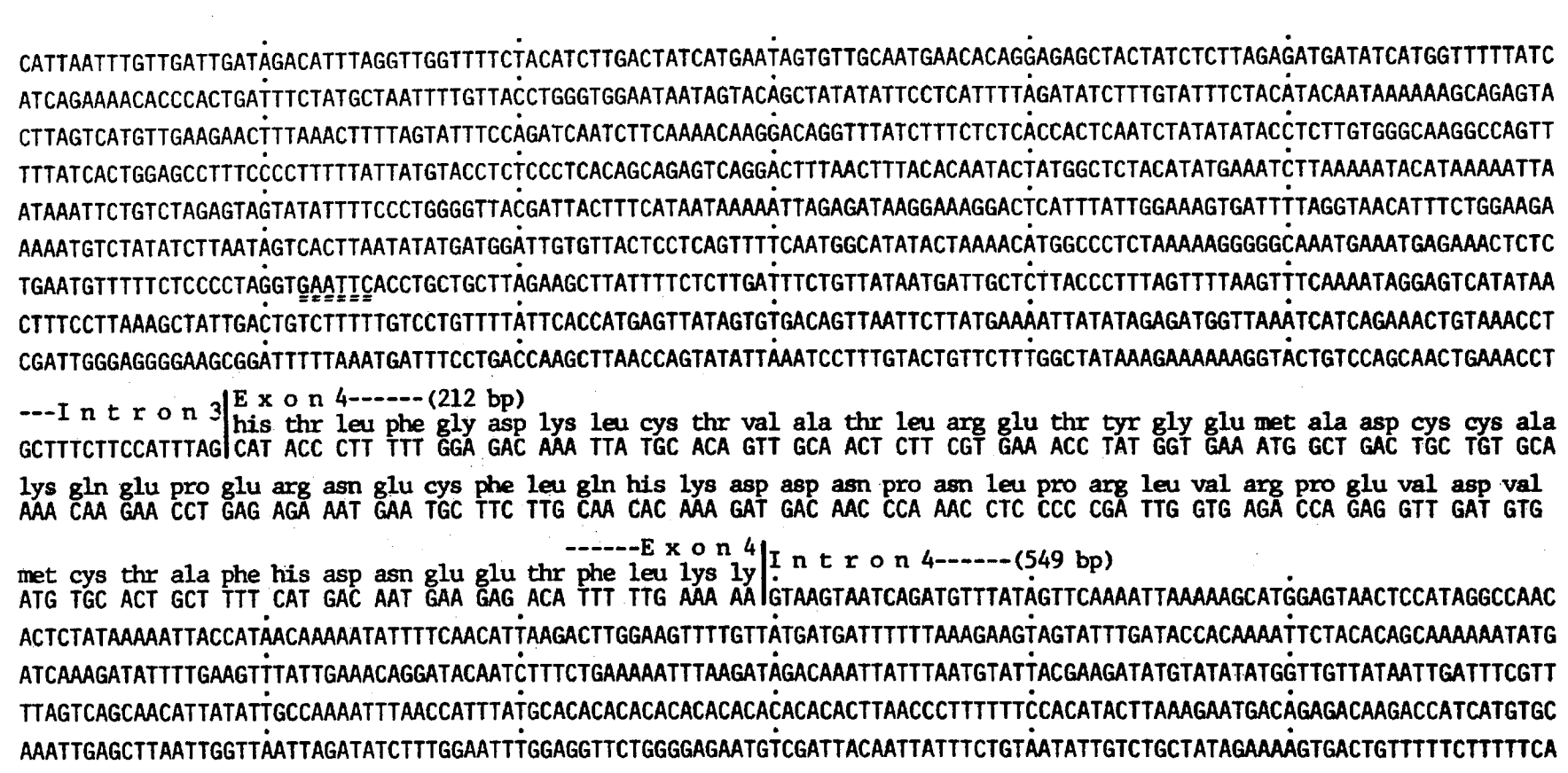

```
Intron 4|Exon 5-----(133 bp)
        |s tyr leu tyr glu ile ala arg arg his pro tyr phe ala pro glu leu leu phe ala lys arg tyr lys ala ala
AAATTTAG|A TAC TTA TAT GAA ATT GCC AGA AGA CAT CCT TAC TTT TAT GCC CCG GAA CTC CTT TTT GCT AAA AGG TAT AAA GCT GCT -----Exon 5-----(824 bp)
phe thr glu cys gln ala ala asp lys ala cys leu leu pro lys|Intron 5-----(824 bp)
TTT ACA GAA TGT CAA GCT GCT GAT AAA GCT TGC CTG TTG CCA AAG|GTATTATGCAAAAGAATAGAAAAAAGAGTTCATTATCCAACCTGATTTTGT
CCATTTTGTGGCTAGATTAGGGAACCTGAGTGTCTGATACAAACTTTCCGACACATGGTCAAAAAGCCTTCATCTTTGAAAATCTTTGTCTTGAAAATCTTTCATCACTCTCGT
TTCTCTTTTAAGATTTGCCAATGATGATCTGTCAGAGGTAATCACTGTGCATGTGTTAAAGATTTCACCACTTTTATGGTGGTGATCACTATAGTGAAATACTGAAACTTGTTGTC
AAATTGCACAGCAAGGGGACACAGTTCTTTATTCTTTTCATGATAATTTTAGTAGGAGGGAATTCAAAGTAGTGCATCTAGATGCCTGAGTTCATGCATTCATTCC
ATAAATATATATTAGGAATGCTTATTCTTTTCTGAGAGTTGGTGGTGAGGAGACTGAAATGAATTATACACAAAATTTAAAAATTAAGCAGCCCCTGG
GATATTAGCGTACTCTTTCTCTGACTTTCTCCCACTTTTCTTAGGCTCTTTAAGGCTAAGGGAGTACTTGGGAATTTAGGCATAAATATGCCTTCAAAATTTAATTTGGCACAGTCTCATCTGAGCTTATGGAGGGGT
TCTTTCCTTTTCTAGAGAGCTACTCTTTCTGAGAGGCAAAATCATTATTCGCTAAGGGAGTACTTGGGAATTTAGGCATAAATATGCCTTCAAAATTTAATTTGGCACAGTCTCATCTGAGCTTATGGAGGGGT -----Exon 6-----(98 bp)
                                                                           |leu asp glu arg asp glu gly lys ala ser ser ala lys gln arg leu
GTTCATGTAGAATTTTCTTCTAATTTTCATCAAATTATTCCTTTTTGTAG|CTC GAT GAA CTT CGG GAT GAA GGG AAG GCT TCG TCT GCC AAA CAG AGA CTC -----Exon 6-----(1,587 bp)
lys cys ala ser leu gln lys phe gly glu arg ala phe lys ala tr|
AAG TGT GCC AGT CTC CAA AAA TTT GGA GAA AGA GCT TTC AAA GCA TG|GTAAATACTTTTAAACATAGTTGGCATCTTTATAACGATGTAAATGATGCTTCA
GTGACAAATTGTACATTTGTACATTTCTTGGTTGTCTAACAGGTAGAACTCTAATAGAGGTAAAAATCAGAATATCATGACAATTTGACATT
ATTTTAATCTCTTTCTTTCTAAATAGTGAATATTTAGAGGACGCTGTCCTTTTGTCTAAAAAAGGACAGATATTTAAGTTCTATTTATTTATAAAATCTTGGACTCTTATTCT
AATGGTTCATTATTTCATTAGAGCTGTAGGCATGGTTCTTTATTTAATTTATTTATTTGTGGATCAGAGTAGGTATACATATTACGGGGTATATGAGATATTT
GATATAAGTATACAACATATATACTCCCTTTATTTCTCCCCCAATGATCTAAAACTATTTGCTTGTCCTTTATGTCTTTATGTCTTATTCAGTCACCAACTAAGTTGAA
GTTACTTCTTATTTTGCATAGCTCCAGCTCGATCTCCATCTCATGTTTTGCCTGAGCCTCTGTTTTCATATTACTTAGTTGGTTCTGGGAGCATACTTTAATAGCCGAGTCAAGAAA
```

FIG. IB-6

```
AATACTAGCTGCCCGTCACCCACACTCCTCACCTGTCAGTCAACAGCAAATCAACACACAGGAAATCAACATTATGCATGCTCTCTAGAAACTGTCAATTGAAC
TGTATTTGCTCATCATTCCTACCATCTACACCACCAAATCAACCAAATTTATGAAAAAAAACAGCCCCAACATAAAATTATACACAGATAAACAGGCTATGATTGGTTTTGGGAAAGA
AGTCACCTTTACCTGATTAGGCAACTGTGAAATGACTAGAGAATGAAGAAAATTAGACGTTTACATCTTGTCATAGAGTTGAAGATAGTGCTGGATCTTTCTTTTTATAAGTAAGATC
AATAAAAACTCCCTCATTCTGTGAGAAGTTATGATTTCTTTTCTAAGAGACCTTTGAAGTCAGAAAAAAATGTGTTTCAATTGAGAACACTGTTGTCATGACATGTTCTCATGACAAGT
ATTATAAAATGCTTTGTATGTATTATCTAATTTAATCCTCAAAACTTCTTCAATTTAGCATGTTGTCATGACACTGTTGTCATGACACTGCTAACACTGCTAACAAGT
CCTACTGCTAACAAGTGATAAAGCCAGAGCTCACATCTGGACTCCAAACCTGATGCTTCTCAGCCTGTTGCCCCTTTAGAGTTCTCTTTTAATTTCTGCTTTATGACTTGCT
AGATTTCTACTACCACCACACACACACTCTTAAATGGATAATTCTGCCCTAAGGATAAGTGATTACCATTGGTTCAGAACTAAGATAAATATTTCTGTATGTCCATTTT
                                                                -----Intron 6|Exon 7----(130 bp)
                                                                              p ala val ala arg leu ser gln
GAATTTCTTATGAGAAATAGTATTTGCCTAGTGTTTCATATAAAATATCGCATGATAATACCATTTGATTGGGCATTTCTTTTTAG|G GCA GTA GCT CGC CTG AGC CAG arg phe pro lys ala glu phe ala glu val ser lys leu thr asp leu val his thr glu cys his gly asp leu leu
AGA TTT CCC AAA GCT GAG TTT GCA GAA GTT TCC AAG CTT ACC AAA GAT CTT GTG ACA GAT CTT GTG CAT TGC CAT GGA GAT CTG CTT -----Exon 7|Intron 7------(1,293 bp)
glu cys ala asp asp arg
GAA TGT GCT GAT GAC AGG|GTAAAGAGTCGTGCATGCTTTTTGGTAGCTTGCATGCTCAAGTTGGTAGAAATGATGCGTTTGGTATCATTGGTGATAGCTGACAGTGGGTTGA
GATTGTCTTCTGTGCTTTCGTGTCTGTCTTGAATCTTTCCTGCCTATGGTGGTACCTTTCTGTTTTAACTGCTATAAATTACCAGATAAACCCATTCACTGATTTGTAACT
CCTTTCAGTCAGTGCTAACGTCTAACTGTAAATGAAACTGAAGTTACAAGGTTTACTTGGCAGAACATCTTGCAAGTAGATGTCTAAGAAGAT******TT******TT
                                                                                                    ↓

AAGACAGAGTTTCGCTCTTGTTTCCCAGGCTGCGGGGTGCAATGGTGTGACCTCCTGGGTTCAAGTGATTTCATGCCTCAGCCTCCCAAGTAGCTGGGA
```

FIG. IB-7

```
TTACAGGCATGCGCCACCACACCTGGCTAATTTTGTATTTTAGTAGAGACGGGGTTTCACCATATTGTCCAGACTGGTCTCGAACTCCTGACCTCAGGTGATCCACCCGCCTTGGCCTC
                                        ════════════════════════════════════════════════════════════════════════════════════════════════
                      A l u 3
CCAAAGTGCTGGGATTACAGGCATGAGCCACCTTGCCCAGCCTAAGAAGATTTTTTGAGGGAGGTAGGTGGACTTGGAGAGAAGGTCACTACTTGAAGAGATTTTTGAAATGATGTATTT
════════════════════════════════════════════════════════════════]********
TCTTCTCTATATTCCTTCCTTGTTAGATGTGCAAATATTTCTCTTTTCTCAAACTTATATATATTTCTTCTCCCTTTCTTCTTCAAGATTAAACTT
ATGGGCAAATACTAGAATCCTAATCTCTCATGGCACTTCTGGAAATTTCTGGAAATATTTAAGGCGGTTTATTTTATATATGTAAGCAGGGCCTATGACTCTTGACTCATTTTCAAAAATCTTCT
ATATTTTATTTAGTGTTCAAAAGGCCTGCACTTATTGCACTTAATTTTGGGGGATTATTTGGAAAAACAGCATTGAGTTTTAATGAAAAAACTTAAATGCCCTAACAGTAGAAACATAAAA
TTAATAAAATAACTGAGCTGAGCACCTGCTACTGATTAGTCTATTTAATTAAGTGGGAATGTTTTGTAGTCCTATCTACTATCTCCAGGTTTAGGAGCAAACAAACAGAGTATGTTCATAGAAG
                                                                                            -----I n t r o n 7---|
GAATATGTGTATGGTCTTAGAATACAATGAACATGTTCTGCCAACTTAATAAAGGTCTGAGGAGAAAGTGTAGCAATGTCAATTCGTGTTGAACAATTTCCACCAACTACTTACTTATAG|
E x o n 8-----(215 bp)                                                                    -----E x o n 8|I n t r o n 8-----(1,399 bp)
ala asp leu ala lys tyr ile cys glu asn gln asp ser ile ser ser lys leu lys glu cys cys glu lys pro leu leu glu lys ser
GCG GAC CTT GCC AAG TAT ATC TGT GAA AAT CAA GAT TCG ATC TCC AGT AAA CTG AAG GAA TGC TGT GAA AAA CCT CTG TTG GAA AAA TCC
his cys ile ala glu val glu asn asp glu met pro ala asp leu pro ser leu ala ala asp phe val glu ser lys asp val cys lys
CAC TGC ATT GCC GAA GTG GAA AAT GAT GAG ATG CCT GCT GAC TTG CCT TCA TTA GCT GCT GAT TTT GTT GAA AGT GAT GTT TGC AAA
asn tyr ala glu lys asp val phe leu gly me|
AAC TAT GCT GAG GCA AAG GAT GTC TTC CTG GGC AT|GTAAGTAGATAGAAGAATTATTCTTTTATAGCTTGGCATGACCTCACAACTTAGGAGGATAGCCTAGGCTTT
CTGTGGAGTTGCTACAATTTCCCTGCTGCCCAGAATGTTTCTTCATCGTTCCCAGGCTTAACAATTTTGAAATAGTAATTAGTTGAATACATTGTCATAAATAATACATG
TTCACGGCAAAGCTCAACATTCTTACTCCTTAGGGTATTTCTAGAAATACGTCTAGAAACATTTGTATATAAATTATGTATACTTCAGTCATTCAAGTGTATTCTTG
AACATCTATAATATATGTGTGACTATGTATTGCCTGTCTATCTAACTAATCTAATCTAGTCTATCTATCTAATTACATGCAATGATGACAAAGAAGTATAAAAGAAATATAGA
GTCTGACACAGGTGCTTATATTTGGTGAAAAGACCAAGTTCAGTAGTAGGCAATATGGTAGGCAACTCAATTACAAAATAAATGTTACGTATTGTCAGAAGTTGTGGTGATAAAC
```

```
CTCATTTTTCCTGCTTTCAAGAAGCTACTGTATGCCAGGCACCATGCACAAACAATGACCAACGTAAAATCTCTCATTTTGGAGAGCCTGAATCTAACTGGAAAGGTGAACTAATAATA
ATAATATGTACAATCATAGCCATCATTATTAAACTTTTATTATATGCAAGGCACTGTTAATTTCATTAGCTTACCTGGTTTACAGAGCAGCTCTATGAGATGAGTGCCATCTTTGCCC
CTATTTAGGGATAAGGATTCCGAAATGTGGAGATGGTAAGTAAAATTGCACAACTGGTAAGAATGAGTACATGACTGGTCATTGAACTCCAGAGCCTGAATATTCTT
AACCCTTACATGATGCAAGCTCACCAAATAAATAGTTCGAATGTATTGTGACAGAGCGGCATTGATATTCATCTATTCATGGCTTTGAGTAGGAAGAAGAAAGGATATCATTCTGAC
CAGAGGGGTGAAAAACAACCTGCATCTGATCCTGAGGCATAATACTATTAACACAATTCTTTATGTTTCAG
                                            -----Intron 9|Exon 10-----(98 bp)
                                                         |phe asp glu phe lys pro leu val glu pro gln
                                                         |TTC GAT GAA TTT AAA CCT CTT GTG GAA GAG CCT CAG
                                                    -----Exon 10|Intron 10-----(1,177 bp)
asn leu ile lys gln asn cys glu leu phe glu gln leu gly glu tyr lys phe lys phe gln asn al|
AAT TTA ATC AAA CAA AAT TGT GAG CTT TTT GAG CAG CTT GGA GAG TAC AAA TTC AAA TTC CAG AAT GC|GTAAGTAATTTTTATTGACTGATTTTTTATCAATT
TGTAATTATTTAAGACTTAATATATGAGCCACCTAGCATAGAACTTTTAAGAATGAAAATACATTGCATATTCTAATCACTCTTTGTCAAGAAAGATAGGAGGAGAGATAAAATAGT
TGATGGGGTGGAGAGGTCTATATTTGAATGTCTAAAAATTGTTCTCTTAAGAGCATGTGAGGCTAAATACCAAATCTTGGTATATCAGAACTGAGAACTGAGCATGTCCCT
TGAAGGTTAAGAAAATAGTTAATGGGCAAATAGAGACATTGGCAATATATTTGTAGAGCAGCAAGTAGTAGGCCTTGATGGTAACCTTTGCTCAAAAGTAATATGTAAGCTGAACACAAAATGT
AACAAATGAATTTAGATACATATTTGAATATTGAATATTTACGAAGGTTAAAAACAAGAGAACATATATTATACAGTAGATATTTATTGTGTGGCTCATACACATGGTGCTCTTCTGATTATGGATTT
ACTAATGTCCCAATTCAATGAGTCTTATCTCACGAAGGTTCTTTCCCTGAGTAGAACATAGTTTCTTTCCTCAGTGAGATTAAGGTATCATACATTGACTTTTAATGGTGACTGGCATTCTAATACATGATTATTATTATAGGTACCATGTC
AGAGAGATAATAACAGTGAACAAGACATAGTTTCTTTCCTCAGTAGAATACATCCTATTGAACTATCCCATTTCCATTTCTACTGTATCTTTCAAGTTTAGCATATGCTGATACATAT
AGATTAATTATAACTTTACTATTTTAATTTAACCCTTGAACTATCCCTATTGAACTATCCCAAGATTATGCAACTCACTTTCCCAAGATTATGCAACTGGAACTCAAGCCAAGTTT
GAAGCTCTCCAGGTTTTATTGAAGAAGAAAATTAATAAATTTATTAATGTCACTGAATTAGGCAACTCACTTTCCCAAGATTATGCAAGTGGTACAGGTGGAACTCAAGCCAAGTTT
AACTAGTTGTTCAGGAGAATGTTTCTACCCTCCCACTACTCTGCAGAGATGGAGATAATATGAATGAACATCTTAGTTGATTCCGGCCAAGTGTTCTCTGTT
```

FIG. 1B-10

```
                -----I n t r o n 10-----|E x o n 11-----(139 bp)                                        -----E x
                                        a leu leu val arg tyr thr lys lys val pro gln val ser thr
TTATCTACTATGTTAGACAGTTTCTTGCCTTGCTGAAAACACATGACTTCTTTTTTCAG|G CTA TTA GTT CGT TAC ACC AAG AAA GTA CCC CAA GTG TCA ACT pro thr leu val glu val ser arg asn leu gly lys val gly ser lys cys cys lys his pro glu ala lys met pro cys ala glu
CCA ACT CTT GTA GAG GTC TCA AGA AAC CTA GGA AAA GTG GGC AGC AAG TGT TGT AAA CAT CCT GAA GCA AAA AGA ATG CCC TGT GCA GAA o n 11|I n t r o n 11-----(418 bp)
asp tyr|
GAC TAT|GTGAGTCTTTAAAAAAATATAATAATTAATGAAAAAAATTTACCTTTAGATATTAGATGATGATAATTTTTTTTTTTGAGACGAGTCTCGCTTTGTCGTGTGCATGTTTG TGTGCATGTGTGTGTGCATGCACGTGTGTATGTGATATTGGCAGTCAAGGCCCCGAGTCAAGGCCCCGAGGATAATTTTTTTTTTTTGAGACGGGACTACAGGTGCATGGGACTGGGAGT GCAGTGGTGCCATCTCGGCTCACTGCAACCTCCGGCCTCAAGCCATTCTCCTGCCTCAGCCTCCCAAGTAGCTGGGACTACAGGTGCATGCCACCATGCCTGGCTAATTTTTT
       Alu5
       GTATTTTAGTAGAGAAATTTCACCTCTTTGAATTTCTGCCTGTTCTTTAG|CTA TCC GTG GTC CTG AAC CAG TTA TGT GTG TTG CAT GAG -----I n t r o n 11|E x o n 12-----(224 bp) leu ser val val leu asn gln leu cys val leu his glu lys ser pro val ser asp arg val thr lys cys cys thr glu ser leu val asn arg arg pro cys phe ser ala leu glu val asp glu
AAA TCC CCA GTA.AGT GAC AGA GTC ACC AAG TGC TGC ACA GAA TCC TTG GTG AAC AGG CGA CCA TGC TTT TCA GCT CTG GAA GTC GAT GAA -----E x
thr tyr val pro lys glu phe asn ala glu thr phe his ala asp ile cys thr leu ser glu arg gln ile lys lys
ACA TAC GTT CCC AAA GAG TTT AAT GCT GAA ACA TTC CAT GCA GAT ATA TGC ACA CTT TCT GAG AAG AGA CAA ATC AAG AAA
```

FIG. IB-II

```
o n 1 2 |I n t r o n 1 2------(1,192 bp)
gln th|
CAA AC|GTGAGGAGTATTCATTACTGCATGTTTGTAGTCTTGATAGCAAGAACTGTCAATTCAAGCTAGCAACTTTTCCTGAAGTAGTAGTGATTATATTTCTTAGAGGAAAGTATTG
GAGTGTTGCCCTTATTATGCTGATAAGAGTACCCAGAGAAATAAAATGAATAAACTTTTAAAGACAAAATCCTCTGTTATAATATTGCTAAAATTATTCAGAGTAATATTGTGATTAAAGCC
ACAATAGAATAACATGTTAGACCATATTCAGTAGAAAAAGATGAACAATTAACTGAAGAAAATTGTGCACATGGCAAATTAGTTAATGGGAACCATAGGAGAGTTATTTCTAGATGTAAA
TAATTATTTAAGTTGCCCTATGGTGGCCCCACACATGAGACACACATGAGAATGACTTGACTTTTGAGAATGACTTGCTGTCATCTCTTGTGGGCTGTAATCATCGTCTAGGCTTAAGAGTAATAITGCAAAACCTGTCATGCC
CCTATTGCTATCATCACAGGGGTTATAATTGCATAAAATTAGCTATAGAAATTTGCTGTGTCATTGTTGTCTTTGCAGATGTCAGTGAAGAGAACCAGAGCCTTATTTCTATAGCCTCCCCACTATTAGCTTTGAAGGGA
CACACAAATCTCTCCCTGGCATTGTTGTCTTTGCAGATGTCAGTGAAGAGAACCAGAGCCTTATTTCTATAGCCTCCCCACTATTAGCTTTGAAGGGA
GCAAAGTTTAAGAACCAAATAATAAAGTTTCTCATCTTTATAGATGAGAAAAATTTAAATAAAGTCCAAGATAATTAAATTTTAGTCTCTTAATAGCAATAAAACT
CAATATGACATATATGGCACTTCCAAAATCTGAATAATATATAATTGCAATGACATACTTCTTTTCAGAGATTTCAATGACACTACATACGTGATGAGTGGTTT
ATACTGATTGTTTCAGTTGGTCTTCCCACCAACTCAGAAGTGGATTTTATTATCCTCATGAGAGAATATTGAGACTTATAGCGGTATGCCTGGCCCAAGTACTCAGAGTT
                                                                                                                                    -----I n t r o n 1 2------
GCCTGGCTCCAAGATTTATAATCTTAAATGATGGGACTACCATCCTTACTCTCTCCATTTTCTACTCTGAGTAATGTTTTTCTGTTTTTTCTTTTCCATTCAAACTCAG|
|E x o n 1 3------(133 bp)
r ala leu val glu leu val lys his lys pro lys ala thr lys glu gln leu lys ala val met asp asp phe val glu
T GCA CTT GTT GAG CTC GTG AAA CAC AAG CCC AAG GCA ACA AAA GAG CAA CTG AAA GCT GTT ATG GAT GAT TTC GCA GCT TTT GTA GAG
                                                                                   -----E x o n 1 3-----|I n t r o n 1 3|GTACTACAGTTCTCTTCATTTAATATGTCCAGTATTCATTTTGCATGTTTGGTTAGGC
lys cys lys ala asp asp lys glu thr cys phe ala glu glu
AAG TGC TGC AAG GCT GAC GAT AAG GAG ACC TGC TTT GCC GAG GAG|
TAGGGCTTAGGGATTTATATATCAAAGGAGGCTTTGTACATGTGGGACAGGATCTTATTTACAAACAATTGTCTTACAAAATGAATAAAACACTTGTTTTTATCTCCTGCTCTA
TTGTGCCATACTGTTGAATGTTATAATGCATGTCTGTTTCCAAATTTGTGATGCTTATGGCTTAGTTGATTTAGGCTTAGTTTATAGGCTGGGAGAATTTACATTCAAATGTCTAAATCACTTAAAATTTCCCTTTATGGCCTGACAG
ATTTATTTAAACATTTACTTGAAATGTCAAATGTGGTTGTGTTTGATTTAGTTGATTTAGGCTGGGAGAATTTACATTCAAATGTCTAAATCACTTAAAATTTCCCTTTATGGCCTGACAG
TAACTTTTTTATTCATTTATTCATTTGGGGACAACTATGTCCGTGAGCTTCCATCCAGAGATTATAGTAGTAATTGTAATTAAGGATAGTAGTAAATGATGCACGTGAAATATGAATCATCAATAGC
```

FIG. 1B-12

```
                                              -----Intron 13|Exon 14------(68 bp)
                                                            gly lys lys leu val ala ala ser gln ala ala
TTCATAAATGTTAATTTGTATCCTAATAGTAATGCTAATATTTTCCTAACATCTGTCATGTCTTGTGTTCAG|GGT AAA AAA CTT GTT GCT GCA AGT CAA GCT GCC leu gly leu ter       -----Exon 14|Intron 14------(770 bp)
TTA GGC TTA TAA CATCACATTTAAAAGCATCTCAG|GTAACTATATTTTGAATTTTTAAAAAAGTAACTATAAGTTATTATTAAATAGCAAAGATTGACCATTTCCAAGAGC
CATATAGACCAGCACCGACCACTACTATTCTAAACTATTTATGTATGTAAATAGTTGCTGAGTTGGGAACCACTATATTTCTATTTTGTAGATGAGAA
AATGAAGATAAACATCAAAGCATAGATAAGTAATTTCCAAAGGTCAAACCAAAGTTCAGTGTTGCCCATTGTCCTGTTCTGACTTATATGCGGTACACA
GAGCCATCCAAGTAAGTGATGGCTCAGCAGTGGAATACTCTGGGAATTAGGCTGAACCACATGAAAAACAGTTGAATATCAGTGATTCACATGGTTCAAC
CTAATAGTTCAACTCATCCTTTCCATTGGAGAATATGAGGATCTACCTTCTGTGAACTTTATAGTGAAGAATCTGCTATTACATTTGTCAACATGCTGAGCTTTAATAGGAC
TTATCTTCTTATGACAACATTTATTGGTGTGTGTCCCCCTTGCCTAGCCCAACAGAGAATTCAGGCTAAATTGTTTTCACTGGTGTAAATTGCAGAAAGAT
                                                     -----Intron 14-----(untrans
GATCTAAGTAATTTGGCATTTATTTTAATAGGTTTGAAAAACACATGCCATTTTACAAATAAGACTTATATTTGTCCTTTTGTTTTTCAG|CCTACCATGAGAATAAGAGAAAGAAAATG
lated 163 bp)
AAGATCAAAAGCTTATCATCTGTTTTCTTTTCGTTGGTGTAAAGCCAACACCCTGTCTAAAAAACATAAATTTCTTAATCATTTTGCCTCTCTTTCTGTGCTTCAATTAATAAAA
                                                                                                                ooooo
                 (A)n                                                            (A)n
AATGGAAAGAATCT⌐AATAGAGTGGTACAGCACTGTTATTTTCAAAGATGTTGTGCTATCCTGAAAATTCTGTAGGTTCTGTGTGGAAGTTCCAGTGTTCTCTCTTATTCCACTTCGGTAG AGGATTTCTAGTTTCTTGTGGGCTAATTAAATAAACATTAATACTCTTCTAAGTT⌐ATGGATTATAAACATTTGACATTATGATAATTCTGAATAAAAGAACAAAA
                                                                                                      ooooo
ACCATGGTATAGGTAAGGAATATAAAACATGGCTTTTACCTTAGAAAAAAACAATTCTAAATTCATATGGAATCAAAAAAGAGCCTGCAG
```

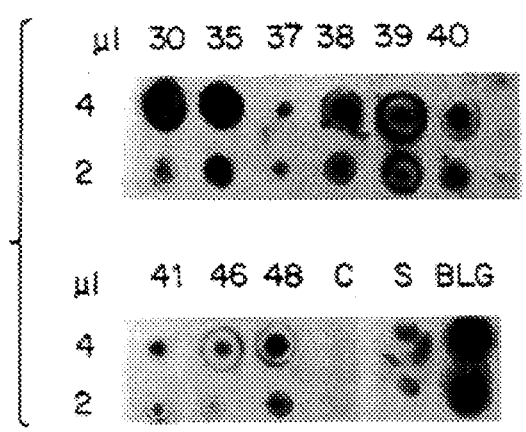 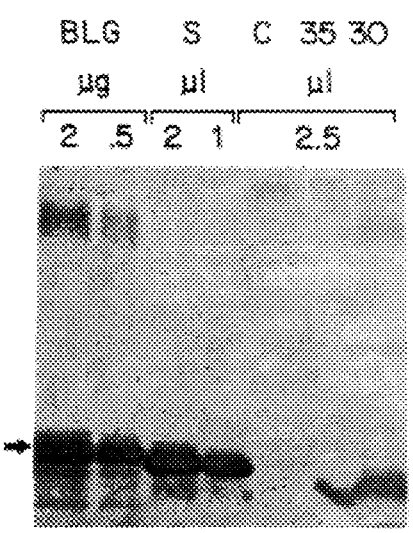
FIG.5A
FIG.5B

I & F at 0.1 ug/ml, P at 1.0 ug/ml
I, F & P at 5 ug/ml

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1:

GTCGACGCGG CCGC 14

( 2 ) INFORMATION FOR SEQ ID NO:2:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

AATTGCGGCC GCGTCGAC                                                            18

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AATTAGCGGC CGCG                                                                14

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GATCCGCGGC CGCT                                                                14

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ATTTAGGTGA CACTATA                                                             17

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGTTTGGGGA CTTCCCTGGT GA                                                       22

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAGGCCAGCA TCACCCTGA                                                           19

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CATGGCAACG ATCGCGAGTC GACG                                                     24

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AATTCGTCGA CTCGCGATCG TTGC 24

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AATACGACTC ACTATAG 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ATTAACCCTC ACTAAAG 17

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CATGGAGATC TGCTTGAA 18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GACTTGCCTT CATTAGCT 18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GAGAAGTGCT GTGCCGCT 18

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GTACCCCAAG TGTCAACT 18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GACAGAGTCA CCAAATGC 18

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GAGAGACAAA TCAAGAAAC 19

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CTCTTATTCT CATGGTAGGC TGA 23

( 2 ) INFORMATION FOR SEQ ID NO:19:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GAATTCGGAT CCCCATGGAG ATCTGCTTGA ATGTGCT 37

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GTCGACCCTA GGCTATCCTC CTAAGTTGT 29

( 2 ) INFORMATION FOR SEQ ID NO:21:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:21:

GTCGACCCTA GGCTTTCTG TGGAGTTGCT 30

( 2 ) INFORMATION FOR SEQ ID NO:22:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:22:

GAATTCAAGC TTAGTAGCTA AGGACTT 27

( 2 ) INFORMATION FOR SEQ ID NO:23:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:23:

GAATTCAAGC TTTACTGCAT GGGGTTTAGT 30

( 2 ) INFORMATION FOR SEQ ID NO:24:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:24:

GTCGACCTCG AGGAAAGAAA CTATGTCTTG T 31

( 2 ) INFORMATION FOR SEQ ID NO:25:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:25:

GTCGACCTCG AGTAGATTAA AGTCATACA 29

( 2 ) INFORMATION FOR SEQ ID NO:26:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:26:

GAATTCGGAT CCGACTCTGT CACTTACTGG CGTT 34

( 2 ) INFORMATION FOR SEQ ID NO:27:

( i ) SEQUENCE CHARACTERISTICS:
( A ) LENGTH: 27 base pairs ( B ) TYPE: nucleic acid
        ( C ) STRANDEDNESS: single
        ( D ) TOPOLOGY: linear ( x i ) SEQUENCE DESCRIPTION: SEQ ID NO:27:

GGTTGCTCAT CGATTTAAAG ATTTGGG          27

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GTACATAAGC TTTGGCACAA TGAAGTGGGT AACCTT          36

( 2 ) INFORMATION FOR SEQ ID NO:29:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CCCAAATCTT TAAATCGATG AGCAACC          27

( 2 ) INFORMATION FOR SEQ ID NO:30:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CCGGGAGATC TAC          13

( 2 ) INFORMATION FOR SEQ ID NO:31:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GTCAGGGGAT CCACAATTTT CAGCTGACTC ATCAG          35

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GTCACATGTG GCTAATGGCT ACTG          24

( 2 ) INFORMATION FOR SEQ ID NO:33:

( i ) SEQUENCE CHARACTERISTICS:
        ( A ) LENGTH: 26 base pairs
        ( B ) TYPE: nucleic acid
        ( C ) STRANDEDNESS: single ( D ) TOPOLOGY: linear ( x i ) SEQUENCE DESCRIPTION: SEQ ID NO:33:

CCTCGAGTAC GTAAGATCTA AGCTTC                                                26

( 2 ) INFORMATION FOR SEQ ID NO:34:

( i ) SEQUENCE CHARACTERISTICS:
                ( A ) LENGTH: 34 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:34:

CCGGGAAGCT TAGATCTTAC GTACTCGAGG AGCT                                       34

( 2 ) INFORMATION FOR SEQ ID NO:35:

( i ) SEQUENCE CHARACTERISTICS:
                ( A ) LENGTH: 35 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:35:

GTCAGGGAAT TCACAATTTT CAGCTGACTC ATCAG                                      35

( 2 ) INFORMATION FOR SEQ ID NO:36:

( i ) SEQUENCE CHARACTERISTICS:
                ( A ) LENGTH: 19011 base pairs
                ( B ) TYPE: nucleic acid
                ( C ) STRANDEDNESS: double
                ( D ) TOPOLOGY: linear ( i i ) MOLECULE TYPE: DNA (genomic)

( i x ) FEATURE:
                ( A ) NAME/KEY: exon
                ( B ) LOCATION: 1737..1854
                ( D ) OTHER INFORMATION: /number=1
                        / citation=([1])

( i x ) FEATURE:
                ( A ) NAME/KEY: intron
                ( B ) LOCATION: 1855..2563
                ( D ) OTHER INFORMATION: /number=1
                        / label=intron1
                        / citation=([1])

( i x ) FEATURE:
                ( A ) NAME/KEY: exon
                ( B ) LOCATION: 2564..2621
                ( D ) OTHER INFORMATION: /number=2
                        / citation=([1])

( i x ) FEATURE:
                ( A ) NAME/KEY: intron
                ( B ) LOCATION: 2622..4075
                ( D ) OTHER INFORMATION: /number=2

( i x ) FEATURE:
                ( A ) NAME/KEY: exon
                ( B ) LOCATION: 4076..4208
                ( D ) OTHER INFORMATION: /number=3
                        / citation=([1])

( i x ) FEATURE:
                ( A ) NAME/KEY: intron
                ( B ) LOCATION: 4209..6040
                ( D ) OTHER INFORMATION: /number=3

( i x ) FEATURE:
                ( A ) NAME/KEY: exon ( B ) LOCATION: 6041..6252
( D ) OTHER INFORMATION: /number=4

( i x ) FEATURE:
( A ) NAME/KEY: intron
( B ) LOCATION: 6253..6801
( D ) OTHER INFORMATION: /number=4

( i x ) FEATURE:
( A ) NAME/KEY: exon
( B ) LOCATION: 6802..6934
( D ) OTHER INFORMATION: /number=5

( i x ) FEATURE:
( A ) NAME/KEY: intron
( B ) LOCATION: 6935..7758
( D ) OTHER INFORMATION: /number=5

( i x ) FEATURE:
( A ) NAME/KEY: exon
( B ) LOCATION: 7759..7856
( D ) OTHER INFORMATION: /number=6

( i x ) FEATURE:
( A ) NAME/KEY: intron
( B ) LOCATION: 7857..9443
( D ) OTHER INFORMATION: /number=6

( i x ) FEATURE:
( A ) NAME/KEY: exon
( B ) LOCATION: 9444..9573
( D ) OTHER INFORMATION: /number=7

( i x ) FEATURE:
( A ) NAME/KEY: intron
( B ) LOCATION: 9574..10866
( D ) OTHER INFORMATION: /number=7

( i x ) FEATURE:
( A ) NAME/KEY: exon
( B ) LOCATION: 10867..11081
( D ) OTHER INFORMATION: /number=8

( i x ) FEATURE:
( A ) NAME/KEY: intron
( B ) LOCATION: 11082..12480
( D ) OTHER INFORMATION: /number=8

( i x ) FEATURE:
( A ) NAME/KEY: exon
( B ) LOCATION: 12481..12613
( D ) OTHER INFORMATION: /number=9

( i x ) FEATURE:
( A ) NAME/KEY: intron
( B ) LOCATION: 12614..13701
( D ) OTHER INFORMATION: /number=9

( i x ) FEATURE:
( A ) NAME/KEY: exon
( B ) LOCATION: 13702..13799
( D ) OTHER INFORMATION: /number=10

( i x ) FEATURE:
( A ) NAME/KEY: intron
( B ) LOCATION: 13800..14976
( D ) OTHER INFORMATION: /number=10

( i x ) FEATURE:
( A ) NAME/KEY: exon
( B ) LOCATION: 14977..15115
( D ) OTHER INFORMATION: /number=11

( i x ) FEATURE:
( A ) NAME/KEY: intron
( B ) LOCATION: 15116..15533
( D ) OTHER INFORMATION: /number=11

( i x ) FEATURE:
( A ) NAME/KEY: exon ( B ) LOCATION: 15534..15757
( D ) OTHER INFORMATION: /number=12

( i x ) FEATURE:
( A ) NAME/KEY: intron
( B ) LOCATION: 15758..16949
( D ) OTHER INFORMATION: /number=12

( i x ) FEATURE:
( A ) NAME/KEY: exon
( B ) LOCATION: 16950..17082
( D ) OTHER INFORMATION: /number=13

( i x ) FEATURE:
( A ) NAME/KEY: intron
( B ) LOCATION: 17083..17696
( D ) OTHER INFORMATION: /number=13

( i x ) FEATURE:
( A ) NAME/KEY: exon
( B ) LOCATION: 17697..17764
( D ) OTHER INFORMATION: /number=14

( i x ) FEATURE:
( A ) NAME/KEY: intron
( B ) LOCATION: 17765..18534
( D ) OTHER INFORMATION: /number=14

( i x ) FEATURE:
( A ) NAME/KEY: CDS
( B ) LOCATION: join(1776..1854, 2564..2621, 4076..4208,
6041..6252, 6802..6934, 7759..7856, 9444..9573,
10867..11081, 12481..12613, 13702..13799,
14977..15115, 15534..15757, 16950..17082,
17697..17741)
( D ) OTHER INFORMATION: /product="human serum albumin"
/ citation=([1])

( i x ) FEATURE:
( A ) NAME/KEY: exon
( B ) LOCATION: 18535..18697
( D ) OTHER INFORMATION: /number=15

( i x ) FEATURE:
( A ) NAME/KEY: 3'UTR
( B ) LOCATION: 17742..18697

( i x ) FEATURE:
( A ) NAME/KEY: 5'UTR
( B ) LOCATION: 1737..1775

( x ) PUBLICATION INFORMATION:
( A ) AUTHORS: Minghetti, P P
Ruffner, D E
Kuang, W- J
Dennison, O E
Hawkins, J W
Beattie, W G
Dugaiczyk, A
( B ) TITLE: MOLECULAR STRUCTURE OF THE HUMAN ALBUMIN
GENE IS REVEALED BY NUCLEOTIDE SEQUENCE WITHIN
q11-22 OF CHROMOSOME 4
( C ) JOURNAL: J. Biol. Chem.
( D ) VOLUME: 261
( F ) PAGES: 6747-6757
( G ) DATE: 1986
( K ) RELEVANT RESIDUES IN SEQ ID NO:36: FROM 1 TO 19011

( x i ) SEQUENCE DESCRIPTION: SEQ ID NO:36:

```
CCTTTCCCAG GGACTTCTAC AAGGAAAAAG CTAGAGTTGG TTACTGACTT CTAATAAATA      60
ATGCCTACAA TTTCTAGGAA GTTAAAAGTT GACATAATTT ATCCAAGAAA GAATTATTTT     120
CTTAACTTAG AATAGTTTCT TTTTCTTTT  CAGATGTAGG TTTTCTGGC  TTTAGAAAAA     180
ATGCTTGTTT TTCTTCAATG GAAAATAGGC ACACTTGTTT TATGTCTGTT CATCTGTAGT     240
CAGAAAGACA AGTCTGGTAT TTCCTTTCAG GACTCCCTTG AGTCATTAAA AAAAATCTTC     300
```

| | | | | | |
|---|---|---|---|---|---|
| CTATCTATCT | ATGTATCTAT | CATCCATCTA | GCTTTGATTT | TTTCCTCTTC | TGTGCTTTAT | 360 |
| TAGTTAATTA | GTACCCATTT | CTGAAGAAGA | ATAACATAA | GATTATAGAA | ATAATTTCT | 420 |
| TTCATTGTAA | GACTGAATAG | AAAAAATTTT | CTTCATTAT | AAGACTGAGT | AGAAAAATA | 480 |
| ATACTTGTT | AGTCTCTGTG | CCTCTATGTG | CCATGAGGAA | ATTTGACTAC | TGGTTTTGAC | 540 |
| TGACTGAGTT | ATTTAATTAA | GTAAATAAC | TGGCTTAGTA | CTAATTATTG | TTCTGTAGTA | 600 |
| TCAGAGAAAG | TTGTTCTTCC | TACTGGTTGA | GCTCAGTAGT | TCTTCATATT | CTGAGCAAAA | 660 |
| GGGCAGAGGT | AGGATAGCTT | TTCTGAGGTA | GAGATAAGAA | CCTTGGGTAG | GAAGGAAGA | 720 |
| TTTATGAAAT | ATTTAAAAAA | TTATTCTTCC | TTCGCTTTGT | TTTTAGACAT | AATGTTAAAT | 780 |
| TTATTTTGAA | ATTTAAAGCA | ACATAAAAGA | ACATGTGATT | TTTCTACTTA | TTGAAAGAGA | 840 |
| GAAAGGAAAA | AAATATGAAA | CAGGGATGGA | AAGAATCCTA | TGCCTGGTGA | AGGTCAAGGG | 900 |
| TTCTCATAAC | CTACAGAGAA | TTTGGGGTCA | GCCTGTCCTA | TTGTATATTA | TGGCAAAGAT | 960 |
| AATCATCATC | TCATTTGGGT | CCATTTTCCT | CTCCATCTCT | GCTTAACTGA | AGATCCCATG | 1020 |
| AGATATACTC | ACACTGAATC | TAAATAGCCT | ATCTCAGGGC | TTGAATCACA | TGTGGGCCAC | 1080 |
| AGCAGGAATG | GGAACATGGA | ATTTCTAAGT | CCTATCTTAC | TTGTTATTGT | TGCTATGTCT | 1140 |
| TTTTCTTAGT | TTGCATCTGA | GGCAACATCA | GCTTTTCAG | ACAGAATGGC | TTTGGAATAG | 1200 |
| TAAAAAAGAC | ACAGAAGCCC | TAAAATATGT | ATGTATGTAT | ATGTGTGTGT | GCATGCGTGA | 1260 |
| GTACTTGTGT | GTAAATTTTT | CATTATCTAT | AGGTAAAAGC | ACACTTGGAA | TTAGCAATAG | 1320 |
| ATGCAATTTG | GGACTTAACT | CTTTCAGTAT | GTCTTATTTC | TAAGCAAAGT | ATTTAGTTTG | 1380 |
| GTTAGTAATT | ACTAAACACT | GAGAACTAAA | TTGCAAACAC | CAAGAACTAA | AATGTTCAAG | 1440 |
| TGGGAAATTA | CAGTTAAATA | CCATGGTAAT | GAATAAAAGG | TACAAATCGT | TTAAACTCTT | 1500 |
| ATGTAAAATT | TGATAAGATG | TTTTACACAA | CTTTAATACA | TTGACAAGGT | CTTGTGGAGA | 1560 |
| AAACAGTTCC | AGATGGTAAA | TATACACAAG | GGATTAGTC | AAACAATTTT | TTGGCAAGAA | 1620 |
| TATTATGAAT | TTTGTAATCG | GTTGGCAGCC | AATGAAATAC | AAAGATGAGT | CTAGTTAATA | 1680 |
| ATCTACAATT | ATTGGTTAAA | GAAGTATATT | AGTGCTAATT | TCCCTCCGTT | TGTCCTAGCT | 1740 |
| TTTCTCTTCT | GTCAACCCCA | CACGCCTTTG | GCACA ATG AAG TGG GTA ACC TTT | | 1793 |
| | | | Met Lys Trp Val Thr Phe | |
| | | | 1             5 | |

| | | |
|---|---|---|
| ATT TCC CTT CTT TTT CTC TTT AGC TCG GCT TAT TCC AGG GGT GTG TTT | | 1841 |
| Ile Ser Leu Leu Phe Leu Phe Ser Ser Ala Tyr Ser Arg Gly Val Phe | | |
|          10              15                  20 | | |
| CGT CGA GAT GCA   C GTAAGAAATC CATTTTCTA TTGTTCAACT TTATTCTAT | | 1894 |
| Arg Arg Asp Ala | | |
|         25 | | |

| | | | | | |
|---|---|---|---|---|---|
| TTTCCCAGTA | AAATAAAGTT | TTAGTAAACT | CTGCATCTTT | AAAGAATTAT | TTGGCATTT | 1954 |
| ATTTCTAAAA | TGGCATAGTA | TTTTGTATTT | GTGAAGTCTT | ACAAGGTTAT | CTTATTAATA | 2014 |
| AAATTCAAAC | ATCCTAGGTA | AAAAAAAAAA | AAGGTCAGAA | TTGTTTAGTG | ACTGTAATTT | 2074 |
| TCTTTTGCGC | ACTAAGGAAA | GTGCAAAGTA | ACTTAGAGTG | ACTGAAACTT | CACAGAATAG | 2134 |
| GGTTGAAGAT | TGAATTCATA | ACTATCCCAA | AGACCTATCC | ATTGCACTAT | GCTTATTTA | 2194 |
| AAAACCACAA | AACCTGTGCT | GTTGATCTCA | TAAATAGAAC | TTGTATTTAT | ATTTATTTTC | 2254 |
| ATTTTAGTCT | GTCTTCTTGG | TTGCTGTTGA | TAGACACTAA | AAGAGTATTA | GATATTATCT | 2314 |
| AAGTTTGAAT | ATAAGGCTAT | AAATATTTAA | TAATTTTTAA | AATAGTATTC | TTGGTAATTG | 2374 |
| AATTATTCTT | CTGTTTAAAG | GCAGAAGAAA | TAATTGAACA | TCATCCTGAG | TTTTCTGTA | 2434 |
| GGAATCAGAG | CCCAATATTT | TGAAACAAAT | GCATAATCTA | AGTCAAATGG | AAAGAAATAT | 2494 |

| | | |
|---|---|---|
| AAAAAGTAAC ATTATTACTT CTTGTTTTCT TCAGTATTTA ACAATCCTTT TTTTTCTTCC | | 2554 |
| CTTGCCCAG AC AAG AGT GAG GTT GCT CAT CGG TTT AAA GAT TTG GGA | | 2601 |
| His Lys Ser Glu Val Ala His Arg Phe Lys Asp Leu Gly | | |
| 30                         35 | | |
| GAA GAA AAT TTC AAA GCC TT GTAAGTTAAA ATATTGATGA ATCAAATTTA | | 2651 |
| Glu Glu Asn Phe Lys Ala Leu | | |
| 40             45 | | |
| ATGTTTCTAA TAGTGTTGTT TATTATTCTA AAGTGCTTAT ATTTCCTTGT CATCAGGGTT | | 2711 |
| CAGATTCTAA AACAGTGCTG CCTCGTAGAG TTTTCTGCGT TGAGGAAGAT ATTCTGTATC | | 2771 |
| TGGGCTATCC AATAAGGTAG TCACTGGTCA CATGGCTATT GAGTACTTCA AATATGACAA | | 2831 |
| GTGCAACTGA GAAACAAAAA CTTAAATTGT ATTTAATTGT AGTTAATTTG AATGTATATA | | 2891 |
| GTCACATGTG GCTAATGGCT ACTGTATTGG ACAGTACAGC TCTGGAACTT GCTTGGTGGA | | 2951 |
| AAGGACTTTA ATATAGGTTT CCTTTGGTGG CTTACCCACT AAATCTTCTT TACATAGCAA | | 3011 |
| GCATTCCTGT GCTTAGTTGG GAATATTTAA TTTTTTTTTT TTTTAAGAC AGGGTCTCGC | | 3071 |
| TCTGTCGCCC AGGCTGGAGT GCAGTGGCGC AATCTCGGCT CACTGCAAAC TCCGCTCCCG | | 3131 |
| GGTTCACGCC ATTCTCCTGC CTCAGCCTCC CGAGTAGCTG GGACTACAGG CGCCCGCCAT | | 3191 |
| CACGCCCGGC TAATCTTTTG TATTTTTAGT AGAGATGGGG TTTCACCGTG TGCCAGGATG | | 3251 |
| GTCTCAATCT CCTGACATCG TGATCTGCCC ACCTCGGCCT CCCAAAGTGC TGGGATTACA | | 3311 |
| GGAGTGAGTC ACCGCGCCCG GCCTATTTAA ATGTTTTTA ATCTAGTAAA AAATGAGAAA | | 3371 |
| ATTGTTTTTT TAAAAGTCTA CCTAATCCTA CAGGCTAATT AAAGACGTGT GTGGGATCA | | 3431 |
| GGTGCGGTGG TTCACACCTG TAATCCCAGC ACTTGGAAG GCTGATGCAG GAGGATTGCT | | 3491 |
| TGAGCCCAGG AGTACAAGAC CAGCCTGGGC AAGTCTCTTT AAAAAAAACA AAACAAACAA | | 3551 |
| ACAAAAAAAT TAGGCATGGT GGCACATGCC TGTAGTCCTA GCTACTTAGG AGGCTGACGT | | 3611 |
| AGGAGGATCG TTTGGACCTG AGAGGTCAAG GCTACAGTGA GCCATGATTG TGCCACTGCA | | 3671 |
| CTCCAGCCTG GGTGACAGAG TGAGACTCTG TCTCAAAAAA GAAAAAGGAA ATCTGTGGGG | | 3731 |
| TTTGTTTTAG TTTTAAGTAA TTCTAAGGAC TTTAAAAATG CCTAGTCTTG ACAATTAGAT | | 3791 |
| CTATTTGGCA TACAATTTGC TTGCTTAATC TATGTGTGTG CATAGATCTA CTGACACACG | | 3851 |
| CATACATATA AACATTAGGG AACTACCATT CTCTTTGCGT AGGAAGCCAC ATATGCCTAT | | 3911 |
| CTAGGCCTCA GATCATACCT GATATGAATA GGCTTTCTGG ATAATGGTGA AGAAGATGTA | | 3971 |
| TAAAGATAG AACCTATACC CATACATGAT TTGTTCTCTA GCGTAGCAAC CTGTTACATA | | 4031 |
| TTAAAGTTTT ATTATACTAC ATTTTCTAC ATCCTTTGTT TCAG G GTG TTG ATT | | 4085 |
| Val Leu Ile | | |
| GCC TTT GCT CAG TAT CTT CAG CAG TGT CCA TTT GAA GAT CAT GTA AAA | | 4133 |
| Ala Phe Ala Gln Tyr Leu Gln Gln Cys Pro Phe Glu Asp His Val Lys | | |
| 50               55                  60                     65 | | |
| TTA GTG AAT GAA GTA ACT GAA TTT GCA AAA ACA TGT GTT GCT GAT GAG | | 4181 |
| Leu Val Asn Glu Val Thr Glu Phe Ala Lys Thr Cys Val Ala Asp Glu | | |
| 70                  75                       80 | | |
| TCA GCT GAA AAT TGT GAC AAA TCA CTT GTAAGTACAT TCTAATTGTG | | 4228 |
| Ser Ala Glu Asn Cys Asp Lys Ser Leu | | |
| 85                    90 | | |
| GAGATTCTTT CTTCTGTTTG AAGTAATCCC AAGCATTTCA AAGGAATTTT TTTAAGTTT | | 4288 |
| TCTCAATTAT TATTAAGTGT CCTGATTTGT AAGAAACACT AAAAAGTTGC TCATAGACTG | | 4348 |
| ATAAGCCATT GTTTCTTTTG TGATAGAGAT GCTTTAGCTA TGTCCACAGT TTTAAAATCA | | 4408 |
| TTTCTTTATT GAGACCAAAC ACAACAGTCA TGGTGTATTT AAATGGCAAT TTGTCATTTA | | 4468 |

```
TAAACACCTC TTTTTAAAAT TGAGGTTTG  GTTTCTTTTT GTAGAGGCTA ATAGGGATAT    4528
GATAGCATGT ATTTATTTAT TTATTTATCT TATTTTATTA TAGTAAGAAC CCTTAACATG    4588
AGATCTACCC TGTTATATTT TTAAGTGTAC AATCCATTAT TGTTAACTAC GGGTACACTG    4648
TTGTATAGCT TACTCATCTT GCTGTATTAA AACTTTGTGC CCATTGATTA GTAACCCCTC    4708
GTTCGTCCT  CCCCCAGCCA CTGGCAACCA GCATTATACT CTTTGATTCT ATGAGTTTGA    4768
CTACTTTAGC TACCTTATAT AAGTGGTATT ATGTACTGTT TATCTTTTA  TGACTGACTT    4828
ATTTCCCTTA GCATAGTGCA TTCAAAGTCC AACCATGTTG TTGCCTATTG CAGAATTTCC    4888
TTCTTTTCAA GGCTGAATAA TATTCCAGTG CATGTGTGTA CCACATTTTC TTTATCCATT    4948
AATTTGTTGA TTGATAGACA TTTAGGTTGG TTTTCTACAT CTTGACTATC ATGAATAGTG    5008
TTGCAATGAA CACAGGAGAG CTACTATCTC TTAGAGATGA TATCATGGTT TTTATCATCA    5068
GAAACACCC  ACTGATTTCT ATGCTAATTT TGTTACCTGG GTGGAATAAT AGTACAGCTA    5128
TATATTCCTC ATTTTAGATA TCTTTGTATT TCTACATACA ATAAAAAGC  AGAGTACTTA    5188
GTCATGTTGA AGAACTTTAA ACTTTTAGTA TTTCCAGATC AATCTTCAAA ACAAGGACAG    5248
GTTTATCTTT CTCTCACCAC TCAATCTATA TATACCTCTT GTGGGCAAGG CCAGTTTTA    5308
TCACTGGAGC CTTTCCCCTT TTTATTATGT ACCTCTCCCT CACAGCAGAG TCAGGACTTT    5368
AACTTTACAC AATACTATGG CTCTACATAT GAAATCTTAA AAATACATAA AAATTAATAA    5428
ATTCTGTCTA GAGTAGTATA TTTTCCCTGG GGTTACGATT ACTTTCATAA TAAAAATTAG    5488
AGATAAGGAA AGGACTCATT TATTGGAAAG TGATTTTAGG TAACATTTCT GGAAGAAAAA    5548
TGTCTATATC TTAATAGTCA CTAATATAT  GATGGATTGT GTTACTCCTC AGTTTTCAAT    5608
GGCATATACT AAAACATGGC CCTCTAAAAA GGGGGCAAAT GAAATGAGAA ACTCTCTGAA    5668
TGTTTTCTC  CCCTAGGTGA ATTCACCTGC TGCTTAGAAG CTTATTTTCT CTTGATTTCT    5728
GTTATAATGA TTGCTCTTAC CCTTTAGTTT TAAGTTTCAA AATAGGAGTC ATATAACTTT    5788
CCTTAAAGCT ATTGACTGTC TTTTTGTCCT GTTTTATTCA CCATGAGTTA TAGTGTGACA    5848
GTTAATTCTT ATGAAAATTA TATAGAGATG GTTAAATCAT CAGAAACTGT AAACCTCGAT    5908
TGGGAGGGGA AGCGGATTTT TAAATGATTT CCTGACCAAG CTTAACCAGT ATATTAAATC    5968
CTTTGTACTG TTCTTTGGCT ATAAAGAAAA AAGGTACTGT CCAGCAACTG AAACCTGCTT    6028
TCTTCCATTT AG CAT ACC CTT TTT GGA GAC AAA TTA TGC ACA GTT GCA       6076
              His Thr Leu Phe Gly Asp Lys Leu Cys Thr Val Ala
                               95                  100

ACT CTT CGT GAA ACC TAT GGT GAA ATG GCT GAC TGC TGT GCA AAA CAA     6124
Thr Leu Arg Glu Thr Tyr Gly Glu Met Ala Asp Cys Cys Ala Lys Gln
            105                 110                 115

GAA CCT GAG AGA AAT GAA TGC TTC TTG CAA CAC AAA GAT GAC AAC CCA     6172
Glu Pro Glu Arg Asn Glu Cys Phe Leu Gln His Lys Asp Asp Asn Pro
    120                 125                 130

AAC CTC CCC CGA TTG GTG AGA CCA GAG GTT GAT GTG ATG TGC ACT GCT     6220
Asn Leu Pro Arg Leu Val Arg Pro Glu Val Asp Val Met Cys Thr Ala
135                 140                 145                 150

TTT CAT GAC AAT GAA GAG ACA TTT TTG AAA  AA GTAAGTAATC              6262
Phe His Asp Asn Glu Glu Thr Phe Leu Lys  Lys
                155                 160

AGATGTTTAT AGTTCAAAAT TAAAAAGCAT GGAGTAACTC CATAGGCCAA CACTCTATAA   6322
AAATTACCAT AACAAAAATA TTTTCAACAT TAAGACTTGG AAGTTTTGTT ATGATGATTT   6382
TTTAAAGAAG TAGTATTTGA TACCACAAAA TTCTACACAG CAAAAAATAT GATCAAAGAT   6442
```

-continued

```
ATTTTGAAGT TTATTGAAAC AGGATACAAT CTTTCTGAAA AATTTAAGAT AGACAAATTA    6502
TTTAATGTAT TACGAAGATA TGTATATATG GTTGTTATAA TTGATTTCGT TTTAGTCAGC    6562
AACATTATAT TGCCAAAATT TAACCATTTA TGCACACACA CACACACACA CACACACTTA    6622
ACCCTTTTTT CCACATACTT AAAGAATGAC AGAGACAAGA CCATCATGTG CAAATTGAGC    6682
TTAATTGGTT AATTAGATAT CTTTGGAATT TGGAGGTTCT GGGGAGAATG TCGATTACAA    6742
TTATTTCTGT AATATTGTCT GCTATAGAAA AGTGACTGTT TTTCTTTTC AAAATTTAGA     6802
```

```
TAC TTA TAT GAA ATT GCC AGA AGA CAT CCT TAC TTT TAT GCC CCG GAA     6850
Tyr Leu Tyr Glu Ile Ala Arg Arg His Pro Tyr Phe Tyr Ala Pro Glu
            165                 170                 175

CTC CTT TTC TTT GCT AAA AGG TAT AAA GCT GCT TTT ACA GAA TGT TGC     6898
Leu Leu Phe Phe Ala Lys Arg Tyr Lys Ala Ala Phe Thr Glu Cys Cys
        180                 185                 190

CAA GCT GCT GAT AAA GCT GCC TGC CTG TTG CCA AAG     GTATTATGCA      6944
Gln Ala Ala Asp Lys Ala Ala Cys Leu Leu Pro Lys
195                 200                 205
```

```
AAAGAATAGA AAAAAGAGT TCATTATCCA ACCTGATTTT GTCCATTTTG TGGCTAGATT    7004
TAGGGAACCT GAGTGTCTGA TACAAACTTT CCGACATGGT CAAAAAGCC TTCCTTTTAT    7064
CTGTCTTGAA AATCTTTCAT CTTTGAAGGC CTACACTCTC GTTCTTCTT TTAAGATTTG    7124
CCAATGATGA TCTGTCAGAG GTAATCACTG TGCATGTGTT TAAAGATTTC ACCACTTTTT   7184
ATGGTGGTGA TCACTATAGT GAAATACTGA AACTTGTTTG TCAAATTGCA CAGCAAGGGG   7244
ACACAGTTCT TGTTTATCTT TTCATGATAA TTTTTAGTAG GGAGGGAATT CAAAGTAGAG   7304
AATTTTACTG CATCTAGATG CCTGAGTTCA TGCATTCATT CCATAAATAT ATATTATGGA   7364
ATGCTTTATT TTCTTTTCTG AGGAGTTTAC TGATGTTGGT GGAGGAGAGA CTGAAATGAA   7424
TTATACACAA AATTTAAAAA TTAGCAAAAT TGCAGCCCCT GGGATATTAG CGTACTCTTT   7484
CTCTGACTTT TCTCCCACTT TTAAGGCTCT TTTTCCTGGC AATGTTTCCA GTTGGTTTCT   7544
AACTACATAG GGAATTCCGC TGTGACCAGA ATGATCGAAT GATCTTTCCT TTTCTTAGAG   7604
AGCAAAATCA TTATTCGCTA AAGGGAGTAC TTGGGAATTT AGGCATAAAT TATGCCTTCA   7664
AAATTTAATT TGGCACAGTC TCATCTGAGC TTATGGAGGG GTGTTTCATG TAGAATTTTT   7724
CTTCTAATTT TCATCAAATT ATTCCTTTTT GTAG        CTC GAT GAA CTT CGG GAT   7776
                                              Leu Asp Glu Leu Arg Asp
                                                                  210
```

```
GAA GGG AAG GCT TCG TCT GCC AAA CAG AGA CTC AAG TGT GCC AGT CTC     7824
Glu Gly Lys Ala Ser Ser Ala Lys Gln Arg Leu Lys Cys Ala Ser Leu
            215                 220                 225

CAA AAA TTT GGA GAA AGA GCT TTC AAA GCA TG      GTAAATACTT          7866
Gln Lys Phe Gly Glu Arg Ala Phe Lys Ala Trp
            230                 235
```

```
TTAAACATAG TTGGCATCTT TATAACGATG TAAATGATAA TGCTTCAGTG ACAAATTGTA    7926
CATTTTTATG TATTTGCAA AGTGCTGTCA AATACATTTC TTTGGTTGTC TAACAGGTAG    7986
AACTCTAATA GAGGTAAAAA TCAGAATATC AATGACAATT TGACATTATT TTAATCTTT    8046
TCTTTTCTAA ATAGTTGAAT AATTTAGAGG ACGCTGTCCT TTTTGTCCTA AAAAAAGGGA   8106
CAGATATTTA AGTTCTATTT ATTTATAAAA TCTTGGACTC TTATTCTAAT GGTTCATTAT   8166
TTTTATAGAG CTGTAGGCAT GGTTCTTTAT TTAATTTTTT AAAGTTATTT TAATTTTTG    8226
TGGATACAGA GTAGGTATAC ATATTTACGG GGTATATGAG ATATTTGAT ATAAGTATAC    8286
AACATATATA ATCCCTTTAT TTAATTTTAT CTTCCCCCCA ATGATCTAAA ACTATTTGCT   8346
TGTCCTTTTA TGTCTTATAG TTAAATTCAG TCACCAACTA AGTTGAAGTT ACTTCTTATT   8406
```

| | | | | | |
|---|---|---|---|---|---|
| TTTGCATAGC | TCCAGCTCTG | ATCTTCATCT | CATGTTTTTG | CCTGAGCCTC | TGTTTTCATA | 8466
| TTACTTAGTT | GGTTCTGGGA | GCATACTTTA | ATAGCCGAGT | CAAGAAAAAT | ACTAGCTGCC | 8526
| CCGTCACCCA | CACTCCTCAC | CTGCTAGTCA | ACAGCAAATC | AACACAACAG | GAAATAAAAT | 8586
| GAAAATAATA | GACATTATGC | ATGCTCTCTA | GAAACTGTCA | ATTGAACTGT | ATTTGCTCAT | 8646
| CATTCCTACC | ATCTACACCA | CCAAAATCAA | CCAAATTTAT | GAAAAAAAA | CAGCCCCAAC | 8706
| ATAAAATTAT | ACACAGATAA | ACAGGCTATG | ATTGGTTTTG | GGAAAGAAGT | CACCTTTACC | 8766
| TGATTTAGGC | AACTGTGAAA | TGACTAGAGA | ATGAAGAAAA | TTAGACGTTT | ACATCTTGTC | 8826
| ATAGAGTTTG | AAGATAGTGC | TGGATCTTTC | TTTTTATAAG | TAAGATCAAT | AAAAACTCCC | 8886
| TCATTCTGTA | GAAGTTATGA | TTTCTTTTCT | AAGAGACCTT | TAGAAGTCAG | AAAAAATGTG | 8946
| TTTCAATTGA | GAAAAAGAT | AACTGGAGTT | TGTGTAGTAC | TTCCCAGATT | ATAAAATGCT | 9006
| TTTGTATGTA | TTATCTAATT | TAATCCTCAA | AACTTCTTCA | ATTAGCATG | TTGTCATGAC | 9066
| ACTGCAGAGG | CTGAAGCTCA | GAGACGCTGA | GCCCTCTGCT | AACAAGTCCT | ACTGCTAACA | 9126
| AGTGATAAAG | CCAGAGCTGG | AAGTCACATC | TGGACTCCAA | ACCTGATGCT | TCTCAGCCTG | 9186
| TTGCCCCTTT | TAGAGTTCCT | TTTTAATTTC | TGCTTTATG | ACTTGCTAGA | TTTCTACCTA | 9246
| CCACACACAC | TCTTAAATGG | ATAATTCTGC | CCTAAGGATA | AGTGATTACC | ATTTGGTTCA | 9306
| GAACTAGAAC | TAATGAATTT | TAAAAATTAT | TTCTGTATGT | CCATTTGAA | TTTTCTTATG | 9366
| AGAAATAGTA | TTTGCCTAGT | GTTTTCATAT | AAAATATCGC | ATGATAATAC | CATTTTGATT | 9426

| | | | | | |
|---|---|---|---|---|---|
| GGCGATTTTC | TTTTTAG G | GCA GTA GCT | CGC CTG AGC | CAG AGA TTT | CCC AAA | 9477
| | | Ala Val Ala | Arg Leu Ser | Gln Arg Phe | Pro Lys |
| | | 240 | | 245 | |

| | | | | |
|---|---|---|---|---|
| GCT GAG TTT | GCA GAA GTT | TCC AAG TTA | GTG ACA GAT | CTT ACC AAA GTC | 9525
| Ala Glu Phe | Ala Glu Val | Ser Lys Leu | Val Thr Asp | Leu Thr Lys Val | |
| 250 | 255 | | 260 | 265 | |

| | | | | |
|---|---|---|---|---|
| CAC ACG GAA | TGC TGC CAT | GGA GAT CTG | CTT GAA TGT | GCT GAT GAC AGG | 9573
| His Thr Glu | Cys Cys His | Gly Asp Leu | Leu Glu Cys | Ala Asp Asp Arg | |
| | 270 | | 275 | 280 | |

| | | | | | |
|---|---|---|---|---|---|
| GTAAAGAGTC | GTCGATATGC | TTTTGGTAG | CTTGCATGCT | CAAGTTGGTA | GAATGGATGC | 9633
| GTTGGTATC | ATTGGTGATA | GCTGACAGTG | GGTTGAGATT | GTCTTCTGTG | CTTTCGTCTG | 9693
| TCCTATCTTC | AATCTTTCCC | TGCCTATGGT | GGTGGTACCT | TTCTGTTTTT | AACCTGCTAT | 9753
| AAATTACCAG | ATAAACCCAT | TCACTGATTT | GTAACTCCTT | TCAGTCATGC | TCTAACTGTA | 9813
| AATGAAGGCT | TAAACTGAAG | TAGAACAGTT | ACAAGGTTTT | ACTTGGCAGA | ACATCTTGCA | 9873
| AGGTAGATGT | CTAAGAAGAT | TTTTTTTTCT | TTTTTAAGA | CAGAGTTTCG | CTCTTGTTTC | 9933
| CCAGGCTGGG | GTGCAATGGT | GTGATCTTGG | CTCAGCGCAA | CCTCTGCCTC | CTGGGTTCAA | 9993
| GTGATTTTCA | TGCCTCAGCC | TCCCAAGTAG | CTGGGATTAC | AGGCATGCGC | CACCACACCT | 10053
| GGCTAATTTT | GTATTTTTAG | TAGAGGCGGG | GTTTCACCAT | ATTGTCCAGA | CTGGTCTCGA | 10113
| ACTCCTGACC | TCAGGTGATC | CACCCGCCTT | GGCCTCCCAA | AGTGCTGGGA | TTACAGGCAT | 10173
| GAGCCACCTT | GCCCAGCCTA | GAAGATTTT | TTGAGGGAGG | TAGGTGGACT | TGGAGAAGGT | 10233
| CACTACTTGA | AGAGATTTTT | GGAAATGATG | TATTTTTCTT | CTCTATATTC | CTTCCCTTAA | 10293
| TTAACTCTGT | TTGTTAGATG | TGCAAATATT | TGGAATGATA | TCTCTTTTCT | CAAAACTTAT | 10353
| AATATTTTCT | TTCTCCCTTT | CTTCAAGATT | AAACTTATGG | GCAAATACTA | GAATCCTAAT | 10413
| CTCTCATGGC | ACTTTCTGGA | AAATTTAAGG | CGGTTATTTT | ATATATGTAA | GCAGGGCCTA | 10473
| TGACTATGAT | CTTGACTCAT | TTTTCAAAAA | TCTTCTATAT | TTTATTTAGT | TATTTGGTTT | 10533

-continued

```
CAAAAGGCCT GCACTTAATT TTGGGGGATT ATTTGGAAAA ACAGCATTGA GTTTTAATGA         10593
AAAAAACTTA AATGCCCTAA CAGTAGAAAC ATAAAATTAA TAAATAACTG AGCTGAGCAC         10653
CTGCTACTGA TTAGTCTATT TTAATTAAGT GGGAATGTTT TTGTAGTCCT ATCTACATCT         10713
CCAGGTTTAG GAGCAAACAG AGTATGTTCA TAGAAGGAAT ATGTGTATGG TCTTAGAATA         10773
CAATGAACAT GTTCTGCCAA CTTAATAAAG GTCTGAGGAG AAAGTGTAGC AATGTCAATT         10833
CGTGTTGAAC AATTTCCACC AACTTACTTA TAG GCG GAC CTT GCC AAG TAT ATC         10887
                                    Ala Asp Leu Ala Lys Tyr Ile
                                                          285
```

```
TGT GAA AAT CAA GAT TCG ATC TCC AGT AAA CTG AAG GAA TGC TGT GAA         10935
Cys Glu Asn Gln Asp Ser Ile Ser Ser Lys Leu Lys Glu Cys Cys Glu
        290             295             300

AAA CCT CTG TTG GAA AAA TCC CAC TGC ATT GCC GAA GTG GAA AAT GAT         10983
Lys Pro Leu Leu Glu Lys Ser His Cys Ile Ala Glu Val Glu Asn Asp
305             310             315                         320

GAG ATG CCT GCT GAC TTG CCT TCA TTA GCT GCT GAT TTT GTT GAA AGT         11031
Glu Met Pro Ala Asp Leu Pro Ser Leu Ala Ala Asp Phe Val Glu Ser
                325             330             335

AAG GAT GTT TGC AAA AAC TAT GCT GAG GCA AAG GAT GTC TTC CTG GGC AT     11081
Lys Asp Val Cys Lys Asn Tyr Ala Glu Ala Lys Asp Val Phe Leu Gly Met
            340             345             350
```

```
GTAAGTAGAT AAGAAATTAT TCTTTTATAG CTTTGGCATG ACCTCACAAC TTAGGAGGAT         11141
AGCCTAGGCT TTTCTGTGGA GTTGCTACAA TTTCCCTGCT GCCCAGAATG TTTCTTCATC         11201
CTTCCCTTTC CCAGGCTTTA ACAATTTTTG AAATAGTTAA TTAGTTGAAT ACATTGTCAT         11261
AAAATAATAC ATGTTCACGG CAAAGCTCAA CATTCCTTAC TCCTTAGGGG TATTTCTGAA         11321
AATACGTCTA GAAACATTTT GTGTATATAT AAATTATGTA TACTTCAGTC ATTCATTCCA         11381
AGTGTATTTC TTGAACATCT ATAATATATG TGTGTGACTA TGTATTGCCT GTCTATCTAA         11441
CTAATCTAAT CTAATCTAGT CTATCTATCT AATCTATGCA ATGATAGCAA AGAAGTATAA         11501
AAAGAAATAT AGAGTCTGAC ACAGGTGCTT TATATTTGGT GAAAAGACCA GAAGTTCAGT         11561
ATAATGGCAA TATGGTAGGC AACTCAATTA CAAAATAAAT GTTTACGTAT TGTCAGAAGT         11621
TGTGGTGATA AACTGCATTT TTGTTGTTGG ATTATGATAA TGCACTAAAT AATATTTCCT         11681
AAAATTATGT ACCCTACAAG ATTTCACTCA TACAGAGAAG AAAGAGAATA TTTTAAGAAC         11741
ATATCTCTGC CCATCTATTT ATCAGAATCC TTTGAGATG TAGTTTAAAT CAAACAAAAT          11801
GTTAATAAAA ATAACAAGTA TCATTCATCA AAGACTTCAT ATGTGCCAAG CAGTGTGTGC         11861
TTTGTGTAGA TTATGTCATA TAGTTCTCAT AATCCACCTT CCGAGACAGA TACTATTTAT         11921
TTTTGAGAC AGAGTTTTAC TCTTGTTGCC CAGGCTGGAG TGCAATGGTG CCATCTCGGC          11981
TCACCACAAC CTTCGCCTCC CAGGTTCAAG CGATTCTCCT GCCTCAGCCT CCTGGGATTA         12041
CAGGCATGCA CCACCATGCC TGGCTAATTT TGTATTTTA GTAGAGATGG GGTTTCACCA          12101
TGTTGGTCAG ACTGGTCTCA AACTCCTGAC CTCTGGTGAT ATGCCTGCCT CAGCCTCCTA         12161
AAGTGCTGGG ATTACAGGCA TGAGCCACTG TGCCCAGCCG ACAGATACTA TTATTATTTC         12221
CATTCTACCG AGAAGGAGAC TAAGGCTCTG ATCATTAAA TAAGTTGCCT AAGGTGATGC          12281
AGTGATATAA GTAGCAGAGC TAGGAATTGA GCCTTGGTAA CTTTAACTCT GGACCCCAAG         12341
TCCTTAGCTA CTAAGCTTTA CTGCATGGGG TTTAGTCAAA TTAAGACTTT TGGAATATGA         12401
GTTACTTTTG AGATTAGCTT TGTGATATTT TTTGTGCTCA TTTGTCCAAC AAAGTCTATT         12461
TTATTTTCAT CTTAATTAG G TTT TTG TAT GAA TAT GCA AGA AGG CAT CCT           12511
                      Phe Leu Tyr Glu Tyr Ala Arg Arg His Pro
```

|     |     |     |     |     |     |     |     | 355 |     |     |     |     | 360 |     |     |       |
|-----|-----|-----|-----|-----|-----|-----|-----|-----|-----|-----|-----|-----|-----|-----|-----|-------|

```
GAT TAC TCT GTC GTG CTG CTG CTG AGA CTT GCC AAG ACA TAT GAA ACC      12559
Asp Tyr Ser Val Val Leu Leu Leu Arg Leu Ala Lys Thr Tyr Glu Thr
    365                 370                 375

ACT CTA GAG AAG TGC TGT GCC GCT GCA GAT CCT CAT GAA TGC TAT GCC      12607
Thr Leu Glu Lys Cys Cys Ala Ala Ala Asp Pro His Glu Cys Tyr Ala
380                 385                 390                 395

AAA GTG   GTAGGTTTAT TGTTGGAAAA AAATGTAGTT CTTTGACTGA TGATTCCAAT     12663
Lys Val
AATGAGAAAG AAAAATAATG CAAGAATGTA AAATGATATA CAGTGCAATT TAGATCTTTT    12723
CTTGAGATGG TTTCAATTCT GGAATCTTAA ACATGAAAGA AAAGTAGCC  TTAGAATGAT    12783
TAACAAAATT TAGACTAGTT AGAATAGAAA GATCTGAATA GAGCAATCTC TAAAAAATTT    12843
TGATCTTTTT TTCTCTTTTT CACAATCCTG AGAACAAAAA AAAATTAAAT TTAAATGTTA    12903
ATTAGAAGAT ATTTAACTTA GATGTAAAGT GAGTTAACCT GATTCCAGGA TTAATCAAGT    12963
ACTAGAATTA GTATCTTATG GCAAATTATA GAACCTATCC CTTTAGAATA TTTTCAAATC    13023
TTTTTGAGGA TGTTTAGGAA TAGTTTTACA AGAAATTAAG TTAGGAGAGG AAATCTGTTC    13083
TGGAGGATTT TTAGGGTTCC CACTAGCATA TGTAATGGTT TCTGAACTAT TCAGAATCAG    13143
AGAAAACTCA TTTTTCCTGC TTTCAAGAAG CTACTGTATG CCAGGCACCA TGCACAAACA    13203
ATGACCAACG TAAAATCTCT CATTTTGGAG AGCCTGGAAT CTAACTGGAA AGGTGAACTA    13263
ATAATAATAA TATGTACAAT CATAGCCATC ATTATTAAA  CTTTTATTAT ATGCAAGGCA    13323
CTGTTTAATT TCATTAGCTT ACCTGGTTTA CAGAGCAGCT CTATGAGATG AGTGCCATCT    13383
TTGCCCCTAT TTTAGGGATA AGGATTCCGA AATGTGGAGA TGGTAAGTAA AATTGCACAA    13443
CTGAAGAATG AGTTACATGA CTTGGCTCAA ATACTGGTCA TTGAACTCCA GAGCCTGAAT    13503
ATTCTTAACC ACTTACATGA TGCAAGCTCA CCAAATAAAT AGTTCGAATG TATTGTGACA    13563
GAGCGGCATT GATATTCATC TATTCATGTG GCTTTGAGTA GGAAGAAGAA AGGATATCAT    13623
TCTGACCAGA GGGGTGAAAA ACAACCTGCA TCTGATCCTG AGGCATAATA CTATTAACAC    13683
AATTCTTTTA TGTTTCAG TTC GAT GAA TTT AAA CCT CTT GTG GAA GAG CCT     13734
                    Phe Asp Glu Phe Lys Pro Leu Val Glu Glu Pro
                                400                 405

CAG AAT TTA ATC AAA CAA AAT TGT GAG CTT TTT GAG CAG CTT GGA GAG      13782
Gln Asn Leu Ile Lys Gln Asn Cys Glu Leu Phe Glu Gln Leu Gly Glu
    410                 415                 420

TAC AAA TTC CAG AAT    GC  GTAAGTAATT TTATTGACT GATTTTTTT            13829
Tyr Lys Phe Gln Asn Ala
425                 430

ATCAATTTGT AATTATTTAA GACTTAATAT ATGAGCCACC TAGCATAGAA CTTTTAAGAA    13889
TGAAAATACA TTGCATATTT CTAATCACTC TTTGTCAAGA AAGATAGGAG AGGAGAGATA    13949
AAATAGTTGA TGGGTGGAG  AGGTCTATAT TTGAATGTAG TCTAAAAATT GTTCTCTTAA    14009
GATTGGAAGT ATGTAGGCTG GGAGGGTAAA TACCAAATCT TGGTATATCA GAACTGAGCA    14069
TGTCCCTTGA AGGTTAAGAA ATAGTTAATG GGCAAATAGA GCATGGCAAT ATTTTGTAGA    14129
GCAGCAAGTA GTAGGCCTTG AATAGATGTC GCTCAAAAAG TAATATGTAA GCTGAACACA    14189
AAAATGTAAC AAATGAATTT AGATACATAT TTGAATATTA AATTCAGGTT GTTTGGGAGA    14249
TGCACCTAGT CTTTGATGGT TAAACCTTTC CCTCCATAGA AGAGACAGAG ACAGAATGGC    14309
TTGCTGGACT AATGTCCCAA TTCAATAGAG TCTTATCTAC GAAGGTAAAA AACAAGAAGA    14369
GACATATTAT ACAGTAGATA TTTATTGTGT GGCTCATACA CATGGTGCTC TTCTGATTAT    14429
GGATTTTAGA GATAATAACA GTGAACAAGA CATAGTTTCT TTCCTCGAGT AGATTAAAGT    14489
```

```
CATACATTGA CTTTTAATGG TGACTGGCAT TCTTAATACA TGATTATTAT ATATTAGGTA         14549

CCATGTCAGA TTAATTATAA TACTTTACTA TTTTTAATTT AACCCTTGAA CTATCCCTAT         14609

TGAGTCAGAT ATATTCCTT  CCATTTCTA  CTTGTATCTT  TCAAGTTTAG CATATGCTGA        14669

TACATATGAA GCTCTCTCCA GGTTTTATTG AAAGAAGAAA TTAATAAATT TATTAATGTC         14729

ACTGAATTAG CAACTCACT  TTCCCAAGAT TATGCAAGTG GTACAGGTGG AACTCAAAGC         14789

CAAGTTTAAC TAGTTGTTCA GGAGAATGTT TTCTACCCTC CACTAACCCA CTACTCTGCA         14849

GATGGAGATA ATATGATGAA TGGAACATAG CAACATCTTA GTTGATTCCG GCCAAGTGTT         14909

CTCTGTTTTA TCTACTATGT TAGACAGTTT CTTGCCTTGC TGAAAACACA TGACTTCTTT         14969

TTTTCAG G CTA TTA GTT CGT TAC ACC AAG AAA GTA CCC CAA GTG TCA            15016
        Leu Leu Val Arg Tyr Thr Lys Lys Val Pro Gln Val Ser
                    435                 440

ACT CCA ACT CTT GTA GAG GTC TCA AGA AAC CTA GGA AAA GTG GGC AGC          15064
Thr Pro Thr Leu Val Glu Val Ser Arg Asn Leu Gly Lys Val Gly Ser
        445             450                 455

AAA TGT TGT AAA CAT CCT GAA GCA AAA AGA ATG CCC TGT GCA GAA GAC          15112
Lys Cys Cys Lys His Pro Glu Ala Lys Arg Met Pro Cys Ala Glu Asp
460             465                 470                 475

TAT GTGAGTCTTT AAAAAAATAT AATAAATTAA TAATGAAAAA ATTTTACCTT                15165
Tyr

TAGATATTGA TAATGCTAGC TTTCATAAGC AGAAGGAAGT AATGTGTGTG TGTGCATGTT         15225

TGTGTGCATG TGTGTGTGCA TGCACGTGTG TGTATGTGTG ATATTGGCAG TCAAGGCCCC         15285

GAGGATGATA ATTTTTTTTT TTTTTTGAG  ACGGAGTCTC GCTTGTTGT  CCAGGCTGGA         15345

GTGCAGTGGT GCCATCTCGG CTCACTGCAA CCTCCGCCTC CCAAGTTCAA GCCATTCTCC         15405

TGCCTCAGCC TCCCAAGTAG CTGGGACTAC AGGTGCATGC CACCATGCCT GGCTAATTTT         15465

TTGTATTTTT AGTAGAAAAT TTTCAGCTTC ACCTCTTTTG AATTTCTGCT CTCCTGCCTG         15525

TTCTTTAG CTA TCC GTG GTC CTG AAC CAG TTA TGT GTG TTG CAT GAG AAA         15575
         Leu Ser Val Val Leu Asn Gln Leu Cys Val Leu His Glu Lys
                    480                 485                 490

ACG CCA GTA AGT GAC AGA GTC ACC AAA TGC TGC ACA GAA TCC TTG GTG          15623
Thr Pro Val Ser Asp Arg Val Thr Lys Cys Cys Thr Glu Ser Leu Val
            495                 500                 505

AAC AGG CGA CCA TGC TTT TCA GCT CTG GAA GTC GAT GAA ACA TAC GTT          15671
Asn Arg Arg Pro Cys Phe Ser Ala Leu Glu Val Asp Glu Thr Tyr Val
            510                 515                 520

CCC AAA GAG TTT AAT GCT GAA ACA TTC ACC TTC CAT GCA GAT ATA TGC          15719
Pro Lys Glu Phe Asn Ala Glu Thr Phe Thr Phe His Ala Asp Ile Cys
        525                 530                 535

ACA CTT TCT GAG AAG GAG AGA CAA ATC AAG AAA CAA AC  GTGAGGAGTA           15767
Thr Leu Ser Glu Lys Glu Arg Gln Ile Lys Lys Gln Thr
        540                 545                 550

TTTCATTACT GCATGTGTTT GTAGTCTTGA TAGCAAGAAC TGTCAATTCA AGCTAGCAAC        15827

TTTTTCCTGA AGTAGTGATT ATATTTCTTA GAGGAAAGTA TTGGAGTGTT GCCCTTATTA        15887

TGCTGATAAG AGTACCCAGA ATAAATGAA  TAACTTTTTA AAGACAAAAT CCTCTGTTAT        15947

AATATTGCTA AAATTATTCA GAGTAATATT GTGGATTAAA GCCACAATAG AATAACATGT        16007

TAGACCATAT TCAGTAGAAA AAGATGAACA ATTAACTGAT AAATTTGTGC ACATGGCAAA        16067

TTAGTTAATG GGAACCATAG GAGAATTTAT TTCTAGATGT AAATAATTAT TTTAAGTTTG        16127

CCCTATGGTG GCCCCACACA TGAGACAAAC CCCCAAGATG TGACTTTTGA GAATGAGACT        16187
```

-continued

| | | | | |
|---|---|---|---|---|
| TGGATAAAAA | ACATGTAGAA | ATGCAAGCCC | TGAAGCTCAA | CTCCCTATTG | CTATCACAGG | 16247 |
| GGTTATAATT | GCATAAAATT | TAGCTATAGA | AAGTTGCTGT | CATCTCTTGT | GGGCTGTAAT | 16307 |
| CATCGTCTAG | GCTTAAGAGT | AATATTGCAA | AACCTGTCAT | GCCCACACAA | ATCTCTCCCT | 16367 |
| GGCATTGTTG | TCTTTGCAGA | TGTCAGTGAA | AGAGAACCAG | CAGCTCCCAT | GAGTTTGGAT | 16427 |
| AGCCTTATTT | TCTATAGCCT | CCCCACTATT | AGCTTGAAG | GGAGCAAAGT | TTAAGAACCA | 16487 |
| AATATAAAGT | TTCTCATCTT | TATAGATGAG | AAAAATTTTA | AATAAAGTCC | AAGATAATTA | 16547 |
| AATTTTTAAG | GATCATTTTT | AGCTCTTTAA | TAGCAATAAA | ACTCAATATG | ACATAATATG | 16607 |
| GCACTTCCAA | AATCTGAATA | ATATATAATT | GCAATGACAT | ACTTCTTTTC | AGAGATTTAC | 16667 |
| TGAAAGAAA | TTTGTTGACA | CTACATAACG | TGATGAGTGG | TTTATACTGA | TTGTTTCAGT | 16727 |
| TGGTCTTCCC | ACCAACTCCA | TGAAAGTGGA | TTTTATTATC | CTCATCATGC | AGATGAGAAT | 16787 |
| ATTGAGACTT | ATAGCGGTAT | GCCTGGCCCA | AGTACTCAGA | GTTGCCTGGC | TCCAAGATTT | 16847 |
| ATAATCTTAA | ATGATGGGAC | TACCATCCTT | ACTCTCTCCA | TTTTCTATA | CGTGAGTAAT | 16907 |
| GTTTTTTCTG | TTTTTTTTTT | TTCTTTTTCC | ATTCAAACTC | AGT GCA CTT GTT GAG | 16962 |

Ala Leu Val Glu
555

```
CTC GTG AAA CAC AAG CCC AAG GCA ACA AAA GAG CAA CTG AAA GCT GTT    17010
Leu Val Lys His Lys Pro Lys Ala Thr Lys Glu Gln Leu Lys Ala Val
            560             565              570

ATG GAT GAT TTC GCA GCT TTT GTA GAG AAG TGC TGC AAG GCT GAC GAT    17058
Met Asp Asp Phe Ala Ala Phe Val Glu Lys Cys Cys Lys Ala Asp Asp
        575             580              585

AAG GAG ACC TGC TTT GCC GAG GAG GTACTACAGT TCTCTTCATT TAATATGTC    17112
Lys Glu Thr Cys Phe Ala Glu Glu
        590             595
```

| | | | | |
|---|---|---|---|---|
| CAGTATTCAT | TTTTGCATGT | TTGGTTAGGC | TAGGGCTTAG | GGATTTATAT | ATCAAAGGAG | 17172 |
| GCTTTGTACA | TGTGGGACAG | GGATCTTATT | TTACAAACAA | TTGTCTTACA | AAATGAATAA | 17232 |
| AACAGCACTT | TGTTTTATC | TCCTGCTCTA | TTGTGCCATA | CTGTTGAATG | TTTATAATGC | 17292 |
| ATGTTCTGTT | TCCAAATTTG | TGATGCTTAT | GAATATTAAT | AGGAATATTT | GTAAGGCCTG | 17352 |
| AAATATTTTG | ATCATGAAAT | CAAAACATTA | ATTTATTTAA | ACATTTACTT | GAAATGTGGT | 17412 |
| GGTTTGTGAT | TTAGTTGATT | TTATAGGCTA | GTGGGAGAAT | TTACATTCAA | ATGTCTAAAT | 17472 |
| CACTTAAAAT | TTCCCTTTAT | GGCCTGACAG | TAACTTTTTT | TTATTCATTT | GGGGACAACT | 17532 |
| ATGTCCGTGA | GCTTCCATCC | AGAGATTATA | GTAGTAAATT | GTAATTAAAG | GATATGATGC | 17592 |
| ACGTGAAATC | ACTTTGCAAT | CATCAATAGC | TTCATAAATG | TTAATTTTGT | ATCCTAATAG | 17652 |
| TAATGCTAAT | ATTTTCCTAA | CATCTGTCAT | GTCTTTGTGT | TCAG GGT AAA AAA CTT | 17708 |

Gly Lys Lys Leu

```
GTT GCT GCA AGT CAA GCT GCC TTA GGC TTA TAA CATCACATTT AAAAGCATCT    17761
Val Ala Ala Ser Gln Ala Ala Leu Gly Leu *
600             605              610
```

| | | | | |
|---|---|---|---|---|
| CAGGTAACTA | TATTTTGAAT | TTTTTAAAAA | AGTAACTATA | ATAGTTATTA | TTAAAATAGC | 17821 |
| AAAGATTGAC | CATTTCCAAG | AGCCATATAG | ACCAGCACCG | ACCACTATTC | TAAACTATTT | 17881 |
| ATGTATGTAA | ATATTAGCTT | TTAAAATTCT | CAAAATAGTT | GCTGAGTTGG | GAACCACTAT | 17941 |
| TATTTCTATT | TTGTAGATGA | GAAAATGAAG | ATAAACATCA | AAGCATAGAT | TAAGTAATTT | 18001 |
| TCCAAGGGT | CAAAATTCAA | AATTGAAACC | AAGGTTTCAG | TGTTGCCCAT | TGTCCTGTTC | 18061 |
| TGACTTATAT | GATGCGGTAC | ACAGAGCCAT | CCAAGTAAGT | GATGGCTCAG | CAGTGGAATA | 18121 |
| CTCTGGGAAT | TAGGCTGAAC | CACATGAAAG | AGTGCTTTAT | AGGGCAAAAA | CAGTTGAATA | 18181 |

| | | | | | | |
|---|---|---|---|---|---|---|
| TCAGTGATTT | CACATGGTTC | AACCTAATAG | TTCAACTCAT | CCTTTCCATT | GGAGAATATG | 18241 |
| ATGGATCTAC | CTTCTGTGAA | CTTTATAGTG | AAGAATCTGC | TATTACATTT | CCAATTTGTC | 18301 |
| AACATGCTGA | GCTTTAATAG | GACTTATCTT | CTTATGACAA | CATTTATTGG | TGTGTCCCCT | 18361 |
| TGCCTAGCCC | AACAGAAGAA | TTCAGCAGCC | GTAAGTCTAG | GACAGGCTTA | AATTGTTTTC | 18421 |
| ACTGGTGTAA | ATTGCAGAAA | GATGATCTAA | GTAATTTGGC | ATTTATTTA | ATAGGTTTGA | 18481 |
| AAAACACATG | CCATTTTACA | AATAAGACTT | ATATTTGTCC | TTTTGTTTTT | CAGCCTACCA | 18541 |
| TGAGAATAAG | AGAAAGAAAA | TGAAGATCAA | AAGCTTATTC | ATCTGTTTTT | CTTTTTCGTT | 18601 |
| GGTGTAAAGC | CAACACCCTG | TCTAAAAAAC | ATAAATTTCT | TTAATCATTT | TGCCTCTTTT | 18661 |
| CTCTGTGCTT | CAATTAATAA | AAAATGGAAA | GAATCTAATA | GAGTGGTACA | GCACTGTTAT | 18721 |
| TTTTCAAAGA | TGTGTTGCTA | TCCTGAAAAT | TCTGTAGGTT | CTGTGGAAGT | TCCAGTGTTC | 18781 |
| TCTCTTATTC | CACTTCGGTA | GAGGATTTCT | AGTTCTTGT | GGGCTAATTA | AATAAATCAT | 18841 |
| TAATACTCTT | CTAAGTTATG | GATTATAAAC | ATTCAAAATA | ATATTTGAC | ATTATGATAA | 18901 |
| TTCTGAATAA | AAGAACAAAA | ACCATGGTAT | AGGTAAGGAA | TATAAACAT | GGCTTTTACC | 18961 |
| TTAGAAAAAA | CAATTCTAAA | ATTCATATGG | AATCAAAAAA | GAGCCTGCAG | | 19011 |

HUMAN SERUM ALBUMIN EXPRESSION CONSTRUCT

This is a continuation of application Ser. No. 07/737,853 filed on Jul. 31, 1991, now abandoned.

FIELD OF THE INVENTION

This invention relates to HSA-encoding DNA molecules, vectors containing same and HSA-producing transgenic mammals.

BACKGROUND OF THE INVENTION

Human serum albumin (HSA) is a globular, non-glycosylated protein (MW 65,000) synthesized by the liver. Circulating in the blood stream at levels of 42 gr/liter, it is the most abundant serum protein. HSA is involved in a number of essential functions, including sustaining normal bloodstream osmolarity, regulating blood pressure and transporting fatty acids, amino acids, bile pigments and numerous small molecules. Clinically, HSA is used in large quantities to replace blood volume in acute phase conditions such as trauma and severe burns or surgical procedures. Currently, medical supply of HSA depends on the fractionation of donated human blood. At the present time, the cost of purifying HSA from blood is relatively low, since HSA as well as other blood products can be simultaneously purified from the same source. However, as other blood products, such as coagulation factors, are produced by biotechnology instead of purified from human blood, market dynamics will increase the relative cost of purification of HSA from blood. The threat of a diminishing supply of donated blood, rising costs of purifying HSA from blood and the potential risk of contamination with infectious viruses that cause hepatitis, AIDS and other diseases make an alternative source of production of large quantities of HSA desirable. As such, alternative approaches to the production of large quantities of HSA are required.

Recombinant DNA technology has been used increasingly over the past decade for the production of commercially important biological materials. To this end, the DNA sequences encoding a variety of medically important human proteins have been cloned. These include insulin, plasminogen activator, alpha-antitrypsin and coagulation factors VIII and IX.

The expression of DNA sequences encoding these and other proteins has been suggested as the ideal source for the production of large quantities of mammalian proteins. A variety of hosts have been utilized for the production of medically important proteins including bacteria yeast, cultured cells and animals. In practice, bacteria and yeast often prove unsatisfactory as hosts because the foreign proteins are often unstable and are not processed correctly. However, in bacteria the HSA is produced as an insoluble aggregate which requires processing to yield the mature, soluble protein. HSA has also been produced in yeast but at significantly lower levels and in which a high proportion is either fragmented, cell associated or insoluble (Sleep et al, 1990, Bio/technology 8:42–46; Etcheverry et al., 1986, Bio/Technology 4:729–730; Quirk et al., 1989, Biotech. and Applied Biochem. 11:273–287).

In light of this problem, the expression of cloned genes in mammalian tissue culture has been attempted and has, in some instances, proved a viable strategy. However, batch fermentation of animal cells is an expensive and technically demanding process. Transgenic animals have also been proposed as a source for the production of protein products. The production of transgenic livestock offers a number of potential applications including "Molecular Farming" (also referred to as Genetic Farming) where proteins of medical or commercial importance are targeted for high level expression and production in the mammary gland with subsequent secretion into the milk of such genetically engineered animals. The feasibility of this approach was first tested in transgenic mice.

WO-A-8800239 discloses transgenic animals which secrete a valuable pharmaceutical protein, in this case Factor IX, into the milk of transgenic sheep. EP-A-0264166 also discloses the general idea of transgenic animals secreting pharmaceutical proteins into their milk.

Early work with transgenic animals, as represented by WO-A-8800239 has used genetic constructs based on cDNA coding for the protein of interest. The cDNA will be smaller than the natural gene, assuming that the natural gene has introns, and for that reason is easier to manipulate. It is desirable for commercial purposes to improve upon the yields of proteins produced in the milk of the transgenic animal.

Brinster et al (PNAS 85 836–840 (1988)) have demonstrated that the transcriptional efficiency of transgenes having introns in transgenic mice is increased over that of cDNA. Brinster et al show that all the exons and introns of a natural gene are important both for efficient and for reliable expression (that is to say, both the levels of the expression and the proportion of expressing animals) and is due to the presence of the natural introns in that gene. It is known that in some cases this is not attributable to the presence of tissue-specific regulatory sequences in introns, because the phenomenon is observed when the expression of a gene is redirected by a heterologous promoter to a tissue in which it is not normally expressed. Brinster et al say that the effect is peculiar to transgenic animals and is not seen in cell lines. However, Huang and Gorman (1990, Nucleic Acids Research 18:937–947) have demonstrated that a heterologous intron linked to a reporter gene can increase the level of expression of that gene in tissue culture cells.

The problems of yield and reliability of expression can not be overcome by merely following the teaching of Brinster et at and inserting into mammalian genomes transgenes based on natural foreign genes as opposed to foreign cDNA. First, as mentioned above, natural genes having introns are larger than the cDNA coding for the product of the gene since the introns are removed from the primary transcription product before export from the nucleus as mRNA. It is technically difficult to handle large genomic DNA.

Secondly, the longer the length of manipulated DNA, the greater chance that restriction sites occur more than once, thereby making manipulation more difficult. This is especially so given the fact that in most transgenic techniques, the DNA to be inserted into the mammalian genome will often be isolated from prokaryotic vector sequences (because the DNA will have been manipulated in a prokaryotic vector, for choice). The prokaryotic vector sequences usually have to be removed, because they tend to inhibit expression. So the longer the piece of DNA, the more difficult it is to find a restriction enzyme which will not cleave it internally.

Attempts to achieve protein expression utilizing cDNA encoding the protein instead of the full length gene, have generally resulted in low protein yields. A number of workers recognized the desirability of improving upon the yields and reliability of transgenic techniques obtained when using constructs based on cDNA.

Archibald et al. (WO90/05188) noted that with certain proteins higher yields (than could be obtained utilizing cDNA) could be obtained when at least some of the naturally occurring introns were utilized. Palmiter et al. (1991, Proc. Natl. Acad. Sci. USA 88:478–482) also found that the level of expression of a transgene was higher when the transgene included some introns as compared with the transgene composed of a cDNA. However, the level of expression with less then all of its natural introns was reduced when compared to the level of expression obtained with the entire gene with all of its introns.

SUMMARY OF THE INVENTION

The present invention provides DNA constructs comprising a promoter DNA sequence and a DNA sequence coding for human serum albumin. In one embodiment the human serum albumin sequence comprises at least one, but not all, of the introns in the naturally occurring gene encoding for the HSA protein. In another embodiment the DNA constructs comprise a 5' regulatory sequence which directs the expression and secretion of HSA protein in the milk of a transgenic animal. Preferably, the promoter gene is a milk protein promoter sequence such as β-lactoglobulin, whey acidic protein or β-casein. Most preferably the secreted protein is human serum albumin. The present invention also provides vectors comprising the constructs of the present invention.

The DNA construct of the present invention encoding HSA comprises two contiguous exons encoding HSA and an HSA intron. In a preferred embodiment, the DNA construct of the present invention provides for expression of HSA in mammalian cells and milk at higher levels than the naturally occurring HSA gene or HSA cDNA. In a most preferred embodiment the DNA construct of the present invention comprises HSA exons and introns selected from the group consisting of introns 1–6, 7–14, 1+7–14, 1+2+12–14, 2+12–14, 2+7–14 and 1+2+7–14.

In another embodiment, a DNA construct of the present invention encoding HSA comprises one but not all of the first 7 introns of the HSA gene, and one of the last 7 introns of the HSA gene.

In another embodiment, a DNA construct comprising DNA sequences encoding human serum albumin under the control of a mammary tissue specific promoter, said DNA construct expressed by the mammary glands of a lactating female transgenic mammal is provided.

The present invention also provides a transgenic mammal having incorporated into its genome a DNA construct comprising DNA sequences encoding human serum albumin operably linked to a mammary tissue specific promoter, said DNA construct expressed by the mammary glands of a lactating female transgenic mammal. Preferably, the promoter is the β-lactoglobulin protein promoter.

The present invention also provides a method of making a transgenic mammal having incorporated into its genome a DNA construct encoding human serum albumin and a mammary tissue specific promoter, said DNA construct expressed by mammary glands of a lactating female transgenic mammal comprising providing a DNA construct containing the β-lactoglobulin promoter operably linked with nucleotide sequence encoding human serum albumin.

The present invention also provides a transgenic mammal which secretes HSA in the milk of lactating females.

Other and further objects features and advantages will be apparent from the following description of the presently preferred embodiments of the invention, given for the purposes of disclosure when taken in conjunction with the accompanying drawings.

BRIEF DESCRIPTION OF THE FIGURES

The invention will be more readily understood from a reading of the following specification and by reference to the accompanying drawings forming a part thereof:

FIG. 5 demonstrates a dot blot analysis (5A) and a Western analysis (5B) of BLG expression in the milk of transgenic animals;

DETAILED DESCRIPTION OF THE PREFERRED EMBODIMENTS

Figure 1A:
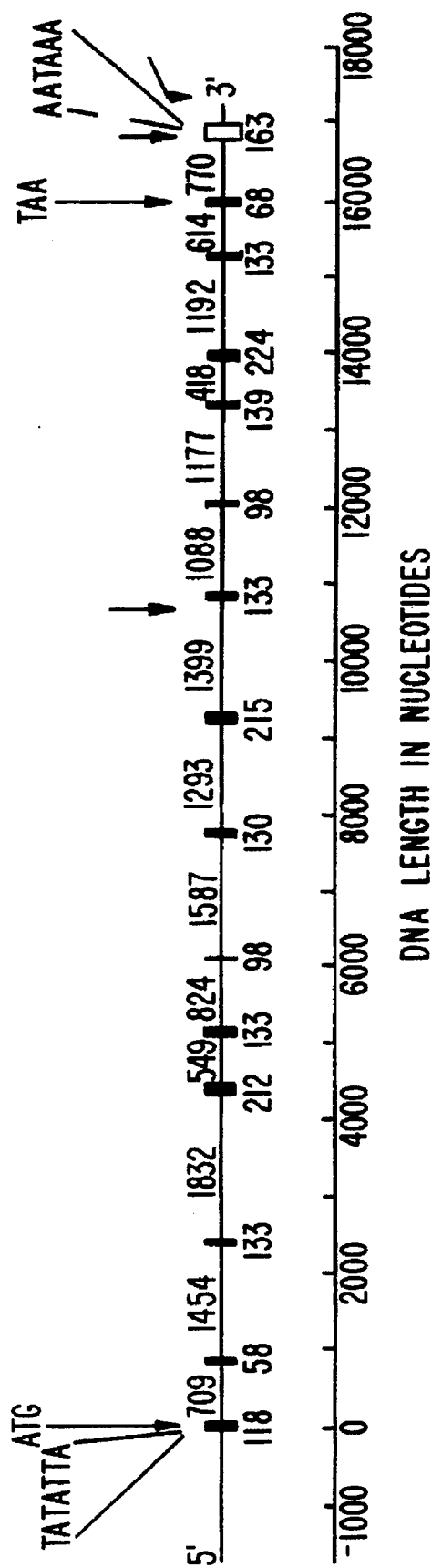
FIG. 1 is a map of the human serum albumin gene (1A) and the sequence of the HSA gene (1B) [SEQ ID NO:36]

Definitions:

The term "naturally occurring HSA gene" means the DNA sequences which encode the HSA protein and includes exons and introns in their native positional relationships. The naturally occurring HSA gene has been sequenced and the sequence reported by Minghetti et al., J. Biol. Chem. 261:6747–6757 (1986). As used herein, HSA base pair (bp) positions are related to this published sequence which is also shown on FIG. 1B [SEQ ID NO:36]. The numbering system used herein is defined such that the first bp (A) of the HSA translational initiation codon (ATG) is numbered as bp 1776 which is bp 40 on the sequence shown on FIG. 1B [SEQ ID NO:36]. In the native state the HSA gene includes 5' flanking sequences (including promoter sequences) which are responsible for initiation and regulation of transcription and expression and 3' flanking sequences, as used herein the term "naturally occurring HSA gene" need not include these flanking sequences. In the constructs of the present invention the native flanking sequences may be absent or substituted by a heterologous sequence.

As used herein, the term "intron" (also called intervening sequences) are those sequences of a naturally occurring gene which are included within the transcription unit of the gene but do not encode the natural HSA gene product protein. The introns are transcribed into the precursor RNA, but are removed during the processing (splicing) of the RNA to its mature form, messenger RNA (mRNA). The introns are located between flanking exons. In this specification the term "intron" includes the whole of any natural intron or part thereof.

As used herein the term "exon" refers to DNA sequences which are included within the transcription unit of the gene and maintained in the mature mRNA following processing and encode the gene product protein. When an intron is deleted or removed from the naturally occurring gene, the two exons which naturally flank that intron become adjoined as contiguous exons.

The DNA constructs of the present invention will generally be suitable for use in expressing the HSA protein in mammalian cells and, preferably, in the mammary gland of a transgenic animal with subsequent secretion of HSA in the milk. The DNA constructs of the present invention comprise DNA sequences encoding the HSA protein together with 5' flanking regulatory elements which include promoter sequences. When expression in mammary tissue is desired the 5' regulatory sequences are chosen which directs the expression and secretion of HSA protein in the milk of a transgenic animal. Preferably, the promoter is a milk protein promoter sequence such as β-lactoglobulin, whey acidic protein or β-casein. When expression of the HSA encoding construct of the present invention in tissue culture cells is desired, an enhancer sequence may be included in the construct. Enhance elements may be derived from SV40, human cytomegalovirus or any other source. The choice of enhancer will be known to one of skill in the art. The constructs of the present invention also comprises polyadenylation (poly (A)) signals and sites. The polyadenylation signal may be a homologous signal encoded by the native HSA gene or may be heterologous, for example, the BLG or SV40 poly (A) sites. The choice of promoter, poly (A) or other regulatory elements will be known to those of skill in the art.

The species of animals selected for expression is not particularly critical, and will be selected by those skilled in the art to be suitable for their needs. Clearly, if secretion in the mammary gland is the primary goal, as is the case with preferred embodiments of the invention, it is essential to use mammals. Suitable laboratory mammals for experimental ease of manipulation include mice and rats. Domestic farm animals such as rabbits, cows, pigs, goats and sheep provide larger yields than other mammals. Preferably, sheep and goats are utilized because of the relative annual milk production in relation to generation time, experimental production time, and cost.

According to another aspect of the invention, there is provided a vector (or DNA construct) comprising a genetic construct comprising at least one HSA intron and fewer than all of the HSA introns which vector when used to transfect a mammalian cell expresses HSA at a higher level of expression than the full naturally occurring HSA gene.

According to another aspect of the invention, there is provided a mammalian or other animal cell comprising a construct as described above. According to a sixth aspect of the invention, there is provided a transgenic mammal or other animal comprising a genetic construct as described above integrated into its genome. It is particularly preferred that the transgenic animal transmits the construct to its progeny, thereby enabling the production of at least one subsequent generation of producer animals.

Figures 1, 2A:
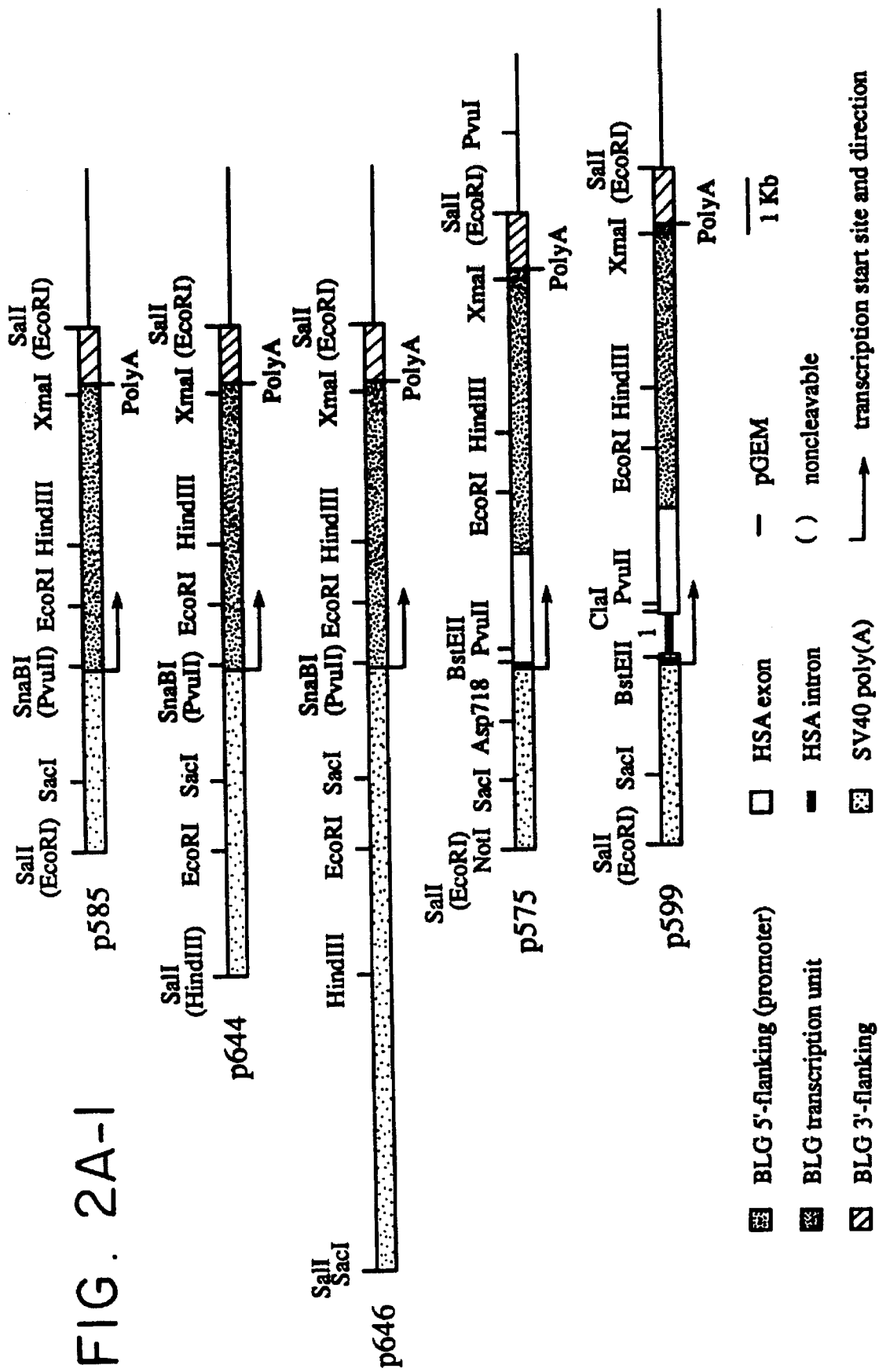
Figures 2, 2A:
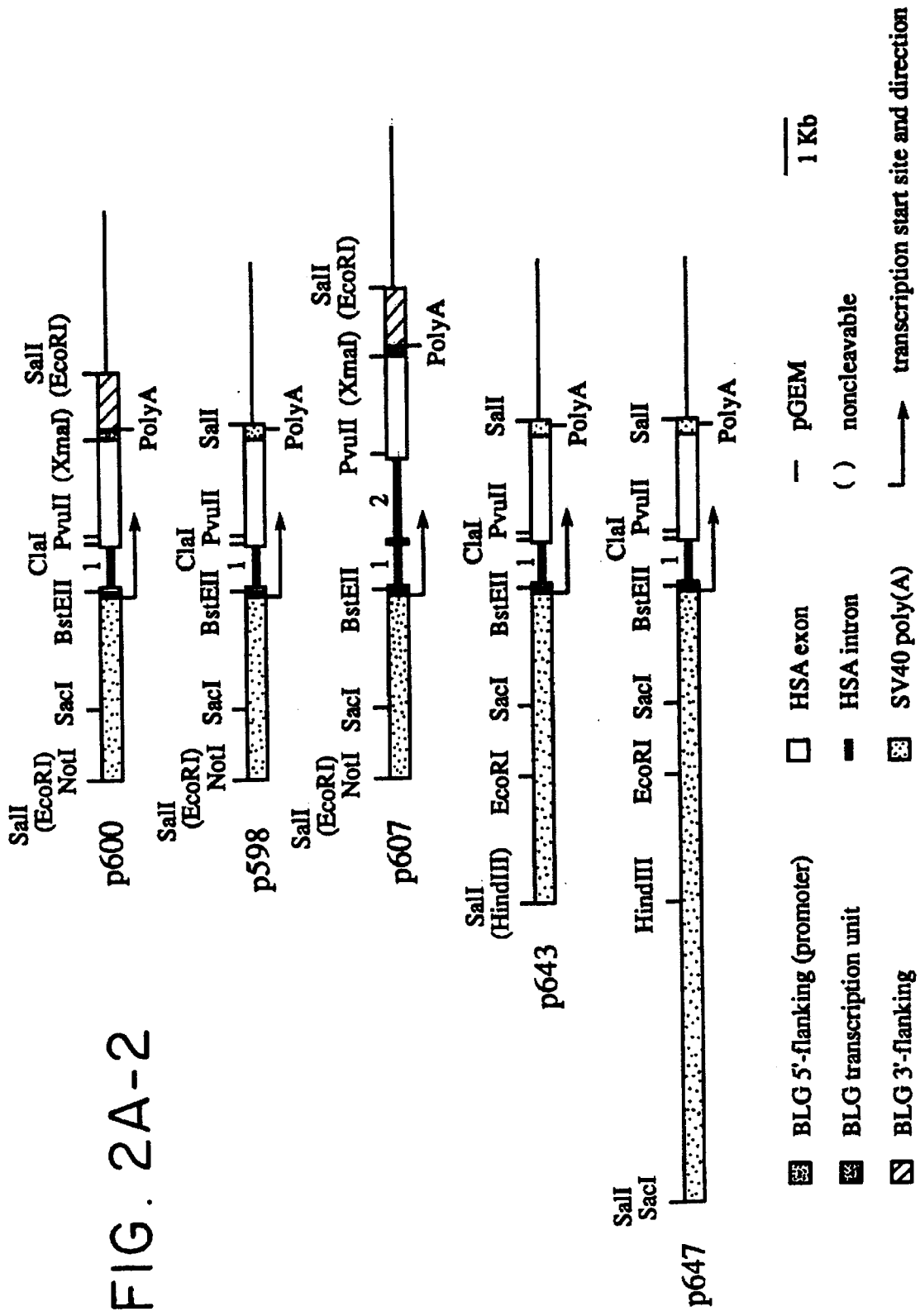
FIG. 2 is a graphical depiction of the DNA constructs.

The DNA sequence of the naturally occurring HSA gene has been determined. FIG. 1 demonstrates a map of the HSA gene and its sequence [SEQ ID NO:36].

Figures 1, 2B:
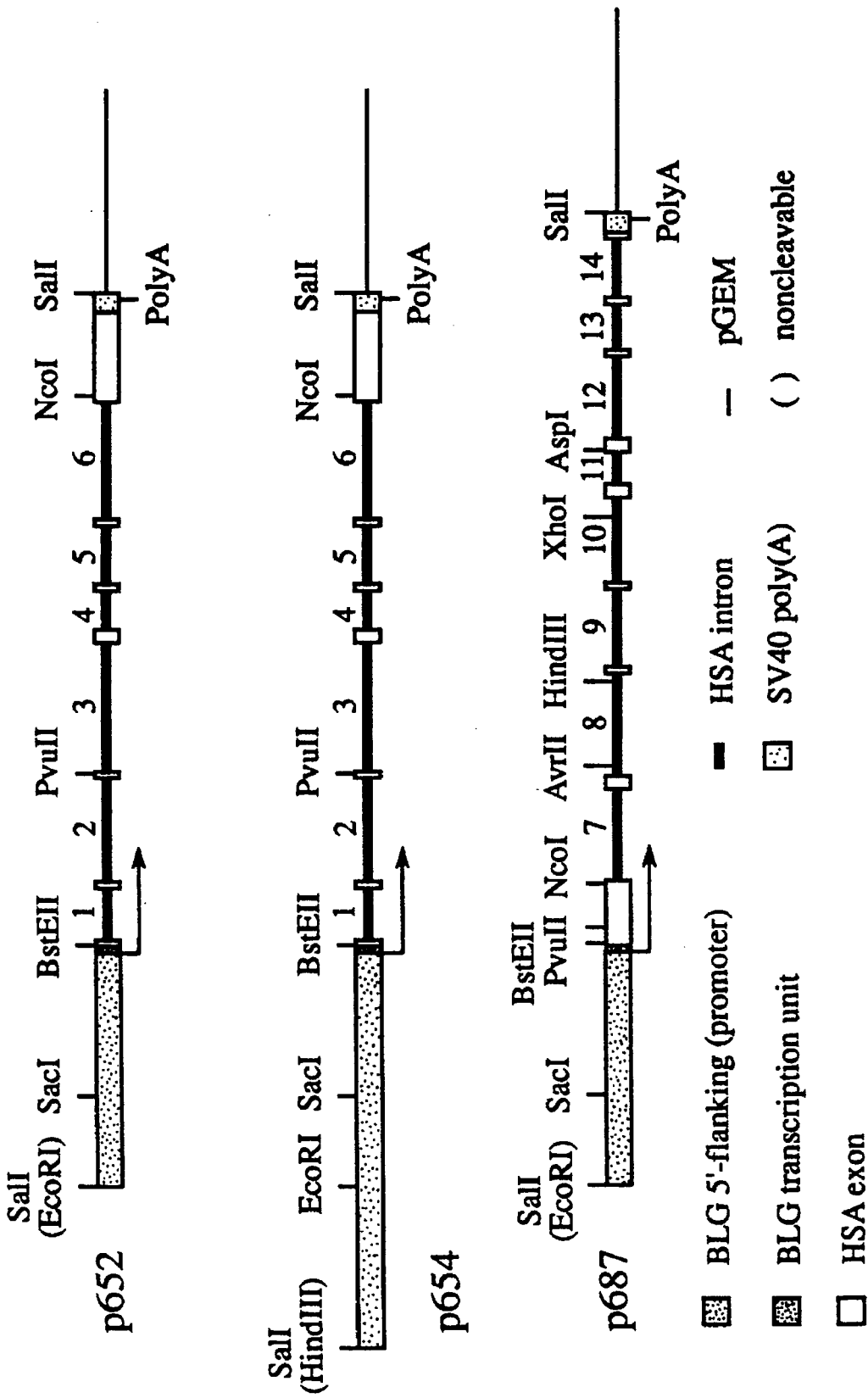
Figures 2, 2B:
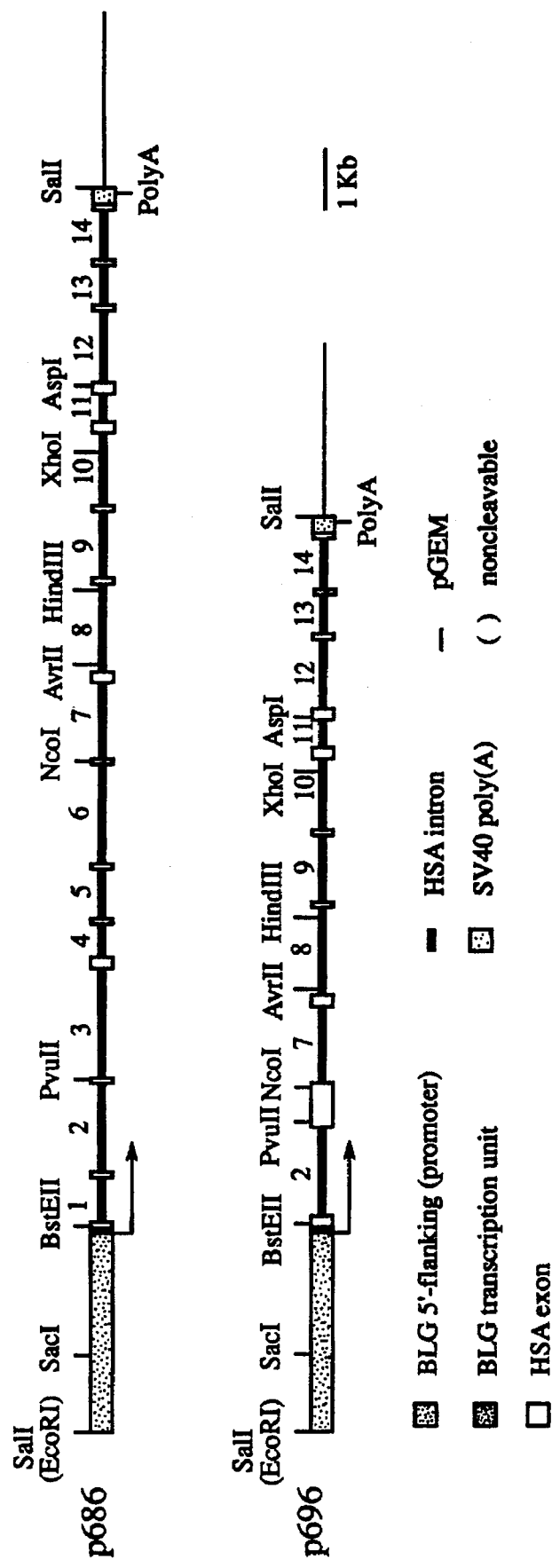

In order to make the DNA constructs of the present invention several different approaches were required. The ovine BLG gene was cloned from high molecular weight liver DNA as two EcoRI subgenomic fragments (5'-half approximately 4.3 kb and 3'-half approximately 4.4 kb) into the EcoRI site of lambda gt10 vector. The two halves were subcloned into pGEM-I, joined together at their EcoRI sites within the transcriptional unit, by using adaptor oligonucleotides which destroyed the EcoRI sites at the gene's 5'- and 3'-ends and which introduced SaII sites at these positions. A unique SnaBI site was introduced into the PvuII site within the 5'-untranslated region of exon 1. This results in vector p585 for the expression of β-lactoglobulin and contains approximately 3 kb of 5'-flanking promoter sequences. Constructs are represented in FIGS. 2A and 2B. The BLG 5'-flanking sequences were extended by cloning from ovine liver DNA a HindIII subgenomic fragment extending from the HindIII site within the transcriptional unit upstream approximately 8 kb to a 5'-HindIII site (p644 and p643) or a SacI subgenomic fragment extending from the SacI site within the original 5'-flanking sequences upstream approximately 8.6 kb to another SacI site (p646 and p647). The former constructs include approximately 5.5 kb of 5'-flanking promoter sequences. The latter construct includes approximately 10.8 kb of these sequences.

An HSA cDNA was isolated from a lambda gt11-human liver cDNA library. The cDNA contains the complete HSA coding sequence including the prepropeptide sequences as well as 20 bp of 5'-untranslated and 141 bp of 3'-untranslated sequence. The HSA cDNA was inserted into the PvuII site within the untranslated region of BLG exon 1 in the same orientation as the BLG coding sequence resulting in vector p575. A DNA fragment encompassing the HSA genomic sequence including part of exon 1, intron 1, exon 2, intron 2 and part of exon 3 was produced by PCR using a 5'-oligonucleotide primer which overlaps the native BstEII site in exon 1 and 3'α-oligonucleotide primer which overlaps the native PvuII site in HSA exon 3 using high molecular weight DNA purified from human lymphocytes as a template. The cDNA region between the BstEII site in exon 1 encoding region and the PvuII site in exon 3 encoding region was replaced with the corresponding genomic fragment (2401 bp) from the PCR product. This resulted in an HSA minigene possessing introns 1 and 2 in their native locations, as included in vector p607. In order to introduce the first intron of the HSA gene into the HSA cDNA we first introduced a ClaI site into the region of the HSA cDNA which is derived from HSA exon 2 by replacing a G with an A in the third base position of the codon for the 34th amino acid of the HSA protein including the prepropeptide, by in vitro mutagenesis. The altered codon encodes arginine as did the original. HSA intron 1 DNA with flanking exon sequences was generated by PCR using a 5'-oligonucleotide primer which overlaps the native BstEII site in exon 1 and a 3'-oligonucleotide primer which overlaps, and contains, the ClaI site introduced into exon 2 encoding DNA. A clone of the genomic PCR product containing exon 1 through exon 3 sequences was used as template for PCR generation of intron 1 and flanking sequences. The cDNA region between the native BstEII site in exon 1 encoding region and the introduced ClaI site in exon 2 encoding region was replaced with the corresponding genomic fragment from the PCR product. The resulting HSA minigene possesses intron 1 in its native location as included in vectors p599, p600, p598, p643 and p647.

The deletion of the BLG coding sequence was accomplished by deleting sequences between the introduced SnaBI site within the 5'-untranslated region of BLG exon 1 and the native XmaI site within the 3'-untranslated region of BLG exon 7 prior to introduction of HSA sequences, as seen in vectors p600 and p607. This vector maintains most of the untranslated BLG exon 7 including its polyadenylation signal and site as well as sequences 3' of the BLG transcription unit. The SV40 early gene (T and t) polyadenylation signal and site downstream of HSA sequences in vectors p598, p643 and p647 as well as other vectors was obtained from SV40 DNA by restriction with BclI at its 5'-end (SV40 map position 2770) and BamHI at its 3'-end (SV40 map position 2533). In these vectors all BLG sequences downstream of the introduced SnaBI site in the 5'-untranslated BLG exon 1 including coding sequence, polyadenylation signal and site and 3'-flanking sequences were deleted.

In order to obtain HSA introns 3–14, the HSA gene was cloned from human placental DNA. Three NcoI sites within the HSA gene sequence were identified. The first NcoI site lies about 275 base pairs upstream of HSA exon 1. The second site lies within exon 7 and the third site lies about 227 base pairs downstream of exon 15. Digestion of human high molecular DNA with NcoI released two fragments of 8079 and 9374 base pairs which together encompass the entire HSA gene. The 8079 base pair fragment represents the 5'-half of the HSA gene while the 9374 base pair fragment represents the 3'-half of the gene. These fragments were used to make 2 separate subgenomic DNA libraries. HSA clones from these libraries were identified using an HSA cDNA probe. A clone containing the 5'- half of the HSA gene to exon 7 was designated p650. A clone (p651) identified as containing sequences of the 3'-half of the HSA gene were found to have an internal deletion of HSA sequences. Clone p651, did, however, contain HSA sequences extending from the AspI site within HSA exon 12 through the NcoI site downstream of HSA exon 15.

In order to clone the HSA gene sequences between exon 7 and exon 12 so as to obtain that region which includes introns 7–11, PCR technology was utilized. Four PCR reactions were set up using synthetic priming oligonucleotides homologous to desired regions of the HSA gene containing useful restriction sites. The PCR reactions were designed so that the upstream end of reaction #1 overlapped the NcoI site within exon 7. The downstream end of reaction #1 overlapped the AvrII site within intron 8. This same AvrII site was overlapped by the upstream end of PCR reaction #2. The downstream end of PCR reaction #2 overlapped the HindIII site within intron 8. This HindIII site was also overlapped by the upstream end of PCR reaction #3. The downstream end of PCR reaction #3 overlapped the XhoI site in intron 10 which was also overlapped by the upstream end of PCR reaction #4. The downstream end of PCR reaction #4 overlapped the AspI site in exon 12. By this PCR strategy the entire region desired was obtained and adjacent PCR products were joined together using overlapped restriction sites. The products of PCR #1 and #2 reactions were ligated together at their common AvrII site within HSA intron 8 and cloned into plasmid pGEM-1 resulting in construct p679. This construct contains HSA sequences extending from the NcoI site in exon 7 to the HindIII site in the downstream end of intron 8. The product of PCR #3 and #4 reactions were ligated together at their common XhoI site within HSA intron 10 and cloned into plasmid pGEM-2 resulting in construct p676. This construct contains HSA sequences extending from the same HindIII site in the downstream end of intron 8 to the AspI site in exon 12.

When taken together with construct p650, containing the HSA gene sequences from the NcoI site upstream of HSA exon 1 (HSA gene base pair position 1462) to the NcoI site in exon 7 (HSA gene base pair position 9541) and construct p651, containing HSA gene sequences extending from upstream of the AspI site in exon 12 (HSA gene base pair position 15592) to the NcoI site downstream of exon 15 (HSA gene base pair position 18915) these constructs, p679 and p676, complete the cloning of the entire HSA gene.

In order to assess the contribution of introns to the level of expression of HSA in the milk of transgenic animals, constructs comprising the HSA exons and various combinations of introns were constructed. Details of the various constructions are given in the examples which follow.

The constructs of the present invention were tested for their ability to support expression of HSA protein in vitro in tissue culture cells and in vivo in transgenic animals. The in vitro expression of HSA by the constructs of the present invention is described in detail in Example 11. The natural in vivo regulation of expression of milk proteins under the control of the native promoters (e.g., BLG) is complex and requires the influence of hormones and specific cell-cell interactions. The BLG promoter is not usually active in tissue culture cells. In order to drive expression in the COS-7 cells chosen for these in vitro tests, an SV40 enhancer was introduced within the BLG promoter. Details of the construction of the constructs of the present invention having the SV40 enhancer are given in Example 11. A transient assay for HSA expression in COS-7 cells was used to test the constructs. Briefly, constructs of the present invention were transfected into COS-7 cells, incubated for 48–72 hours. Expression of HSA was determined by metabolically labeling de novo synthesized proteins with $^{35}S$-methionine and immunoprecipitating labeled HSA protein, which had been secreted into the media supernatants, with HSA specific antibodies. Precipitated HSA was analyzed by SDS-PAGE and HSA bands detected by fluorography.

Figure 3A:
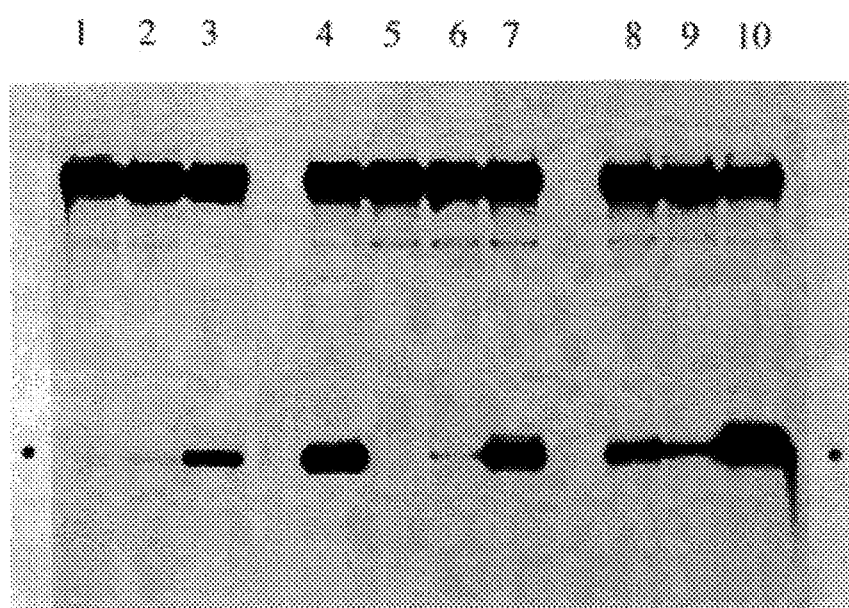
FIG. 3 demonstrates fluorograph of SDS PAGE from in vitro expression analysis.
Figure 3B:
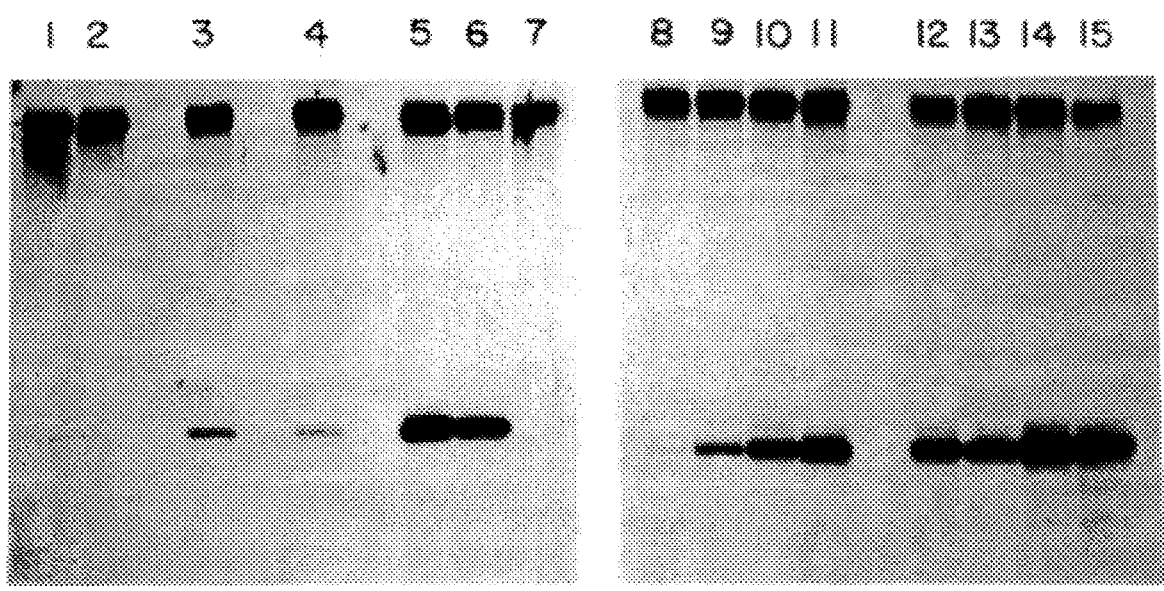

COS-7 cells transfected with a construct which contained HSA cDNA, lacking introns, (p658) expressed HSA at low levels. Expression of HSA protein was also relatively low even when some of the introns were included in the construct. However, selection of certain combinations of introns [p656 (introns 1–6), [p684 (introns 7–14)], [p695 (introns 2+12–14)], [p697(introns 1+2+12–14)], [p693 (introns 1+7–14)], [p692 (introns 2+7–14)] and [p698 (introns 1+2+ 7–14)] supported expression of HSA protein at levels equal to or even greater than the full length HSA gene [p685 (introns 1–14; full length)]. In vitro analyses are shown in FIGS. 3A and 3B and summarized in Table 1.

TABLE 1

| In Vitro Construct | HSA Introns Included | Level of In Vitro Expression | Homologous In Vivo Construct | In Vivo Expression in Transgenic Milk |
|---|---|---|---|---|
| p615 | 0 (cDNA) (BLG coding seq.) (BLG 3'-seq.) | 1 | p575 (BLG coding seq.) (BLG 3'-seq.) | 0/8 |
| p608 | 1 | 2 | p598 | See below |
| p606 | 1 (BLG 3'-seq.) | 2 | p600 (BLG 3'-seq.) | 0/6 |
|  |  |  | p599 (BLG coding seq.) (BLG 3'-seq.) | 0/5 |
| p610 | 1 & 2 (BLG 3'-seq.) | 3 | p607 (BLG 3'-seq.) | 4/6 (1–35 μg/ml) |
| *p658 | 0 (cDNA) | 1 |  |  |
| *p659 | 1 | 2 | p598 | 1/5 (2.5 mg/ml) |
|  |  |  | p643 (5.5 kb BLG 5'-seq.) | 0/2 |
|  |  |  | p 647 (10.8 kb BLG 5'-seq.) | 1/8 (2 μg/ml) |

TABLE 1-continued

| In Vitro Construct | HSA Introns Included | Level of In Vitro Expression | Homologous In Vivo Construct | In Vivo Expression in Transgenic Milk |
|---|---|---|---|---|
| *p691 | 2 | 3 | | |
| *p660 | 1 & 2 | 3 | p607 (BLG 3'-seq.) | see above |
| *p656 | 1 – 6 | 6 | p652 | 8/8 (0.02–6.5 mg/ml) 5 (Not yet determ.) |
| | | | p654 (5.5 kb BLG 5'-seq.) | 4/6 low (Not yet quant.) |
| *p682 | 12 – 14 | 2 | p688 | In progress |
| *p684 | 7 – 14 | 6 | p687 | 2 (Not yet determ.) |
| *p685 | 1 – 14 | 6 | p686 | 1 (Not yet determ.) |
| *p694 | 1 + 12 – 14 | 4 | | |
| *p695 | 2 + 12 – 14 | 5 | | |
| *p697 | 1 + 2 + 12 – 14 | 7 | | |
| *p693 | 1 + 7 – 14 | 6 | | |
| *p692 | 2 + 7 – 14 | 8 | p696 | |
| *p698 | 1 + 2 + 7 – 14 | 8 | | |

In vitro constructs marked with (*) vary only in presence of HSA introns. (BLG 5'-sequences, SV40 enhancer and 3'-SV40 poly(A) are the same) Except where indicated constructs lack the BLG coding sequences and BLG 3'-sequences including poly(A). Unless indicated the SV40 poly(A) site was utilized. Unless indicated the 3 kb BLG 5'-flanking sequences (promoter) were utilized.
In vitro expression level ranges 1 (low expression) to 8 (high expression) are semiquantitative comparisons where each increment represents several fold to many fold differences in level of expression.
"Not yet determ." means that transgenic produced but presence of HSA in milk not yet determined. "Not yet quant." means that expression of HSA in the milk of the transgenic has been shown but the amount not yet quantitated.

Expression of HSA in tissue culture cells from these constructs demonstrated that the level of expression of HSA is modulated by the specific complement of HSA introns, i.e., the number of HSA introns present in the construct, the specific introns incorporated, the relative locations of introns, and the synergies between specific introns. Several fold higher levels of expression are obtained with constructs containing HSA minigenes with specific subsets of introns as compared with the entire HSA gene with all of its introns. Levels of expression of HSA are particularly high when supported by HSA minigenes which comprise one but not all of the first 7 introns of the HSA gene and one of the last 7 introns of the HSA gene. There are 5 Alu sequences (family of repeated DNA sequences) within HSA introns. Three of these Alu sequences are located within the first 7 introns and 2 are located within the last 7 introns. Intron 2 has 2 Alu sequences, introns 7, 8, and 11 each have 1 Alu sequence. There appears to be an association between the presence of the Alu sequences within introns and the introns' positive effect on resultant levels of expression obtained with HSA minigenes.

In vivo expression of heterologous protein in transgenic animals by the constructs of the present invention was assessed by injecting the constructs of the present invention into murine oocytes to produce transgenic mice. Transgenic mice were produced following the general methods described by Hogan et al., "Manipulating the mouse embryo: a laboratory manual" CSHL (1986). The details are further described in Example 12. Two different heterologous proteins, BLG and HSA, were expressed in the milk of the transgenic mice. Mice carrying the BLG or the BLG/HSA constructs of the present invention were detected by analysis of somatic DNA from the tails of newborn mice utilizing a $^{32}$p DNA probe which recognizes both BLG and HSA DNA sequences. Details of the assay are described in Example 12. In contrast to the in vitro assay, no enhancer was needed to drive the expression of proteins under the direction of the BLG promoter. Female mice that were determined to carry the construct of the present invention, when mature were mated to non-transgenic males. Milk was collected from nursing transgenic females after parturition and the milk analyzed for the presence and amount of heterologous protein (BLG or HSA). Founder male transgenic mice were bred to non-transgenic females to produce female offspring to test for the expression of heterologous proteins in their milk. Heterologous protein expressed in milk was detected by a dot assay using antibodies to BLG or HSA protein. BLG expression in milk was detected by spotting the milk sample onto a nitro-cellulose filter. Anti-BLG antibodies were then contacted with the filter. $^{125}$I-Protein A was then contacted with the filter to bind quantitatively to the bound antibodies. HSA expression in milk was detected by spotting the milk sample onto a nitrocellulose filter. Iodinated anti-HSA monoclonal antibodies were then contacted with the filter. The radioactivity was determined by autoradiography and correlated with standards by densitometry of the autoradiographs to quantitate the amount of heterologous protein expressed in the transgenic milk.

The capability of the BLG promoter to promote expression of BLG and HSA was tested both in vitro and in vivo. A 3kb DNA fragment containing of the 5'-flanking region of the BLG gene was utilized in most of the constructs of the present invention. The efficacy of this 3 kb promoter was tested by making transgenic mice utilizing construct p585 which contain the BLG gene under the control of the 3kb BLG promoter.

Figure 4:
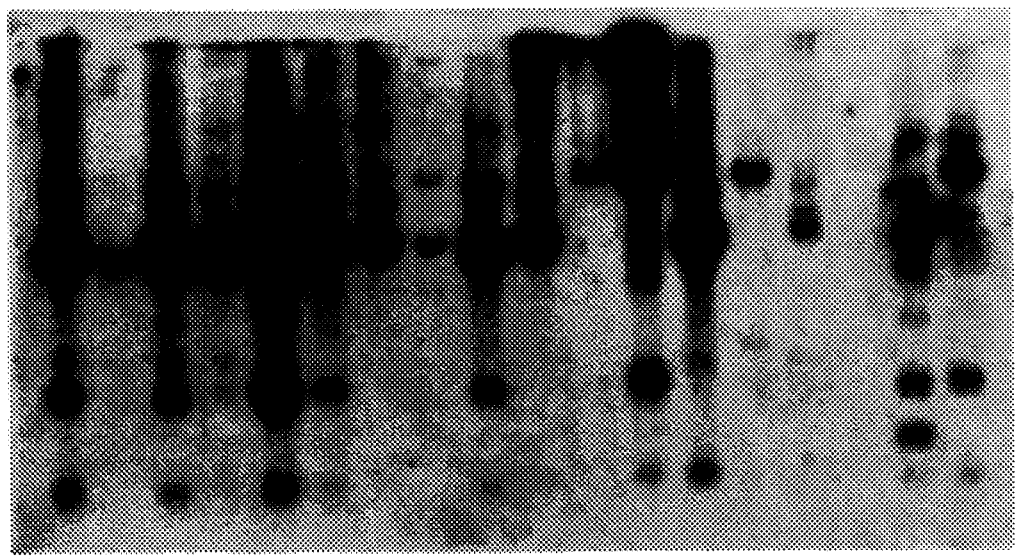
FIG. 4 demonstrates a Southern blot analysis of transgenic mice carrying HSA constructs.

All transgenic mouse strains produced, carrying the native sheep BLG gene (construct p585), expressed BLG at high levels in the mammary gland and milk as determined by dot blot. An example is shown in FIG. 4. Levels ranged from 1 to 8.5 mg/ml BLG (see Table 2). This is somewhat lower than the range (3–23 mg/ml) found by Simons et al. (1987, Nature 328:530–532) utilizing 4.3 kb BLG 5'-flanking sequences. However, no increase in BLG expression was observed with 5'-flanking sequences of 5.5 kb (construct p644) or 10.8 kb (p646). These results demonstrate that the BLG 3kb 5'-flanking sequences in the constructs of the present invention contain all the 5'-control elements necessary to direct high level expression to the mammary gland.

This 3 kb BLG promoter fragment was also used in constructs comprising all or parts of the HSA DNA. This 3 kb fragment proved sufficient to promote BLG and HSA expression both in vitro and in vivo.

The milks of lactating females from transgenic lines produced from BLG/HSA constructs were analyzed for the presence of HSA by immuno-dot blot using iodinated anti-HSA monoclonal antibodies. An example is shown in FIG. 5A. Our initial attempt to produce transgenic mice expressing HSA in their milk was by introducing the HSA cDNA into the 5'-untranslated region of the first exon of the BLG gene of vector p585, resulting in vector p575. None of the 8 lines secreted detectable levels of the human protein (Table 2). It appeared that although our BLG vector was able to drive expression of its own BLG gene, it was unable to support the expression of the inserted HSA cDNA. Others have found that in transgenics, the levels of expression of heterologous genes under the control of a variety of 5'-regulatory elements (promoters) were increased by the incorporation of introns into the heterologous transcripts. Therefore, we tested a series of vectors in which the sheep BLG promoter was fused to HSA minigenes containing a variety of intron combinations.

Analysis of expression from one HSA minigene, containing HSA intron 1, within 3 constructs (p599, p600, p598) demonstrated only 1 transgenic line (#23) out of 16 produced expressing detectable levels of HSA in its milk. Inclusion of HSA intron 1 alone in the constructs of the present invention is not sufficient to obtain a high percentage of transgenic lines which express. As shown on FIG. 5B, female mice of line 23 secrete high levels, greater than 2 mg/ml of HSA into their milk, and have stably transmitted this ability to their progeny for over a year.

Mouse milk contains a significant amount of endogenous mouse serum albumin which co-migrates with human serum albumin in SDS-PAGE gels (data not shown). Immunodetection assays demonstrated that the anti-HSA monoclonal antibody specifically detected the human protein and not the mouse protein. The human and mouse proteins were also distinguishable by their distinct electrophoretic mobilities on native polyacrylamide gels. Milk from expressing line 23 clearly contains both the human (low mobility) and mouse (high mobility) albumins as seen by generalized protein staining with coomassie (FIG. 6). The lower mobility band was confirmed to be HSA by native gel and immunoblot analysis (FIG. 6).

The secreted HSA protein behaves in a manner indistinguishable from purified HSA or the HSA found in human milk in its electrophoretic mobility through native gels as well as in denaturing gels. In native gels the human protein migrates with a different mobility from endogenous mouse serum albumin.

Reproducible expression of HSA in the milk of transgenics was achieved first only when the first 2 HSA introns were included in the construct (p607) with 4 of the 6 transgenic lines examined expressing HSA in their milk. Although an improvement in the frequency of expressing transgenics (penetrance), the levels of expression were disappointingly low (1–35 ug/ml).

A major improvement in both the number of transgenics which express HSA in their milk (penetrance) as well as the levels expressed resulted from the inclusion of the first 6 introns into the HSA minigene of the transgenic construct (p652). All eight strains produced from p652 and thus far analyzed for the expression of HSA in fact express HSA. In addition, two of these strains express high levels of HSA above 1 mg/ml, with one strain expressing between 6–7 ug/ml.

The overall in vivo results correlate with the in vitro expression results. That is, extremely low levels of HSA are expressed from the cDNA construct in vitro and no HSA is detectably expressed from the cDNA construct in vivo in transgenics. The inclusion of intron 1 into the in vitro construct results in slightly higher levels of in vitro expression as compared with the cDNA construct. Similarly, one transgenic strain derived from the transgenic constructs with HSA intron 1 did express. The inclusion of introns 1 and 2 in vitro also resulted in higher expression than the cDNA. These two introns in transgenics resulted in a much better penetrance then either intron 1 or the cDNA. The inclusion of the first 6 introns within the in vitro construct resulted in a markedly higher level of expression. This correlated with both the high penetrance of the intron 1–6 transgenic construct as well as the high levels expressed in resultant strains. A continued correlation between in vitro and in vivo results would demonstrate that some intron combinations, such as, 2+7–14, results in very high levels of expression of HSA in the milk of transgenics, even higher than can be achieved using the entire HSA gene with all of its introns. The production of transgenic goats (Example 13) with constructs demonstrated to express high levels of HSA in the milk of transgenic mice or with constructs which are the transgenic counterparts of the in vitro constructs which support very high levels of HSA, results in very high levels of expression in the milk of these dairy animals.

In order to examine the tissue specificity of expression of HSA RNA total RNA was isolated from various tissues of transgenic female mice on day 10–12 of lactation. RNAs were fractionated by electrophoresis, transferred to nylon membrane and probed with a $^{32}$P-labeled HSA antisense RNA as described in Example 12.

High levels of HSA mRNA were detected in the mammary gland of lactating females which secrete HSA into their milk (strain 23) (FIG. 7). Transcripts are also found in skeletal muscle but not in any of the other tissues tested (spleen, heart, kidney, lung, liver and brain). This ectopic expression of transgene transcripts is not associated with any apparent physiological abnormality. Transgene transcripts from other genes fused to the 5'-flanking sequences of the genes of milk specific proteins have been shown to accumulate in non-mammary tissues such as salivary gland, kidney and brain.

Figure 8A:
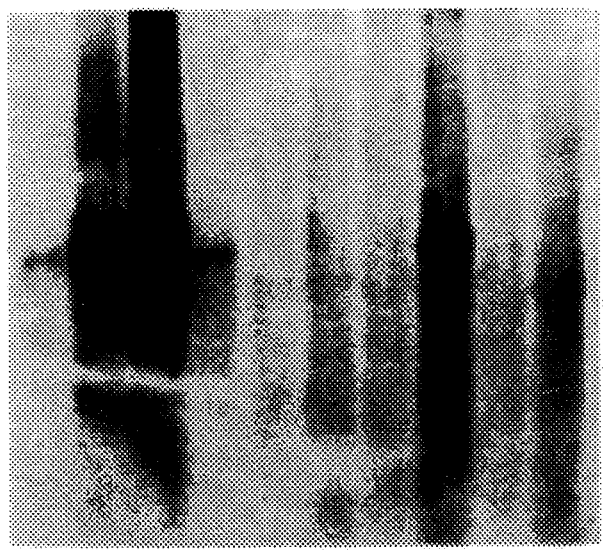
FIG. 8 demonstrates an HSA RNA analysis (Northern) of tissues of transgenic animals.
Figure 8B:
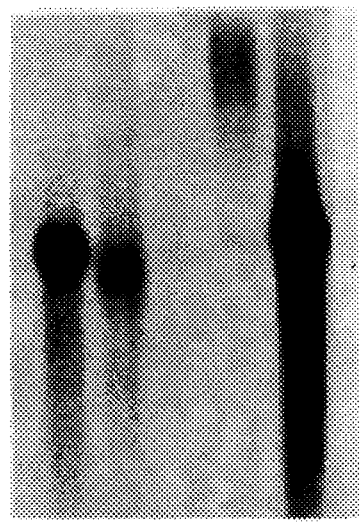

The expression of HSA in RNA in the mammary tissue of transgenic strain #23 was also demonstrated by in situ hybridization as described in Example 12 and shown in FIG. 8.

Figure 9:
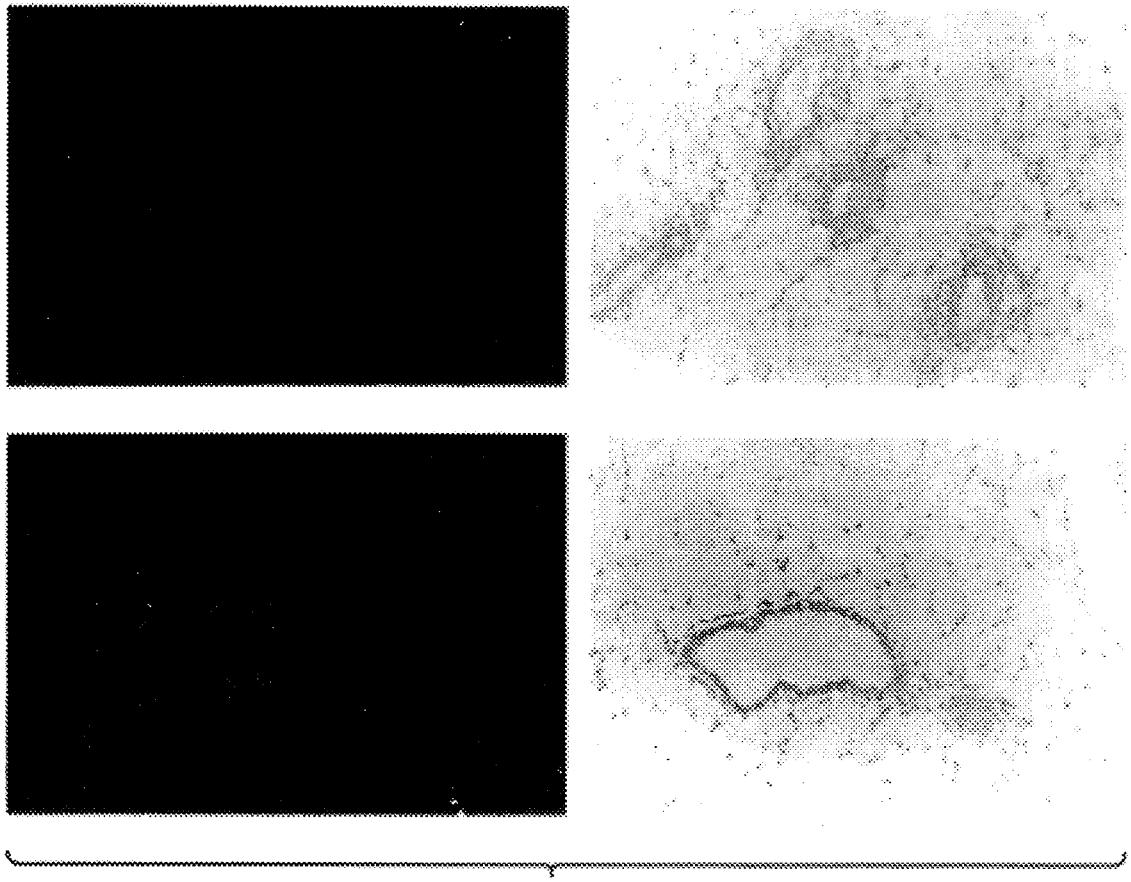
FIG. 9 demonstrates in situ detection of HSA RNA.

The screening of transgenic mice for their expression of HSA in their milk was standardly performed on the milk of lactating females following parturition. The expression of HSA from explant cultures of mammary glands of both virgin and lactating transgenic strain #23 was also demonstrated (Example 13 and FIG. 9). Assay of explant culture of mammary tissue of transgenic goats greatly facilitates the identification of expressing transgenic animals.

Having now generally described the invention, a more complete understanding can be obtained by reference to the following specific examples. These examples are provided for the purpose of illustration only and are not intended to be limiting unless otherwise specified.

EXAMPLE 1

A. CLONING OF THE SHEEP β-LACTOGLOBULIN GENE WITH 5' AND 3'-FLANKING REGIONS (λ22-1, λ10-1)

A restriction map of the sheep β-lactoglobulin (BLG) gene (Simons et al., 1988, Bio/Technology 6; 179–183) indicated that the transcribed BLG sequences possessed only one EcoRI site and that EcoRI sites existed about 3 Kb upstream of the transcription region within 5'-flanking sequences and about 1 Kb downstream of the transcription unit within 3'-flanking sequences. Restriction digestion of the BLG gene and flanking regions would therefore release 2 BLG gene fragments; (1) a fragment (approximately 4.1–4.2 Kb) made up of 5'-flanking sequences, including the BLG promoter, and the first part of the BLG transcription unit (designated 5'-region) and (2) a fragment (approximately 4.4 Kb) composed of the rest of the transcription unit including the polyadenylation site and 3'-flanking sequence (designated 3'-region). Therefore, the BLG gene and flanking regions were cloned as two gene halves made up of these two EcoRI subgenomic fragments.

High molecular weight sheep liver DNA was digested extensively with the restriction enzyme EcoRI. Restriction fragments were resolved on a 0.6% agarose gel along with size marker DNA standards. In order to identify the location of the BLG fragments on the gel, an analytical vertical strip of gel, made up of the size markers and about 5% of the restricted sheep DNA was cut from the rest of the gel, stained with Ethidium Bromide (EtBr) and photographed under UV light. The rest of the gel, the preparative portion, was wrapped in plastic wrap and put at 4° C. until ready for use. The analytical portion of the gel was subjected to Southern analysis using a $^{32}$P-labeled probe produced by the random primer method, with a bovine BLG cDNA as template. The bovine cDNA clone used as probe was kindly supplied by Dr. Carl A. Batt, Cornell University. Only a single band was detected of molecular weight of approximately 4.3 Kb. This single band represents both the 4.1 and 4.4 EcoRI subgenomic fragments which comigrated in this gel system. This comigration was verified in other Southern gel analyses using 4.1 and 4.4 Kb specific probes. The corresponding region of the preparative gel containing the BLG fragments was cut out of the agarose gel. DNA was electroeluted from this gel piece, purified by Eluptip-d (Schleicher and Schuell) (i.e. gel and elutip purified) and ethanol precipitated.

In order to isolate and clone the BLG fragments, the purified subgenomic DNA eluted from the gel was ligated into a Stratagene lambda-gt10 vector which had been previously digested with EcoRI and dephosphorylated. Ligation products were packaged with Gigapack plus extracts (Stratagene) and approximately 500,000 plaques of the resultant subgenomic library plated out on C600 cells (Stratagene) and incubated for plaque formation. Plates were lifted, in duplicate, onto nitrocellulose filters and treated by standard procedures. Filters were subsequently baked, prehybridized (5× SSPE, 1/25 Blotto, 0.2% SDS) and hybridized with the same buffer containing $^{32}$P-bovine BLG cDNA probe at 62° C. overnight. Filters were washed, the last most stringent wash was with 1×SSC, 0.2% SDS at 62° C. Filters were subsequently subjected to autoradiography. Several duplicate positive plaques were identified and subplaqued to purity in Y1088 cells. Clones which contained either the 5'-region or the 3'-region of BLG were identified by differential hybridization with either BLG exon 2 and 5'-probes or exon 5 and 3'-probes, respectively. A clone possessing the 5'-region (5'-clone), designated λ22-1, as well as a clone possessing the 3'-region (3'-clone), designated λ10-1 were utilized for subsequent subclonings.

B. SUBCLONING BLG 5' AND 3' REGIONS FROM λ22-1 and λ10-1 PHAGE INTO pGEM-1 PLASMID (p570, p568)

Recombinant phage (λ22-1 and λ10-1) and DNA were purified using LambdaSorb® (Promega) using their protocols. Cloned BLG, DNA were released from recombinant phage DNA by digestion with EcoRI. The released BLG 5'-region (approximately 4.1–4.2 Kb) from λ22-1 DNA and BLG 3'-region (approximately 4.4 Kb) from λ10-1 DNA were elutip purified and ethanol precipitated.

Plasmid vector, pGEM-1, was prepared for the subcloning of the BLG 5'-region by digestion with PvuII and EcoRI, and the large vector fragment was gel and elutip purified and ethanol precipitated. A cloning adapter was prepared by the annealing of two synthetic oligonucleotides as shown.

```
       SalI              (EcoRI)
5' GTCGACGCGGCCGC            3' [SEQ ID NO:1]
3' CAGCTGCGCCGGCGTTA         5' [SEQ ID NO:2]
```
(NOTE: Sites in parenthesis are not cleavable.)

The adapter was designed to allow the EcoRI compatible end to ligate to either of the EcoRI ends of the BLG 5'-region insert and by doing so to destroy the EcoRI site at that ligation junction, as the adapter sequence varied from an authentic EcoRI sequence by the incorporation of a G following the 5'-AATT instead of a C as would be found in the authentic sequence. Further, the adapter would link the adjoined BLG 5'-region to the PvuII site of the prepared pGEM-1 vector by ligation of the blunt PvuII site and blunt end of the adapter. A BLG EcoRI end which did not ligate to an adapter was free to ligate to the EcoRI site of the prepared pGEM-1 vector. The prepared pGEM-1 vector, the BLG 5'-region insert fragment and the adapter were ligated in one step. The BLG DNA could ligate between the adapter and plasmid EcoRI sites in either of its two orientations. Ligation products were transformed into *E. coli* DH5 cells to ampicillin resistance. Resistant bacterial colonies were analyzed for the presence of plasmid containing BLG inserts by Whatman 541 filter lifts and hybridization with $^{32}$P-labeled BLG exon 2 and 5' probes. Positive colonies were selected and grown in LB-amp medium. Plasmid DNAs were prepared from these isolates. Restriction analysis of clones with BamHI allowed for the selection of clones containing the desired orientation of BLG insert. Bam HI digestion of plasmids with the desired BLG orientation resulted in DNA fragments of approximately 4200 and 2800 bp while DNA fragments from the non-desired orientation were approximately 5800 and 1380 bp. Restriction analysis confirmed that the desired clone contains the BLG 5'-region between the PvuII and EcoRI sites of pGEM-1. The blunt end of the adapter is adjacent to the pGEM-1 PvuII site. The PvuII site is no longer cleavable at this location of the final clone. The 5'-end of the BLG 5'-region is linked to the Eco RI compatible region of the adapter. This EcoRI site is destroyed by the ligation. A SalI site had been introduced with the adapter, just upstream of the 5'-end of the BLG region. This site is not found within either the BLG 5' or 3'-regions. The EcoRI site of the 3'-end of the BLG 5'-region linked to the pGEM-1 EcoRI site is regenerated and available for later ligation to the 5'-end of the BLG 3'-region. The desired correct BLG 5'-region construct (clone) selected for further work was designated p570. Clones with the BLG sequences in the undesired orientation were designated p571 and utilized in later constructions.

The EcoRI restricted, purified 4.4 Kb BLG 3'-region DNA was subcloned into plasmid pGEM-1 between the plasmid BamHI and EcoRI restriction sites. pGEM-1 digested with BamHI and EcoRI was gel and elutip purified, and ethanol precipitated. A cloning adapter made from two annealed synthetic oligonucleotides had the following sequence;

```
   (EcoRI)              BamHI
5' AATTAGCGGCCGCG           3' [SEQ ID NO:3]
3'     TCGCCGGCGCCTAG       5' [SEQ ID NO:4]
```

As with the previous adapter, it's EcoRI compatible end allowed for ligation with either of the EcoRI ends of the BLG 3'-region but resulted in loss of the EcoRI site. In this case the adapter EcoRI compatible site was followed by a T/A bp as opposed to a G/C bp as would be found in an authentic EcoRI sequence. A three part ligation with prepared pGEM-1 (Bam HI and EcoRI ends), the adapter (Bam HI and EcoRI compatible ends), and the BLG 3'-region insert (EcoRI ends) was performed. The Bam HI site of the adapter should ligate to the Bam HI site of pGEM-1. The BLG 3'-region would ligate between the adapter EcoRI compatible site and the EcoRI site of pGEM-1 in either orientation. Ligation products were introduced into *E. coli* DH5 cells by transformation to ampicillin resistance. Clones with the desired BLG 3'-region orientation were characterized by Bam HI generated fragments of approximately 4500, 2000 and 800 bp. Restriction analysis of desired clones confirmed that the EcoRI site at the 5'-end of the BLG 3'-region was ligated to the EcoRI site of pGEM-1 and that this regenerated the EcoRI site; the EcoRI site at the 3'-end of the BLG 3'-region was ligated to the EcoRI compatible site of the adapter resulting in the destruction of this EcoRI site; the ligated BamHI sites of the adapter and pGEM-1 had regenerated a Bam site; and that the SalI site of the pGEM-1 polylinker was just downstream of the BLG 3'-region (and adapter). The EcoRI site at the 5'-end of the BLG 3'-region would be used later to join together the two BLG gene halves. A desired clone, designated p568, was selected for further work.

C. CONSTRUCTION OF A COMPLETE BLG VECTOR WITH A SnaBI SITE REPLACING THE PVU II IN BLG EXON 1 (p585 vector)

In order to facilitate the cloning of foreign genes (such as HSA) into the correct PvuII site of the BLG vector (within the untranslated portion of BLG exon 1), a SnaB1 site was introduced into this PvuII site. No SnaB1 site exists within natural BLG sequences or in the pGEM bacterial plasmid sequences in which the BLG sequences are cloned. Therefore, the introduced SnaBI site is unique, simplifying the introduction of foreign genes into the appropriate location of the BLG sequences.

The 5' portion of the BLG gene (EcoRI subgenomic) cloned into pGEM-1 (i.e. plasmid p570) possesses three PvuII sites including the appropriate site within BLG exon 1. The other two PvuII sites were mapped to locations approximately 2100 bp and 2600 bp, respectively, upstream of the PvuII site within exon 1. Plasmid p570 was partially digested with PvuII and linearized plasmid (approximately 7200 bp) was gel and elutip purified. A synthetic SnaBI linker oligonucleotide of the sequence 5'-GTACGTAC-3' was self annealed. Annealed linker was ligated with the purified linearized plasmid p570. Ligation products were transformed into *E. coli* DH5 cells to ampicillin resistance. Desired recombinants were identified by the presence of a SnaBI site, the absence of the PvuII site in exon 1 and the presence of the two upstream PvuII sites. The correct plasmid was designated p583.

The 5'-half of the BLG gene with the SnaBI site replacing the PvuII in exon 1 was recombined with the 3'-half of the BLG gene as follows. Construct p583 (containing the 5'-BLG region) was digested with PvuI (within pGEM-1 ) and EcoRI (at the junction of the 3' end of the 5' BLG region and the adjacent pGEM-1) The DNA fragment (approximately 5800 bp) containing the 3'-portion of the plasmid Amp resistance gene, the plasmid ori and the 5'-portion of the BLG gene was gel and elutip purified and ethanol precipitated.

The plasmid containing the 3'-half of the BLG gene, p568, was similarly digested with Pvu1 and EcoRI. The DNA fragment of approximately 5800 bp containing pGEM-1 sequences including the 5'-portion of the Amp resistance gene up to its PvuI site and complementary to those in the fragment described above, and the 3'-half of the BLG gene up to its 5' EcoRI junction with pGEM was gel and elutip purified and ethanol precipitated. The two purified fragments were ligated together and transformed into *E. coli* DH5 cells to ampicillin resistance. Only correctly recombined fragments would regenerate a complete ampicillin resistance gene. Correct recombination of a complete BLG gene was confirmed by restriction analysis by the release of the full length BLG region of approximately 8800 bp with restriction enzyme SalII. This new plasmid, designated p585, is composed of a pGEM-1 bacterial plasmid and the complete BLG gene as described, with a SnaBI site substituting for the PvuII site in exon 1 of BLG.

D. CLONING OF SHEEP GENOMIC SEQUENCES EXTENDING UPSTREAM OF THE 5'-BLG SEQUENCES IN PREVIOUS BLG VECTORS (p639, p642)

The 5'-sequences, upstream of the BLG coding sequence, within the previously discussed BLG vectors encompass a genomic DNA fragment of approximately 3 Kb. This 3 Kb region includes the BLG promoter sequences. In order to determine if sequences upstream of this 3 Kb fragment contain elements which would increase the consistency and/or level of expression from the BLG promoter, upstream genomic sequences were cloned.

High molecular weight sheep liver DNA was subjected to Southern analysis utilizing a variety of restriction enzymes. The very 5'-end of the BLG sequences already obtained, i.e. the SalI to Pvu II fragment (approximately 450 bp) hybridized to repetitive sequences in genomic Southerns. Therefore, the PvuII-PvuII fragment (approximately 500 bp) downstream of the SalI-PvuII fragment and the PvuII-BamHI fragment (approximately 600 bp) downstream of the PvuII-PvuII fragment were used as probes. These probe fragments were generated by digestion of p570 with BamHI and PvuII, gel and elutip purification of the appropriate 500 and 600 bp fragments, and ethanol precipitation. Probe DNA was $^{32}$P-labeled by the random primer technique.

Southern analysis revealed a probe positive HindIII fragment (approximately 8 Kb) and a probe positive SacI fragment (approximately 8.6 Kb). This allowed us to map Hind III and SacI sites to approximately 2.5 Kb and 7.8 Kb, respectively, upstream of the 5'-end (EcoRI site) of the previously obtained BLG sequences.

High molecular weight sheep DNA was digested extensively with either SacI or HindIII. Restriction fragments were resolved on 0.6% agarose gels. An analytical strip of each gel, made up of size markers and about 5% of the restricted sheep DNA was cut from the rest of the gel, stained with ethidium bromide and photographed under UV light. The rest of the gels, the preparative portions, were wrapped in plastic wrap and put at 4° C. until ready for use. The analytical portions were subjected to Southern analysis using the $^{32}$P-labeled probe discussed above. The probe positive HindIII, 8 kb and SacI, 8.6 Kb fragments were identified. Corresponding regions were cut out of the preparative portions of the gels. DNAs were electroeluted, elutip isolated and ethanol precipitated.

Vector Lambda Zap II (Stratagene) was used for construction of subgenomic libraries for both the HindIII and SacI generated fragments. For the Sac I subgenomic library, Lambda Zap II was digested with SacI and dephosphorylated with CIP. For the HindIII subgenomic library, Lambda Zap II was first self ligated in order to ligate cos ends together. It was subsequently digested with SpeI and partially filled in with Klenow polymerase and dCTP and dTTP.

The purified Hind III subgenomic DNA was partially filled with Klenow polymerase and dGTP and dATP. These partially filled HindIII ends were compatible with the partially filled Lambda Zap II SpeI ends. The HindIII subgenomic DNA was ligated into the SpeI digested λ vector and the SacI subgenomic DNA was ligated into the SacI digested λvector. Each was packaged with Gigapack Plus II extracts (Stratagene) and plated on PLK-A cells (Stratagene). Plates were lifted, in duplicate, onto nitrocellulose filters. Filters were treated as discussed in the library screen for λ22-1 and λ10-1. Filters were hybridized with the $^{32}$P-labeled probe discussed earlier in this section. Filters were washed. Duplicate positive plaques were subplaqued to purity with the final, most stringent wash being with 0.5× SSC, 0.2%SDS, 62° C. The pBlueScript SK phagemid containing BLG sequences were in vivo excised from the Lambda Zap II positives clones using R408 helper phage (Stratagene) by the method recommended by the supplier. The phagemids were rescued on XL1-Blue cells (Stratagene) and selected on LB-ampicillin plates. Selected colonies were cultured in LB-ampicillin medium and plasmids from these cultures were subjected to restriction analysis.

Correct clones of the Hind III subgenomic cloning were initially identified by the presence of an approximate 4.4 Kb EcoRI fragment and approximately 1900 and 1075 bp Asp718 (isoschizomer of KpnI) fragments all of which had been previously delineated by mapping of the BLG region already cloned. Both orientations of the BLG HindIII subgenomic fragment cloned into the SpeI site of the vector were found. The desired orientation with the 5'-end of BLG HindIII fragment cloned into the SpeI site towards the plasmid multiple cloning SalI site was characterized by the release of a fragment of approximately 2500 bp upon digestion with EcoRI and HindIII. This desired clone of the HindIII subgenomic DNA was designated p639. The 5'-end of the BLG region was extended approximately 2.5 Kb further upstream from the 5'-end of the original BLG clone (e.g. p585).

Correct clones of the SacI subgenomic cloning were initially identified by the release of a fragment of approximately 2500 bp upon digestion with EcoRI and HindIII and a 3800 bp fragment upon digestion with SacI and HindIII. The clones with the desired orientation of BLG sequences within the pBlueScript SK plasmid were identified as follows. SacI subgenomic clones were digested with EcoRI and subjected to Southern analysis using the $^{32}$P-labeled p570 Bam HI/PvuII probe homologous to the 5'-end of the p570 BLG sequences and therefore to the 3'-end of the BLG sequences within the SacI subgenomic fragment described above. A probe positive EcoRI fragment of approximately 4.2 Kb identified the plasmid as being the desired orientation with the upstream most end of the SacI fragment being next to the plasmid multiple cloning site including the SalI site. This correct, desired clone was designated p642.

Sequencing confirmed that p639 (HindIII subgenomic) and p642 (SacI subgenomic) contained BLG upstream sequences which overlapped the original BLG clones (e.g., p571 ). The 5'-sequence of the original BLG 5'-portion cloned in p571 was determined using an Sp6 promoter primer of the sequence, 5' ATTTAGGTGACACTATA 3' [SEQ ID NO:5]. The sequence was further extended into the BLG sequences of p571 by using a primer, 5'TGTTTGGG-GACTTCCCTGGTGA [SEQ ID NO:6] derived from sequence obtained using the Sp6 promoter primer.

The sequences obtained using the second primer were identical in the p571, p639 and p642 construction confirming that the latter two clones contained BLG upstream sequences. In addition a third primer, 3' AGTCCCACTAC-GACCGGAG [SEQ ID NO:7] 5', derived from sequence obtained from the Sp6 promoter primer was used to obtain sequence upstream of the 5'- EcoRI site in the original BLG clone. As expected sequences obtained from both p639 and p642 were identical and the proximal most 25 bases were identical with the 5'-most bases of p571 and contained the natural EcoRI site.

E. CONSTRUCTION OF COMPLETE BLG VECTORS WITH BLG CODING REGIONS WITH EXTENDED 5'-SEQUENCES (p644, p646)

The 5"-extended BLG sequences cloned as HindIII and SacI sheep DNA subgenomics in plasmids p639 and p642, respectively, were incorporated into full length vectors capable of expressing BLG as follows.

For the incorporation of sequences contained within the HindIII fragment, the 5'-extension was first recombined with the 5'-BLG region in plasmid p590. p590 was digested to completion with Asp718 and partially with SalI. The DNA fragment of approximately 4940 bp which included BLG sequences downstream of the Asp718 site through the SalI site and adjacent pGEM sequences was and elutip purified and ethanol precipitated. The 5'-end of the BLG HindIII fragment (approximately 4600 bp) was released from p639 by digestion with SalI (in the polylinker, just upstream of the 5'-end of the Hind III fragment), and Asp 718 (downstream of the original BLG 5'-Eco RI site), gel purified, electroeluted, elutip isolated and ethanol precipitated. The prepared p590 and p639 fragments were ligated together. Ligation products were transformed into *E. coli* DH5 cells to ampicillin resistance. Correct recombinants were diagnosed by the fact that restriction by EcoRI produced two fragments (approximately 7090 and 2500 bp), SalI produced two fragments (approximately 6758 and 2835 bp ) and BglII linearized plasmid to the size of approximately 9590 bp. Correct clones were designated p640. Plasmid p640 contains a BLG 5'-region of approximately 5.5 Kb from the upstream Hind III site to the transcriptional initiation site just upstream of the SnaBI cloning site. This 5.5 Kb 5'-region was recombined with complete BLG coding and 3'-regions. Plasmid p640 was digested with PvuI (within the pGEM) and SnaBI releasing a DNA fragment of approximately 7043 bp made up of part of the pGEM vector and the 5.5 Kb BLG 5-region. Plasmid p585 was also digested with PvuI and SnaBI releasing a DNA fragment (approximately 7041 bp) comprised of the rest of pGEM and the BLG coding and 3'-regions. These fragments were gel and elutip purified and ethanol precipitated and subsequently ligated together. Ligation products were used to transform DH5 cells and positive transformants selected on LB-ampicillin plates. HindIII digestion resulting in 3 DNA fragments (approximately 7840, 3410 and 2830 bp) identified correct recombinant clones consisting of 5'-BLG sequences (approximately 5.5 Kb), BLG coding sequences and 3'-BLG sequences. Correct clones were designated p644.

The 5'-BLG sequences contained within the sheep DNA SacI clone, p642, were incorporated into a full length BLG vector by first joining these sequences to the 5'-BLG sequences contained within plasmid p640 which possesses 5'-BLG sequences derived from the HindIII clone p642. Plasmid p640 was digested with EcoRV which restricted it at 2 sites. One EcoRV site was contained within the pGEM polylinker just upstream of the 5'-end of the HindIII BLG sequences. The second EcoRV site was just upstream of the original 5'-BLG EcoRI site. The resultant DNA fragment of approximately 7150 bp was gel and elutip purified and ethanol precipitated. The ends of this fragment were then dephosphorylated with calf intestinal alkaline phosphatase (CIP) (Promega). Into this dephosphorylated EcoRV site was ligated BLG sequences which extended from the common EcoRV site just upstream of the original 5'-EcoRI site up to the EcoRV site. This latter DNA fragment (approximately 7700 bp) was obtained by digestion of p642 with EcoRV and subsequent gel and elutip purification and ethanol precipitation. Ligation products were transformed into DH5 cells and positive transformants selected on LB-ampicillin plates. Clones with the correct, desired orientation of the p642 insert into p640 were characterized by the presence of two BgIII DNA fragments (approximately 10,140 and 4710 bp). A BgIII site had been mapped to about 600 bp downstream of the 5'-Sac I site by Southern analysis of sheep DNA. Correct clones were designated p645. p645 clones contain 5'-BLG sequences of approximately 10.8 Kb upstream of the BLG transcriptional initiation site, followed by the SnaBI site, the 3'-BLG region containing the native BLG polyadenylation signal and site and the pGEM bacterial plasmid. p645 does not contain BLG coding sequence. p645 was used to produce a full length BLG vector with 10.8 Kb 5'-BLG sequences. p645 was digested with SnaBI and PvuI (within pGEM). The DNA fragment of approximately 12,290 bp, made up of bacterial plasmid sequences as well as all 10.8 Kb 5'-sequences upstream of the SnaBI site, was gel and elutip purified and ethanol precipitated. The BLG coding sequence and BLG 3'-sequences as well as bacterial plasmid were obtained as a SnaBI, PvuI DNA fragment (approximately 7040 bp) from p585 similarly prepared by gel purification. These two DNAs were ligated together and transformed into E. coli DH5 cells to ampicillin resistance. Correct recombinants produced DNA fragments of approximately 14,040, 2860 and 2430 bp upon XbaI digestion and were designated p646.

EXAMPLE 2

CLONING THE HUMAN SERUM ALBUMIN (HSA) GENE (p650, p651)

The DNA sequence of the HSA gene was determined by Minghetti et al. (J. Biol. Chemistry 261; 6747–6757, 1986) and entered into the NIH nucleic acid sequence data bank GenBank 67. Three NcoI sites within this sequence were identified using the SEQ-Sequence Analysis Systems program of IntelliGenetics, Inc. The first NcoI site lies about 275 bp upstream of HSA exon 1. The second site lies within exon 7 and the third site lies about 227 bp downstream of exon 15. Therefore, digestion of human high molecular DNA with NcoI should release two fragments of 8079 and 9374 bp which together encompass the entire HSA gene. The 8079 bp fragment represents the 5'-half of the HSA gene while the 9374 bp fragment represents the 3'-half of the gene. The strategy to clone out the gene was to digest human DNA with NcoI, to make 2 separate subgenomic libraries from DNAs of the approximate sizes of the 2 expected HSA fragments and to identify HSA clones from these libraries.

High molecular weight human placental DNA was digested extensively with NcoI. Restriction fragments were resolved on a 0.6% agarose gel along with size marker DNA standards. An analytical vertical strip of the gel, made up of the size markers and about 5% of the restricted human DNA was cut from the rest of the gel, stained with ethidium bromide and photographed under UV light. The rest of the gel, the preparative portion, was wrapped in plastic wrap and put at 4° C. until ready for use. The analytical portion of the gel was subjected to Southern analysis using digoxigenin-dUTP labeled HSA cDNA probe produced by the random primer method according to protocols supplied with the Genius System DNA Labeling Kit (Boehringer Mannheim). The substrate DNA for the production of the probe was the HSA cDNA sequence released from plasmid pHSA-F1⁻ (see below) by digestion with SalII and EcoRI. Detection of probe positive bands of correct size (approximately 8079 and 9374 bp) in the Southern analysis were identified using the Genius Nucleic Acid Detection Kit (Boehringer Mannheim), Lumi-Phos 530 (Boehringer Mannheim) and autoradiography according to manufacturers instructions. The individual corresponding regions of these HSA fragments were cut out of the preparative part of the agarose gel. DNA was electro-eluted elutip purified and ethanol precipitated.

The 2 purified NcoI subgenomic fractions were individually ligated into Lambda ZapII vector, digested with EcoRI and dephosphorylated with alkaline phosphatase (Stratagene, Inc.) using 2 synthetic oligonucleotides which when annealed form an adaptor of the structure:

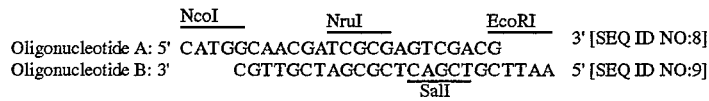

```
                    NcoI           NruI         EcoRI
Oligonucleotide A: 5' CATGGCAACGATCGCGAGTCGACG       3' [SEQ ID NO:8]
Oligonucleotide B: 3'     CGTTGCTAGCGCTCAGCTGCTTAA   5' [SEQ ID NO:9]
                                        SalI
```

Prior to annealing the 5'-end of oligonucleotide B was phosphorylated using T4 polynucleotide kinase by standard procedures, so as to supply a 5'-phosphate group required for the ligation of the EcoRI site of the adaptor to the dephosphorylated EcoRI site of the lambda vector. The 5'-phosphate group of the NcoI site of the subgenomic human DNA fractions allows ligation of this site to the unphosphorylated NcoI site of the adaptor. Ligation products were packaged into phage using Gigapack II Plus packaging extract (Stratagene, Inc.) according to the suppliers protocols.

Libraries were produced by the adsorption of packaged phage into PLK-A cells (Stratagene, Inc.) and plated. Approximately 100,000 plaques of the library produced from the NcoI subgenomic fraction containing the HSA 8079 bp fragment and 50,000 plaques of the library produced from the NcoI subgenomic fraction containing the HSA 9374 bp fragment. Plates were lifted in duplicate onto nitrocellulose filters. Filters were treated by standard procedures, prehybridized (5× SSPE, ½₅ Blotto, 0.2% SDS) and hybridized overnight at 62° C. with the same buffer containing the ³²P-labeled HSA cDNA probe discussed above. Filters were washed and subjected to autoradiography. Duplicate positive plaques were identified and subplaqued to purity. The pBluescript SK plasmid component of the Lambda ZapII vector, containing HSA gene inserts, were in vivo excised from the vector using the R408 helper phase supplied by Stratagene, Inc. according to their protocols. Plasmids containing the 5'-half of the HSA gene were designated p651. Plasmids containing the 3'-half of the HSA gene were designated p650.

Restriction analysis of p650 confirmed that this clone in fact represented the insertion of the NcoI 5'-half of the HSA gene into the EcoRI site of pBluescript SK. Digestion of p650 with the following restriction enzymes yielded the expected DNA fragments.

| Restriction Enzyme | Expected & Observed DNA Fragments (bp) |
|---|---|
| BgIII | 5363; 4921; 754; 47 |
| BstEII | 11085 |
| EcoRI | 3541; 2958; 2008; 1603; 709; 266 |
| HindIII | 6564; 4281; 240 |
| NcoI | 8079; 3006 |
| NcoI + BstEII | 7756; 3006; 323 |
| ScaI | 2511; 2449; 2405; 2368; 1352 |
| XbaI | 6926; 1882; 1296; 981 |

The expected locations of the restriction sites were derived from a restriction map of pBluescript SK (Stratagene, Inc.) and the SEQ restriction analysis program of Intelligenetics, Inc. of the sequence of the appropriate region of the HSA gene as published by Minghetti et. al. 1986, J. Biol. Chem. 216:6747–6757. The restriction analysis of p650 also determined that the HSA gene region was cloned into the pBluescript vector with its 5'-end toward KpnI site of the vector multiple cloning site.

It had been expected that the restriction of p651 with NcoI would result in 2 fragments of 9374 and 3006 bp; the former representing the NcoI 3'-half of the HSA gene and the latter representing the pBluescript sequences into which the HSA sequences were cloned. However, while the 3006 bp (pBluescript) band was visible, the 9374 bp band was not found. Instead a band of approximately 4000 bp was present. In order to determine whether this band represented HSA sequences, p651 was subjected to sequencing using several sequencing primers (synthesized in house) using either the Sequenase Sequencing kit (United States Biochemical Corp.) or the T7Sequencing kit (Pharmacia) according to manufacturer's protocols. The EcoRI site within pBluescript into which the cloned sequences were introduced is flanked by a T7 promoter on one side and a T3 promoter on the other side. We therefore used T7 (sense) and T3 (antisense) sequencing primers in order to sequence the termini of the cloned sequences. HSA exon 7,8,9 and 11 specific primers (sense) as well as two exon 12 specific primers (sense) and an exon 15 specific primer (antisense) were also used. Primer sequences were as follows:

| Primer | Sequence obtained from primer corresponding to HSA gene bp position and region | |
|---|---|---|
| T7 | 9540–9737 | (Part of exon 7 and into intron 7) |
| T3 | 18919–18669 | (3'-flanking region of exon 15 and into exon 15) |
| HSA exon 7 | 9605–9616 | (Intron 7) |
| HSA exon 12(A) | 15681–15690 | (Exon 12) |
| HSA exon 12(B) | 15796–15807 | (Intron 12) |
| HSA exon 15 | 18497–18156 | (Intron 14) |

Clearly, the 5'- and 3'-ends of the 3'-half of the HSA gene, including NcoI sites at each end, as well as exon 7 and at least part of intron 7 from the 5'-end and the 3'-sequences flanking exon 15 and exon 15 through exon 12 from the 3'-end. These results demonstrate that the 3'-half of the HSA gene was present in p651, but that an internal deletion of HSA sequences had occurred. The deletion was also found in the parent Lambda phage. Therefore, construct p651 contains the HSA gene from exon 12 through exon 15 and beyond into 3'-flanking sequences to the NcoI site, including introns 12, 13 and 14. Restriction analysis of p651 demonstrated that the AspI site within exon 12 was present.

In order to clone the HSA gene sequences between exon 7 and exon 12 so as to obtain that region which includes introns 7–11, we utilized PCR technology. Four PCR reactions were set up using synthetic priming oligonucleotides homologous to desired regions of the HSA gene containing useful restriction sites. The PCR reactions were designed so that the upstream end of reaction #1 overlapped the NcoI site within exon 7. The downstream end of reaction #1 overlapped the AvrII site within intron 8. This same AvrII site was overlapped by the upstream end of PCR reaction #2. The downstream end of PCR reaction #2 overlapped the HindIII site within intron 8. This HindIII site was also overlapped by the upstream end of PCR reaction #3. The downstream end of PCR reaction #3 overlapped the XhoI site in intron #10 which was also overlapped by the upstream end of PCR reaction #4. The downstream end of PCR

| Primer | Sequence | Corresponding HSA gene bp position# |
|---|---|---|
| T7 | 5' AATACGACTCACTATAG 3' [SEQ ID NO: 10] | |
| T3 | 3' GAAATCACTCCAATTA 5' [SEQ ID NO: 11] | |
| HSA Exon 7 | 5' CATGGAGATCTGCTTGAA 3' [SEQ ID NO: 12] | 9541–9558 |
| HSA Exon 8 | 5' GACTTGCCTTCATTAGCT 3' [SEQ ID NO: 13] | 10996–11013 |
| HSA Exon 9 | 5' GAGAAGTGCTGTGCCGCT 3' [SEQ ID NO: 14] | 12566–12583 |
| HSA Exon 11 | 5' GTACCCCAAGTGTCAACT 3' [SEQ ID NO: 15] | 15002–15019 |
| HSA Exon 12(A) | 5' GACAGAGTCACCAAATGC 3' [SEQ ID NO: 16] | 15588–15605 |
| HSA Exon 12 (B) | 5' GAGAGACAAATCAAGAAAC 3' [SEQ ID NO: 17] | 15735–15753 |
| HSA Exon 15 | 3' AGTCGGATGGTACTCTTATTCTC 5' [SEQ ID NO: 18] | 18522–18544 |

Specific sequence information from all primers except the HSA exon 8,9 and 11 specific primers was obtained suggesting that these latter regions were lacking in p651. Sequences obtained from sequencing reactions using the primers corresponded to HSA gene sequences as indicated below.

reaction #4 overlapped the AspI site i,n exon 12. By this PCR strategy the entire region desired would be obtained and adjacent PCR products would be joined together using overlapped restriction sites. PCR primers and reactions are as follows;

PCR #1

```
                    BamHI    Nco
Sense primer  5'  GAATTCGGATCCCCATGGAGATCTGCTTGAATGTGCT  3' [SEQ ID NO:19]
                         *                          *
                        9540                       9564
```

```
                              AvrII
Antisense      3'  TGTTGAATCCTCCTATCGGATCCCAGCTG  5' [SEQ ID NO:20]
primer              *                     *
                  11127                 11149
```

PCR #2

```
                        AvrII
Sense primer  5'  GTCGACCCTAGGCTTTTCTGTGGAGTTGCT  3' [SEQ ID NO:21]
                         *                    *
                       11144                11167
```

```
                             HindIII
Antisense      3'  TTCAGGAATCGATGATTCGAACTTAAG  5' [SEQ ID NO:22]
primer              *                  *
                  12339              12359
```

PCR #3

```
                       HindIII
Sense primer  5'  GAATTCAAGCTTTACTGCATGGGGTTTAGT  3' [SEQ ID NO:23]
                        *                     *
                      12354                 12377
```

```
                                XhoI
Antisense      3'  TGTTCTGTATCAAAGAAAGGAGCTCCAGCTG  5' [SEQ ID NO:24]
primer              *                       *
                  14454                   14478
```

PCR #4

```
                        XhoI
Sense primer  5'  GTCGACCTCGAGTAGATTAAAGTCATACA  3' [SEQ ID NO:25]
                         *                   *
                       14473               14495
```

```
                        AspI      BamHI
Antisense      3'  TTGCGGTCATTCACTGTCTCAGCCTAGGCTTAAG  5' [SEQ ID NO:26]
primer              *              *
                  15575          15596
```

Note
Restriction sites in bold are found within HSA sequences. Non-HSA sequences are shown as small letters. Astoricks and associated numbers mark the corresponding HSA gene bp position.

PCR reactions were performed with high molecular weight human placental DNA as substrate [40 cycles of 94° C. (1', 30"), 60° C. (2'), 72° C. (4')]. A sample of each reaction was analyzed on a 1% agarose gel. DNA bands of expected size (PCR #1, 1628 bp; PCR #2, 1228 bp; PCR #3, 2136 bp; PCR #4, 1142 bp) were seen. The remainder of the reactions were extracted two times with chloroform, 2 times with phenol/chloroform, 2 times with chloroform and subsequently ethanol precipitated. Products of reactions #1 and #2 were digested with AvrII. Products of reactions #3 and #4 were digested with XhoI. DNAs were subjected to agarose gel electrophoresis and DNA bands cut from the gel, electroeluted and elutip purified. The purified products of reactions #1 and #2 were ligated together and products of reactions #3 and #4 were ligated together. Since each PCR product had available 5'-phosphates only at their digested ends (AvrII or XhoI) only these ends were available for ligation and the other end of each DNA was not available for ligation. Ligation products of reactions #1 and #2 as well as ligation products of reactions #3 and #4 were subsequently each digested with BamHI and HindIII. The resultant 2814 bp DNA representing the ligation of reactions #1 and #2 at their common AvrII site with a digested BamHI site at its upstream terminus and a digested HindIII site at its downstream terminus was gel and elutip purified. This DNA was ligated into the BamHI and HindIII sites of plasmid vector pGEM-1. The 3243 bp DNA representing the ligation of reactions #3 and #4 at their common XhoI sites, with its upstream terminus digested at its HindIII site and downstream terminus digested at its BamHI site was similarly purified and ligated into the HindIII and BamHI sites of plasmid vector pGEM-2. Ligation products were introduced into MC1061 bacterial host cells by electroporation (BTX Electroporation System 600) according to manufacturer's protocols. Positive transformants were selected on L-ampicillin plates. Restriction analysis of DNAs from selected transformants identified desired clones. Construct p679 was the designation of the HSA PCR #1 and #2 products cloned into pGEM-1. It contains HSA sequences extending from the NcoI site in exon 7 (HSA gene bp position 9541) to the HindIII site in the downstream end of intron 8 (HSA gene bp position 12355). The pGEM-2 construct containing HSA PCR #3 and #4 products was designated p676. It contains HSA sequences extending from the same HindIII site in the downstream end of intron 8 (HSA gene bp position 12355) to the AspI site in exon 12 (HSA gene bp position 15592).

When taken together with construct p650, containing the HSA gene sequences from the NcoI site upstream of HSA exon 1 (HSA gene bp position 1462) to the NcoI site in exon 7 (HSA gene bp position 9541) and construct p651, containing HSA gene sequences extending from upstream of the AspI site in exon 12 (HSA gene bp position 15592) to the NcoI site downstream of exon 15 (HSA gene bp position 18915) these constructs, p679 and p676, complete the cloning of the entire HSA gene.

EXAMPLE 3

COMPLETE BLG VECTOR WITH THE HSA cDNA UNDER THE CONTROL OF THE BLG PROMOTER (p575)

Vectors based upon use of the BLG promoter and gene system incorporate the foreign gene to be expressed (HSA) into the PvuII site of the BLG gene within exon 1 just upstream of the BLG translational initiation ATG codon. There are a number of PvuII sites within the BLG sequences. The BLG 5'-region cloned into pGEM-1 (i.e. plasmid p570) possesses three PvuII sites including the appropriate site within BLG exon 1. The other two PvuII sites were located approximately 2100 and 2600 bp, respectively, upstream of the PvuII site within exon 1. In order to introduce the HSA cDNA into the appropriate PvuII site of a complete BLG vector, the cDNA was first cloned into the correct site within the BLG 5'-clone (p570) and subsequently the BLG 5'-clone with HSA cDNA was join to the BLG 3'-clone. Plasmid, p570, was partially digested with PvuII. Linearized plasmid (approximately 7200 bp) was recovered by gel and elutip purification and ethanol precipitation.

The HSA cDNA was isolated from a lambda gt11-human liver cDNA library. The complete cDNA clone is 1,983 bp in length and contains the complete HSA coding sequences, including the 18 amino acid prepeptide, the 6 amino acid propeptide, and the 585 amino acids of the mature protein. The cDNA clone also contains 20 bp of 5'-untranslated and 141 bp of 3'-untranslated sequence. The cDNA clone was subcloned into the plasmid vector pBS(-) (Stratagene) between the vector BamHI and EcoRI polylinker restriction sites with the BamHI site at its 5'-end and EcoRI site at its 3'-end. This plasmid was referred to as pHSA-F1$^-$. The HSA cDNA sequence was released from the bacterial vector by restriction with BamHI and EcoRI. These staggered ends were blunted with Klenow polymerase in the presence of excess dNTPs. The blunt ended HSA cDNA was ligated into the purified PvuII linearized plasmid p570 discussed earlier. Ligation products were introduced into DH5 cells by transformation to ampicillin resistance. Desired recombinants were diagnosed by the presence of two Hind III restriction fragments (approximately 7807 and 1293 bp) and three Bam HI restriction fragments (approximately 4280, 3170, and 1700 bp). This confirmed that the HSA cDNA was introduced into desired PvuII site of BLG, in exon 1, in the same orientation as the BLG coding sequence and that the junction between the BLG PvuII site and the Klenow blunted 5'-HSA Bam HI site regenerated a functional Bam HI site. Additional analyses verified that the junction between the 3'-HSA EcoRI site blunted with Klenow polymerase and the BLG PvuII had regenerated a function EcoRI site. This correct plasmid clone was designated p572.

The 5'-region of the BLG gene with the HSA cDNA cloned into its PvuII site in exon 1 was recombined with the 3'-region of the BLG gene as follows. Construct p572 was digested to completion with PvuI (within pGEM) and partially with EcoRI. The desired fragment of approximately 7800 bp containing pGEM sequences and the 5'-region of the BLG gene to the junction of its 3'-end (EcoRI) with the pGEM-1 was gel and elutip purified and ethanol precipitated. This was ligated to the 3'-region of the BLG gene, released from plasmid p568, as a PvuI/EcoRI fragment of approximately 5800 bp. This latter fragment contains pGEM-1 sequences up to its PvuI site, and the 3'-region of the BLG gene up to its 5'-junction (EcoRI) with pGEM. Ligation products were used to transform DH5 cells to ampicillin resistance.

Correct, desired recombinants were characterized by HindIII fragments of approximately 7840, 3500 and 2200 bp and BamHI fragments of approximately 4760, 4244, 2000, 1700 and 870 bp. Correct recombinants were designated p575. These represent the complete BLG sequences utilized in the vectors including 5' and 3' regions, with the HSA cDNA introduced into the BLG PvuII site just upstream of the BLG ATG translational initiation codon, in the same orientation as the BLG coding sequences, within a pGEM plasmid. BLG/HSA and HSA/BLG junctions were confirmed by sequence analysis. The BLG/HSA sequences are flanked by Sal I sites.

As Sal I sites are not found anywhere else in the BLG/HSA sequences, digestion of p575 with SalII produces a BLG/HSA fragment, from the pGEM, suitable for injection into mammalian oocytes for the production of BLG/HSA transgenics.

EXAMPLE 4

INTRODUCTION OF AN HSA MINIGENE CONTAINING THE FIRST HSA INTRON INTO A COMPLETE BLG VECTOR (p599)

In order to elucidate the HSA intron pattern which would result in high level expression of HSA in the milk of transgenics, HSA minigenes were constructed composed of the HSA cDNA with different combinations of its introns. One such minigene involves the incorporation of the first HSA intron into an HSA cDNA. In order to make such a construct, a ClaI restriction site was introduced into the region of the HSA cDNA which is derived from HSA exon 2, without changing its coding sequence. This was accomplished by in vitro mutagenesis (Amersham kit) using single stranded DNA template derived from pHSA-F1$^-$ and a synthetic oligonucleotide of the sequence, $$\underset{\text{ClaI}}{5'\text{- GGTTGCTC}\underline{\text{ATCGAT}}\overset{\text{Arg}}{\text{TT}}\text{AAAGATTTGGG-3'}} \text{ [SEQ ID NO:27]}$$

This mutagenesis introduced the ClaI site by replacing the HSA cDNA G with an A in the third base position of the codon for arginine, the 34th amino acid of the HSA protein (including the prepro sequence). Both CGA and CGG codons encode arginine. The resultant clone, made up of an HSA cDNA containing an introduced ClaI site within its exon 2 derived region in the pBS vector, was designated p595.

A DNA fragment composed of intron 1 of the HSA gene, along with parts of flanking exon 1 and exon 2, was produced by PCR technology using synthetic oligonucleotide primers which included sequences complementing to exon 1 and exon 2 as seen below.

Exon 1 Sense Primer

<u>HindIII</u>    <u>Met</u>    <u>BstEII</u>
5'-GTACATAAGCTTTGGCACAATGAAGTGGGTAACCTT-3' [SEQ
            <u>Exon 1 sequence</u>                    ID
                                                  NO:28]

Exon 2 Antisense Primer

<u>ClaI</u>
3'-CCAACGAGTAGCTAAATTTCTAAACCC-5' [SEQ ID NO:29]
                  *
        <u>Exon 2 sequence</u>
*Introduced ClaI site by incorporating a T in this position rather than a C. No change in coding as discussed above.

The template for this PCR reaction was a clone of the HSA gene extending from the gene exon 1 to exon 3, including introns 1 and 2. This clone designated p594 will be discussed later. Following ethanol precipitation, the PCR product of 844 bp was digested with Bst EII and ClaI. The subsequent DNA fragment of 799 bp was gel and elutip purified and ethanol precipitated.

Plasmid p595 was digested with BstEII and ClaI. The large fragment lacking the BLG cDNA region between the Bst EII and ClaI sites was gel purified, electroeluted, elutip isolated and ethanol precipitated.

The purified PCR product with Bst EII and ClaI ends and the purified p595 fragment with Bst EII and Cla I ends were ligated together. Ligation products were transformed into DH5 cells and positive transformants selected on LB-ampicillin plates.

Transformants containing plasmid containing the PCR insert were identified by colony lifts of plates using Whatman 541 filters as described earlier. The probe was $^{32}$P-labeled random primer product of the PCR product used in the ligation. Following autoradiography of filters, probe positive colonies were picked, grown in LB-ampicillin medium. Plasmid preparations from these were analyzed separately with ClaI and XbaI. Correct plasmids which possessed a ClaI site and produced XbaI fragments of 4010 and 1874 bp were identified. A correct recombinant made up of an HSA minigene comprised of its cDNA and HSA intron 1 within a pBS vector was designated p596.

The HSA (Intron 1) minigene was introduced into BLG vector p585 as follows. The HSA (Intron 1) minigene was released from the pBS vector by complete digestion with BamHI and partial digestion with EcoRI. The 2701 bp minigene was gel and elutip purified and ethanol precipitated. The Bam HI and EcoRI ends of the minigene were blunted using Klenow polymerase and excess dNTPs. This blunted fragment was ligated into BLG vector p585 which had been digested with SnaBI and dephosphorylated with CIP. Ligation products were transformed into DH5 cells to ampicillin resistance. Positive colonies were identified by colony lifts with Whatman 541 filters and hybridization to the HSA intron 1 PCR probe describe above. Probe positive colonies identified by autoradiography were grown in LB-ampicillin medium from which plasmid preparations were made. Clones which possessed the HSA (Intron 1) minigene in the desired orientation, that is with the HSA minigene in the same orientation as the BLG gene, were identified by their release of restriction fragments, of approximately 10676 and 3600 bp upon EcoRI digestion and approximately 4490, 3600, 3400 and 2860 bp upon EcoRI/SalI double digestion. This desired clone, the HSA (Intron 1) minigene in the correct orientation of the Sna BI site of BLG vector p585 was designated p599.

EXAMPLE 5

A. CONSTRUCTION OF A BLG VECTOR LACKING CODING SEQUENCE (p590)

The full length BLG vector was altered so that while it still contains the 5'-BLG sequences, including promoter, upstream of the BLG coding sequence and 3'-BLG sequences, including the BLG polyadenylation signal and site, downstream of the coding sequence, all BLG coding sequence was deleted. Plasmid p583, containing the 5'-region of BLG with a SnaBI site replacing the PvuII site in BLG exon 1, was digested with SnaBI and PvuI (within pGEM) The DNA fragment (approximately 4490 bp) containing the pGEM sequences and the 5'-portion of the BLG gene up to the SnaBI site, was gel and elutip purified and ethanol precipitated.

Restriction mapping of plasmid p568, BLG 3'-portion in pGEM-1, demonstrated that the XmaI (isoschizomer of SmaI) site within exon 7 of the BLG gene was the 3'-most Xma I site within the 3'-portion of the gene. Plasmid p568 was digested with XmaI and PvuI (within pGEM). The DNA fragment of approximately 2660 bp containing pGEM sequences and the 3'-end of the 3'-portion of the BLG gene (up to the XmaI site within exon 7) was gel and elutip purified and ethanol precipitated.

Two synthetic oligonucleotides were produced that when annealed formed a SnaBI/XmaI adaptor of the sequence.

$\frac{1}{2}$ <u>SnaBI</u>    <u>XmaI</u>

5' - GTAGATCTC          3'
3' - CATTCTAGAGGGCC 5' [SEQ ID NO:30]
        BLGII

A ligation between the purified fragments from p583, p568 and the annealed oligonucleotide adaptor was performed. Ligation products were transformed into DH5 cells to ampicillin resistance. Correct recombinants were identified by the fact that BglII digestion linearized the plasmid, that BamHI digestion resulted in 3 fragments (approximately 4200, 2050 and 900 bp) and that SnaBI and HindIII digestion produced fragments of approximately 5950 and 1200 bp. These correct recombinants containing the 5'- and 3'-ends of the BLG gene connected by a SnaBI site but without BLG coding sequence were designated p590.

B. CONSTRUCTION OF BLG VECTOR (BLG 5- AND 3'-SEQUENCE, NO BLG CODING SEQUENCE) WITH AN HSA MINIGENE CONTAINING HSA INTRON 1 (p600)

Construct p590 was digested with SnaBI and resultant restricted ends dephosphorylated with CIP. The HSA minigene with intron 1 was released from p596 by complete digestion with BamHI and partial digestion with EcoRI. The 2701 bp fragment composed of the entire minigene was gel and elutip purified and ethanol precipitated. The BamHI and EcoRI ends of this fragment were made blunt using Klenow polymerase and excess dNTPs.

The prepared minigene was ligated into the prepared p590 vector. Ligation products were introduced into E. coli DH5 cells by transformation to ampicillin resistance. Plates containing selected colonies were lifted onto Whatman 541 filters and processed as before. A $^{32}$P-labeled probe, the PCR produced HSA intron 1 discussed in the section describing the construction of plasmid 599, was made by the random primer technique. Hybridization and subsequent filter washes were as described for the colony lifts for the identification of p599 positives. Following autoradiography, probe positive colonies were picked and grown in LB-ampicillin medium. Plasmid preparations from these were subjected to restriction analysis. Correct recombinants, with the HSA minigene cloned into the SnaBI site in the same orientation as the BLG promoter, were identified by the production of a single EcoRI fragment (approximately 9800 bp) and EcoRI/SalI double digest fragments of approximately 3511, 3419 and 2850 bp and were designated p600.

EXAMPLE 6

A. CONSTRUCTION OF BLG VECTOR WITH AN HSA MINIGENE CONTAINING HSA INTRONS 1 AND 2 (P607)

In preparing this construct the HSA cDNA was subcloned into pGEM-1. pGEM-1 was digested with PvuII (just outside of the polylinker) and EcoRI (within the polylinker). The 2819 bp vector fragment was gel and elutip purified and ethanol precipitated. The HSA cDNA subcloned in the plasmid vector pBS⁻ (pHSA-F1⁻) as described in the section on the construction of p575, was released from pHSA-F1⁻ by digestion with SalI which was blunted with Klenow polymerase and excess dNTPs and subsequently digested with EcoRI. The 2004 bp fragment of the HSA cDNA was gel and elutip purified and ethanol precipitated. This cDNA fragment was ligated into the purified pGEM-1 plasmid fragment digested with PvuII (blunt) and EcoRI. Ligation products were transformed into DH5 cells and positive transformants selected on LB-ampicillin plates. Selected colonies were lifted onto Whatman 541 filters as previously described. A $^{32}$P-labeled HSA cDNA probe was produced by the random primer technique using a 1941 bp HindIII fragment of pHSA-F1⁻ as a template. Hybridization was in standard buffer at 65° C. Washing conditions included a final, most stringent wash of 0.5× SSC, 0.2% SDS at 65° C. Probe positive colonies were picked, grown in LB-ampicillin medium. Plasmids obtained from these cultures were subjected to restriction analysis. Correct recombinants were characterized by the presence of 2818 and 2011 bp BamHI fragments and 2806, 1165 and 858 bp XbaI fragments. Correct clones were designated p597.

A DNA fragment encompassing the HSA genomic sequence including part of exon 1, intron 1, exon 2, intron 2 and part of exon 3 was produced by PCR technology using the following synthetic oligonucleotide primers.

Exon 1 Sense Primer

HindIII    Met    BstEII
5'-GTACATAAGCTTTGGCACAATGAAGTGGGTAACCTT-3' [SEQ
             Exon 1 sequence                    ID NO:28]

Exon 3 Antisense Primer

3'        PvuII          ←BamHI
GACTACTCAGTCGACTTTTAACACCTAGGGGACTG-5' [SEQ ID
            Exon 3 sequence                    NO:31]

High molecular weight DNA purified from human lymphocytes was used as a template. This PCR product was digested with Hind III and PvuII and the resultant 2422 bp fragment gel and elutip purified and ethanol precipitated. This fragment was ligated into a pGEM-1 vector prepared by digestion with HindIII and PvuII, gel and elutip purification and ethanol precipitation of the resultant 2774 bp fragment. It was subsequently dephosphorylated with CIP.

Ligation products were used to transform DH5 cells to ampicillin resistance. Correct recombinants clones were identified by the presence of a BstEII site resulting in linearization of plasmid (5196 bp) and the generation of 2774 and 2422 bp fragments upon digestion with Hind III and PvuII. Correct recombinants were designated p594.

HSA introns 1 and 2 were introduced into the HSA cDNA as follows. HSA sequences from exon 1 to exon 3 including introns 1 and 2 were released from p594 by digestion with BstEII (within exon 1) and PvuII (within exon 3) as a 2401 bp fragment. This fragment was gel and elutip purified and ethanol precipitated. Plasmid p597 was similarly digested with BstEII and PvuII. The 4596 fragment (which lacks the cDNA sequences between these sites in the cDNA), was gel and elutip purified and ethanol precipitated. These two prepared fragments were ligated and ligation products transformed into DH5 cells to ampicillin resistance. Transformants containing the HSA introns were identified by Whatman 541 filter lifts and hybridization with a $^{32}$P-5'-end labeled (using T4 polynucleotide kinase) synthetic oligonucleotide probe. The synthetic oligonucleotide used has HSA intron 2 specific sequence, i.e., 5' GTCACATGTG-GCTAATGGCTACTG 3' [SEQ ID NO:32].

Hybridization was in standard buffer at 60° C. Filters were washed with the final wash of 2× SSC, 0.5% SDS, 60° C. Positive colonies were subjected to restriction analysis. Correct recombinants were identified by 2 BamHI (approximately 4174 and 2818 bp) fragments and 2 EcoRI (approximately 3765 and $^{3227}$ bp) fragments. These correct clones contain an HSA minigene possessing HSA introns 1 and 2 and were designated p603.

The HSA minigene with introns 1 and 2 was introduced into BLG vector p590 as follows. Vector p590 was digested with SnaBI and dephosphorylated with CIP. The HSA minigene was released from p603 as a 4174 bp BamHI fragment which was gel and elutip purified and ethanol precipitated. The BamHI ends of this fragment were blunted using Klenow polymerase and excess dNTPs. The prepared minigene from p603 and the prepared vector, p590, were ligated together. Ligation products were transformed into DH5 cells to ampicillin resistance. Correct clones were identified by the presence of 2 EcoRI fragments (approximately 7485 and 3765 bp) and 2 XbaI fragments (approximately 9196 and 2054 bp). The correct clones have the HSA minigene inserted into the SnaBI site of the BLG vector p590 in the same orientation as the BLG promoter and were designated p607.

B. CONSTRUCTION OF A BLG VECTOR WITH A DOWNSTREAM SV40 POLYADENYLATION [POLY (A)] SIGNAL (p589)

In order to examine whether the polyadenylation signal source affected expression of the HSA protein, a BLG vector having the BLG coding sequence replaced by an HSA coding sequence was constructed having an SV40 polyadenylation signal instead of the BLG poly A signal. The BLG sequences contained within the construct made here are only those upstream of the BLG coding sequence which include the promoter region. The BLG coding sequences as well as downstream sequences were deleted. The construct maintains the SnaBI site in BLG exon I for the insertion of foreign genes, in this case HSA. An SV40 polyadenylation signal was placed downstream of the SnaBI site in order to supply this, 3'-RNA processing signal.

Plasmid p583 containing the 5'-EcoRI subgenomic portion of the BLG gene with an SnaBI site introduced in exon 1 was digested with SnaBI and partially digested with SalI. The DNA fragment of approximately 5800 bp made up of almost the entire pGEM-1 plasmid digested at its native SalII site within its polylinker and the 5'-end of the 5'-portion of the BLG gene to the introduced SnaBI site was gel and elutip purified and ethanol precipitated.

The SV40 early gene (T and t) polyadenylation signal [poly (A)] was released from SV40 DNA by restriction with BclI at its 5'-end (SV40 map position 2770) and BamHI at its 3'-end (SV40 map position 2533). The 237 bp poly(A) signal and site fragment was gel and elutip purified and ethanol precipitated. This fragment was ligated into the Bam HI site (dephosphorylated with CIP) of pGEM2. Ligation products were transformed into HB101 cells to ampicillin resistance. As the SV40 poly(A) signal fragment was able to be ligated into the Bam HI site of pGEM in either orientation, the desired orientation was determined by analysis of plasmid DNAs from selected clones by digestion with Dra I. Clones with the desired orientation, (the SV40 poly (A) signal fragment 5'-end (BclI) downstream of the polylinker Xba I and Sal I sites) were characterized by Dra I fragments of 1203, 1192, 692 and 19 bp. Desired recombinants were designated p290. Additional restriction sites including SnaBI were introduced upstream of the poly (A) signal as follows. Plasmid p290 was digested with SacI and AvaI (within the pGEM2 polylinker), the large fragment gel and elutip purified and ethanol precipitated. Into the resultant fragment was ligated synthetic oligonucleotides which when annealed were of the sequence;

```
        SacI         SnaBI          HindIII           [SEQ
                                                       ID
5'      CCTCGAGTACGTAAGATCTAAGCTTC                  3' NO:33]
3' TCGAGGAGCTCATGCATTCTAGATTCGAAGGGCC               5' [SEQ
        XhoI         BglII          AvaI              ID
                                                      NO:34]
```

Ligation products were transformed into E. coli HB101 cells to ampicillin resistance. Resultant correct recombinants which now possessed these additional multiple cloning sites upstream of the poly(A) signal sequence were designated p299.

The SV40 poly(A) signal and site sequences were released from p299 by digestion at the upstream SnaBI and downstream SalI sites. This 270 bp fragment was gel and elutip purified and ethanol precipitated. It was ligated into the SnaBI/partial SalII purified fragment from p583. Ligation products were transformed into DH5 cells to ampicillin resistance. Correct recombinants were identified by linearization by SnaBI (approximately 6200 bp) and the generation of 2 fragments (approximately 3400 and 2800 bp) upon digestion with SalII. Correct recombinants were designated p589.

C. CONSTRUCTION OF BLG VECTOR (BLG 5'-SEQUENCES, SV40 3'-POLY(A) SIGNAL, NO BLG CODING SEQUENCE) WITH AN HSA MINIGENE CONTAINING HSA INTRON 1 (p598)

Construct p589 was digested with SnaBI and resultant restricted ends dephosphorylated with CIP. This DNA was ligated with the prepared HSA minigene with intron 1 blunt ended as described in the section on the concentration of p599 and ligation products introduced in cells by transformation. Correct recombinants with the HSA minigene cloned into the SnaBI site in the same orientation as the BLG promoter were identified by the production of a single EcoRI linear fragment (approximately 8800 bp) and EcoRI/SalII fragments of approximately 3450, 2850 and 2500 bp. These correct clones were designated p598.

D. INTRODUCTION OF AN HSA MINIGENE CONTAINING THE FIRST HSA INTRON INTO A BLG VECTOR WITH EXTENDED 5'-SEQUENCES (p643, p647)

In order to ascertain whether longer 5' BLG would increase the expression of HSA, an HSA minigene, with intron 1, was introduced into BLG constructs with extended 5'-BLG sequences (5.5 Kb or 10.8 Kb). BLG coding and 3'-sequences are not included into these vectors. The SV40 3'-sequences containing the polyadenylation signal and site are included.

In order to produce the clone with the BLG 5.5 Kb 5'-sequence construct p640 was digested with Asp718, (between the original BLG 5'-EcoRI site and the transcriptional initiation site), and PvuI (within pGEM). The fragment (approximately 6143 bp) which includes pGEM sequences and the BLG sequences upstream of the Asp 718 site was gel and elutip purified and ethanol precipitated. Vector p598 was similarly digested with Asp 718 and PvuI. The fragment (approximately 5184 bp) which includes pGEM sequences, complementary to those above, as well as BLG 5'-sequences downstream of the Asp718 site, the HSA minigene with its first intron and the SV40 poly(A) site, was gel and elutip purified and ethanol precipitated. These two fragments were ligated together and ligation products transformed into DH5 cells to ampicillin resistance. Correct recombinants were identified by the generation of 3 fragments (approximately 8164, 2831 and 320 bp) upon Hind III digestion and were designated p643.

The BLG 10.8 Kb 5'-sequence construct was made in a similar manner as for p643. Plasmid p645 was digested with Asp718 and PvuI. The resultant fragment (approximately 11,384 bp) was gel and elutip purified and ethanol precipitated. This fragment was ligated to the purified fragment (approximately 5184 bp) generated by the digestion of p598 with Asp718 and PvuI discussed above. Ligation products were transformed into DH5 cells to ampicillin resistance. Correct recombinants were identified by the generation of 5 DNA fragments (approximately 8159, 3460, 2829, 1800 and 320 bp ) upon digestion with HindIII. Correct recombinants were designated p647 and include 5'-BLG sequences of 10.8 Kb in combination with an HSA minigene possessing intron 1.

EXAMPLE 7

CONSTRUCTION OF BLG VECTORS WITH AN HSA MINIGENE CONTAINING HSA INTRONS 1–6 (p652, p661)

Transgenic BLG constructs with an HSA minigene containing HSA introns 1–6 were made by taking advantage of the unique Bst EII (within exon 1) and the NcoI (within exon 7) sites within the HSA gene.

Construct p598, which is equivalent to the desired vector except that its HSA minigene contains only intron 1, was digested with Bst EII and NcoI. The DNA fragment (approximately 7304 bp) lacking HSA sequences between these two sites was gel and elutip purified and ethanol precipitated. Plasmid p650 was similarly digested with Bst EII and NcoI. The resultant 7,756 bp fragment containing the HSA gene region between these sites including introns 1–6 was also gel purified and ethanol precipitated. The two purified fragments were ligated together and transformed into TG1 cells to ampicillin resistance. Correct recombinants were identified by 4 DNA fragments (approximately 9819; 4682; 320; and 240 bp) upon digestion with HindIII and 5 fragments (approximately 9552; 1882; 1296; 1258; and 1073 bp) upon digestion with XbaI. These were designated p652 (ATCC No. 68653). Construct p652 possesses a SV40 poly(A) site.

A second BLG vector similar to p652, except that 3'-sequences containing the polyadenylation signal and site were contributed by BLG 3'-sequences, was constructed in a parallel manner. Construct p600 was digested with Bst EII and NcoI. The DNA fragment of approximately 8266 bp, lacking HSA sequences between these sites was gel and elutip purified and ethanol precipitated. It was ligated with the purified 7756 bp p650 Bst EII-NcoI fragment discussed above, composed of HSA gene sequences between these two sites. Ligation products were transformed into DH5 cells to ampicillin resistance. Correct recombinants were identified by the possession of unique Bst EII and NcoI sites, resulting in the generation of a single DNA fragment (approximately 16021 bp) upon digestion with each restriction enzyme. In addition, correct clones were identified by the generation of 3 DNA fragments (10945; 4171 and 905 bp) upon digestion with Bam HI. Correct clones were designated p661.

EXAMPLE 8

CONSTRUCTION OF BLG VECTOR WITH AN HSA MINIGENE CONTAINING HSA INTRONS 7–14 (p687)

This transgenic vector made up of an HSA minigene with introns 7–14 under the control of the BLG promoter and with an SV40 poly (A) site was constructed in several steps. The downstream HSA gene region containing introns 12–14 (within p651) was combined with HSA cDNA sequences up to intron 12, thereby creating an HSA minigene with introns 12–14. An SV40 poly(A) site was then joined to the 3'-end of this minigene. This was then manipulated to include introns 7–11 to produce an HSA minigene with introns 7–14, with an SV40 poly(A) site. Finally, the minigene was recombined with the 5'BLG promoter sequences resulting in construct p687.

In the first step, construct p651 was digested with AspI (within HSA exon 12) and HindIII (within HSA intron 15). The resultant, desired, fragment (2972 bp) extending from exon 12 to exon 15 was gel and elutip purified. Translational termination of the HSA RNA occurs within exon 14 derived sequences and polyadenylation of the HSA transcript occurs downstream of the HindIII site. Therefore, the isolated fragment has been separated from the HSA poly(A) signal and site but has not had any coding sequences deleted. Construct p597 (HSA cDNA within pGEM-1) was similarly digested with AspI and HindIII. The resultant fragment (approximately 4263 bp) with the HSA cDNA sequences between the AspI (within exon 12 derived sequences) and HindIII (within exon 15 derived sequences) was gel and elutip purified. The two fragments were ligated together and ligation products introduced into *E. coli* MC1061 cells by electroporation to ampicillin resistance. The correct recombinants were characterized by the presence of single AspI and HindIII sites as well as 2 fragments (approximately 4275 and 2800 bp) upon digestion with EcoRI and BamHI and were designated p668. Construct p668 contains an HSA minigene with introns 12–14 within pGEM-1.

SV40 poly(A) signal and site sequences were introduced downstream of the HSA minigene in p668. Construct p668 was digested with HindIII (at the downstream end of HSA sequences) and the blunt cutter NaeI (within pGEM sequences approximately 300 bp from the HindIII site). The fragment (approximately 6800 bp), deleted of the 300 bp between the two sites, was gel and elutip purified. SV40 poly(A) site sequences were released from p299 by first digesting with PstI (within the multiple cloning site adjacent to the downstream end of the poly(A) site sequences). The SalI site between the poly(A) site sequences and the PstI site remains adjacent to the downstream end of the poly(A) site sequences. The digested PstI site was blunted by filling in with T4 DNA polymerase in the presence of excess dNTPs. The DNA was then digested with HindIII (within the multiple cloning site adjacent to the upstream end of the poly(A) site sequences) and the released SV40 sequences fragment (approximately 200 bp) was gel and elutip purified. The two purified DNAs were ligated together and transformed into *E. coli* DH5 cells to ampicillin resistance. Correct clones with the SV40 poly(A) site ligated at the downstream end of the HSA minigene in the same orientation were characterized by the generation of 2 fragments (approximately 4700 and 2300 bp) upon SalI digestion and 3 fragments (approximately 4200, 2300 and 500 bp) upon SalI and EcoRI digestion. These correct constructs were designated p674.

The introduction of HSA introns 7–11 into p674 containing the HSA minigene with introns 12–14 was accomplished by a tripartite ligation. The HSA gene sequences contained within p679 were released by digestion with NcoI (within exon 7) and HindIII (within the downstream end of intron 8) as a fragment of 2814 bp which was gel and elutip purified. The HSA sequences contained within p676 were released by digestion with HindIII (the same site within the downstream end of intron 8 described for p679) and partial digestion with AspI (within exon 12; a second AspI site is found within intron 11) as a fragment of 3237 bp which was gel and elutip purified. Construct p674 (containing the HSA minigene with introns 12–14) was digested with NcoI (again within exon 7) and AspI (again within exon 12). The resultant DNA (approximately 6400 bp) deleted of HSA cDNA sequences between the NcoI and AspI sites was gel and elutip purified. The 3 purified DNAs were ligated together and ligation products introduced into *E. coli* MC1061 cells by electroporation to ampicillin resistance. Correct recombinants were characterized by the generation of 2 AspI fragments (approximately 12406 and 273 bp) and 5 XbaI fragments (approximately 3537, 2719, 2623, 2566 and 1234 bp). These correct constructs, designated p683, are HSA minigenes with introns 7–14, with an adjacent downstream SV40 poly(A) site within pGEM-1.

Finally, the HSA minigene with introns 7–14 was introduced into a transgenic construct downstream of the BLG 5'-flanking promoter sequences. Construct p683 was digested with NcoI (within HSA exon 7) and PvuI (within pGEM). The DNA fragment (approximately 10400 bp) made up of the HSA gene sequences downstream of the NcoI site (including introns 7–14), the SV40 poly(A) site and the adjacent pGEM sequences was gel and elutip purified. Construct p572 (containing the HSA cDNA within the PvuII site of BLG exon 1) was similarly digested with NcoI (within exon 7 derived sequences) and PvuI (within pGEM). The DNA fragment (approximately 5570 bp) made up of pGEM sequences complementary to the pGEM sequences in the fragment described above, BLG 5'-flanking promoter sequences and the HSA cDNA up to the NcoI site within exon 7, was gel and elutip purified. The two purified fragments were ligated together and ligation products were introduced into *E. coli* DH10B cell by electroporation to ampicillin resistance.

Correct recombinants were characterized by 3 fragments (approximately 10098, 4183 and 1699 bp) generated by digestion with BamHI. These correct constructs, designated p687, contain the HSA minigene with introns 7–14, a downstream SV40 poly(A) site and an upstream BLG promoter and represent a final BLG/HSA construct for introduction into transgenic animals.

EXAMPLE 9

CONSTRUCTION OF BLG VECTOR WITH AN HSA MINIGENE CONTAINING INTRONS 2 AND 7–14 (p696)

The construction of this transgenic vector containing an HSA minigene with introns 2 and 7–14 was performed in several steps. The ClaI site which had previously been introduced into HSA exon 2 derived sequences (without altering the encoded amino acid) in an HSA cDNA in plasmid pBS⁻ (p595) was transferred into an HSA cDNA within a pGEM plasmid. A PCR product extending from HSA exon 2 through intron 2 and into exon 3 was introduced into the homologous region in the HSA cDNA within pGEM using this ClaI site. Finally, intron 2 was transferred into the transgenic construct carrying an HSA minigene with introns 7–14 (p687).

The ClaI site which had been introduced into HSA exon 2 was transferred from the HSA cDNA in construct p595 (pBS⁻ plasmid) to an HSA cDNA in a pGEM plasmid (p597) because there are multiple PvuII sites within p595 which interfere with the subsequent recombination strategy (p597 has a unique PvuII site). Construct p597 was digested with BstEII (within HSA exon 1 derived sequences) and NcoI (within HSA exon 7 derived sequences). The large DNA fragment deleted of the HSA cDNA sequences between the BstEII and NcoI sites was gel and elutip purified. Construct p595 was similarly digested with BstEII and NcoI and the DNA fragment (801 bp) of the HSA cDNA sequences between these sites, including the previously introduced ClaI site, was gel and elutip purified. These two purified DNAs were ligated together and ligation products introduced into *E. coli* DH10B cells by electroporation to ampicillin resistance. Correct recombinants were characterized by the presence of a ClaI site and were designated p689.

HSA intron 2, with flanking exon regions including the introduced ClaI site in exon 2, was obtained by PCR technology. The HSA exon 2 sense synthetic oligonucleotide primer (with incorporated ClaI site) and the HSA exon 3 antisense primer (with incorporated PvuII site), shown below, were used for a PCR with construct p594 (containing HSA intron 2 and flanking exons) as template.

| HSA Exon 2 Sense Primer | 5' GGTTGCTC<u>ATCGAT</u>TTAAAGATTTGGG 3' [SEQ ID NO:27] |
| --- | --- |
| | ClaI |

| HSA Exon 3 Antisense Primer | 3' GACTACTC<u>AGTCGAC</u>TTTTAA*cacttaagggactg* 5' [SEQ ID NO:35] |
| --- | --- |
| | PvuII (Non-HSA Sequences) |

The reaction was of 28 cycles of 94° C. (1'30"), 55° C. (2') and 72° C. (3'). Following two chloroform extractions and ethanol precipitation the PCR products were digested with ClaI and PvuII. The resultant 1602 bp DNA was gel and elutip purified. Construct p689 was digested with ClaI (within HSA exon 2) and PvuII (within HSA exon 3) and the large DNA fragment deleted of HSA cDNA sequences between the ClaI and PvuII sites was gel and elutip purified. The two purified DNAs were ligated together and ligation products transformed into *E. coli* DH5 cells to ampicillin resistance. The generation of linear DNA of approximately 6500 bp by ClaI and PvuII, individually, identified correct recombinants. These were designated p690 and are composed of an HSA minigene with intron 2 within a pGEM plasmid.

Finally, HSA intron 2 was transferred into transgenic vector p687 containing an HSA minigene with introns 7–14. Construct p687 was digested with BstEII (within HSA exon 1) and NcoI (within HSA exon 7). The large DNA fragment deleted of HSA cDNA sequences between the BstEII and NcoI sites was gel and elutip purified. Construct p690 was similarly digested with BstEII and NcoI. The released 2255 bp fragment made up of HSA cDNA from the BstEII site to the NcoI site and includes intron 2, was gel and elutip purified. The two purified DNAs were ligated together and ligation products transformed into *E. coli* DH5 cells. Correct recombinants were characterized by the release of a 2255 bp fragment upon digestion with BstEII and NcoI. These constructs, designated p696 (ATCC No. 68654), are made up of an HSA minigene with introns 2 and 7–14 under the control of the BLG promoter and flanked downstream by an SV40 poly(A) site and are suitable for the production of transgenic animals.

EXAMPLE 10

CONSTRUCTION OF BLG VECTOR WITH A COMPLETE HSA GENE INCLUDING ALL INTRONS, 1–14 (p686)

The construction of the transgenic vector utilizing the entire HSA gene including all 14 of its introns was by recombining construct p652, containing an HSA minigene with introns 1–6, and construct p683, containing an HSA minigene with introns 7–14. Construct p652 was digested with NcoI (within HSA exon 7) and PvuI (within pGEM). The DNA fragment (approximately 12530 bp) made up of pGEM sequences, the BLG 5'-flanking promoter and the HSA minigene (including introns 1–6) up to the NcoI site in exon 7 was gel and elutip purified. Construct p683 was similarly digested with NcoI (within HSA exon 7) and PvuI (within pGEM). The DNA fragment (approximately 10400 bp) made up of the HSA minigene downstream of the NcoI site in exon 7 (including introns 7–14), the adjacent downstream SV40 poly(A) site and its adjacent pGEM sequences complementary to the pGEM sequences in the fragment described above, was gel and elutip purified. The two purified fragments were ligated together and ligation products were introduced into *E. coli* DH10B cells by electroporation to ampicillin resistance. Correct recombinants were characterized by the generation of two fragments (approximately 18728 and 4186 bp) upon digestion with BamHI and were designated p686.

All exons were sequenced in this vector and found to be correct thereby confirming that clonings of the HSA gene had been correct.

EXAMPLE 11

IN VITRO (TISSUE CULTURE) ANALYSIS OF BLG/HSA VECTORS

In order to determine that all of the BLG/HSA vectors introduced into transgenic animals had the potential ability to support the expression of HSA in the milk of such animals, the ability to support expression of HSA in tissue culture cells was first tested. The natural in vivo regulation of expression of milk proteins under the control of their native promoters (e.g., BLG) is complex and requires the influence of hormones and specific cell-cell interactions.

The BLG 5'-flanking promoter sequences are not usually active in tissue culture cells and tissue culture systems which precisely mimic the natural in vivo conditions did not exist.

In order to stimulate these sequences into activity an SV40 enhancer was introduced within the promoter. This allowed the testing of the levels of expression of HSA in tissue culture supported by BLG/HSA constructs which differ in their HSA gene makeup (cDNA, minigenes, gene). In order to keep the genetic background the same in these in vitro analysis constructs, a series of constructs were made which differed only in the HSA gene components. An SV40 enhancer was first introduced into transgenic construct p652 (3 kb BLG 5'-flanking promoter sequences; HSA minigene with introns 1–6; SV40 poly(A) site). The resultant in vitro construct was then used to make all other constructs of this series so that while the HSA sequences varied, the BLG promoter with introduced SV40 enhancer was identical in all. In addition all possessed the same SV40 poly(A) site downstream of the HSA sequences.

Figure 2C:
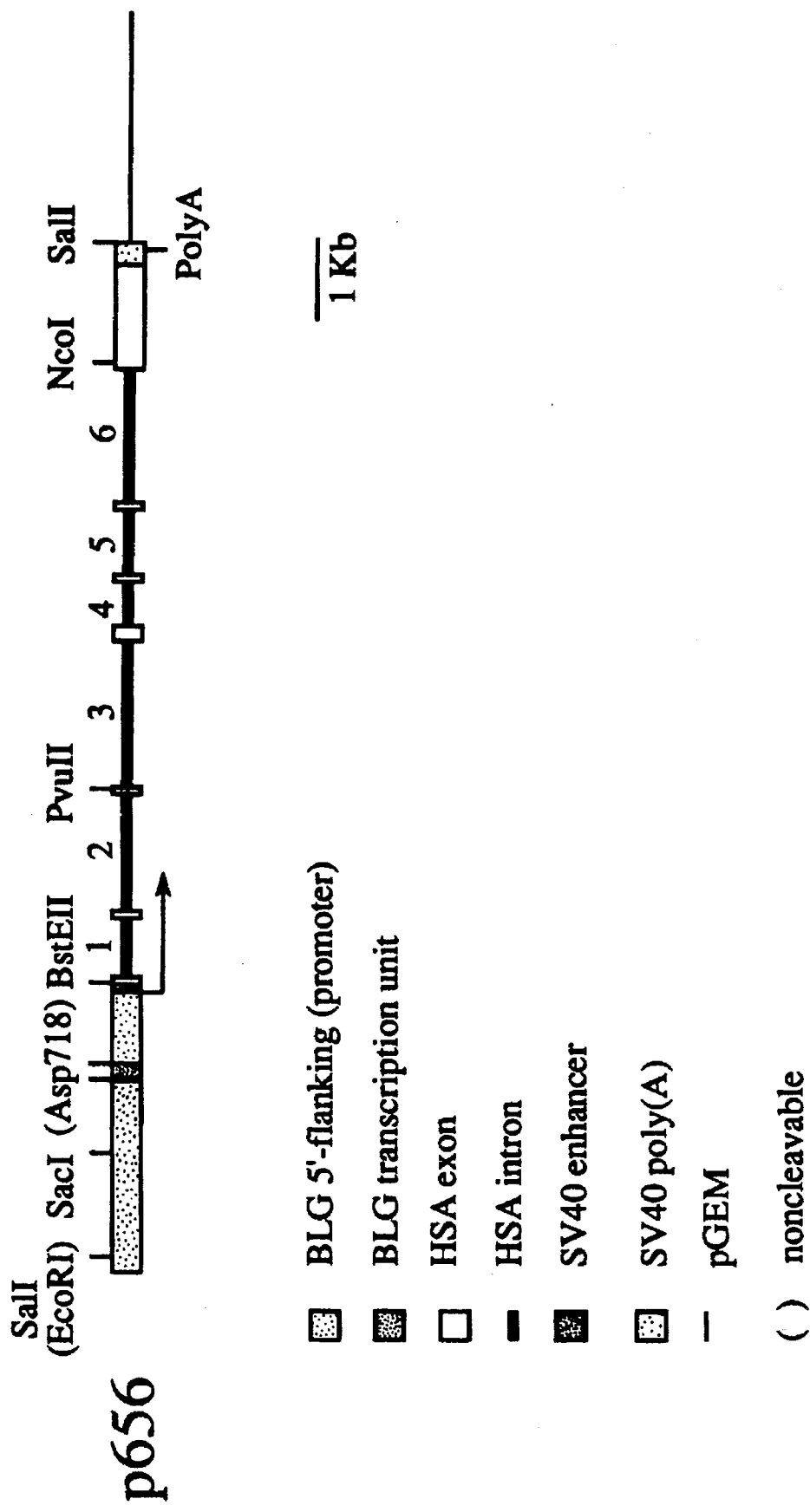

Construct p652 was digested with Asp718 (within the BLG promoter, approximately 900 bp upstream of the BLG transcriptional start site). The linearized construct was extracted two times with phenol/chloroform and ethanol precipitated. The Asp718 digested ends were blunted by filling in with Klenow enzyme (Boehringer Mannheim) in the presence of excess dNTPs. Following the fill in reaction, the enzyme was heat inactivated (65° C., 15') in the presence of 10 mM EDTA. The sample was again extracted two times and ethanol precipitated. The linearized and blunted DNA was gel and elutip purified and it's 5'-ends dephosphorylated with calf intestinal alkaline phosphatase (Promega). The enzyme was heat inactivated (65° C., 15') in the presence of 20 mM EGTA. The sample was again extracted two times and ethanol precipitated. The SV40 enhancer was released from construct pSV$_2$CAT (Gorman et al., 1982, Mol. Cell. Biol. 2, 1044–1051) as a 179 bp FokI (cleaves at SV40 bp position 94) to PvuII (cleaves at SV40 bp position 273) fragment. The fragment was gel and elutip purified and subsequently ligated to the prepared p652 fragment. Ligation products were transformed into E. coli TG1 cells to ampicillin resistance. Correct recombinants were identified by digestion with BamHI and EcoRI whose sites flank the Asp718 site of p652. The conversion of the approximate 2088 bp fragment to approximately 2267 bp identified correct recombinants with an SV40 enhancer introduced into the Asp 718 site of p652. These were designated p656. (FIG. 2C) In vitro analysis construct, p656 is capable of expression of the HSA minigene with introns 1–6 in tissue culture cells.

Several new in vitro analysis constructs were made directly using in vitro analysis construct p656. Construct p656 was digested with BstEII (within HSA exon 1) and NcoI (within HSA exon 7). The large DNA fragment deleted of HSA sequences between these two sites was gel and elutip purified. DNA fragments of HSA sequences between the BstEII site in exon 1 and the NcoI site in exon 7 made up of cDNA (801 bp) or which included intron 1 (1510 bp) or intron 2 (2255 bp) or introns 1 and 2 (2964 bp) were derived from p582 (containing HSA cDNA, discussed below), p600 (containing HSA minigene with intron 1), p690 (containing HSA minigene with intron 2) or p607 (containing HSA minigene with introns 1 and 2), respectively, by digestion with BstEII and NcoI. Fragments were gel and elutip purified and individually ligated into the purified p656 fragment lacking sequences between these two sites. Ligation products were introduced into E. coli DH5 alpha cells by transformation or E. coli DH10B cells by electroporation to ampicillin resistance. Correct recombinants were identified by the generation of DNA fragments of 801, or 1510, or 2255, or 2964 bp, respectively, upon digestion with BstEII and NcoI. The new in vitro analysis construct containing HSA cDNA was designated p658. The constructs containing HSA minigene with intron 1 was designated p659, with intron 2, p691, and with introns 1 and 2, p660.

In addition to making a BLG/HSA in vitro analysis construct with the HSA cDNA, we also made an in vitro analysis construct with the HSA cDNA under the control of the highly active Adenovirus major late promoter and SV40 enhancer combination. This allowed the evaluation of HSA expression from its cDNA in a construct other than a BLG construct. This construction was made in two steps. In the first step the SV40 early region small t splicing signals and poly(A) site was placed downstream of a polylinker, which itself is downstream of the major late promoter. An in vitro analysis construct (referred to here as p550) made up of the major late promoter with an SV40 enhancer introduced at its EcoRV site and followed by a polylinker (Hurwitz et al., 1987, Nucleic Acids Research 15:7137–7153) was digested with BamHI (within the polylinker). The linearized DNA (2818 bp) was gel and elutip purified. It's 5'-ends were dephosphorylated with calf intestinal alkaline phosphatase. The enzyme was heat inactivated as previously described, extracted with phenol/chloroform two times and ethanol precipitated. This fragment was ligated to an approximately 850 bp fragment (BgIII at the upstream end and BamHI at the downstream end) consisting of SV40 small t splicing signals and a downstream poly(A) site (Mulligan, R. C. and P. Berg, Science 209:1423–1427, 1980). Ligation products were introduced into E. coli DH5 cells by transformation to ampicillin resistance. Correct recombinants with the splicing signals and poly(A) site within the BamHI site of p550 in the same orientation as the major late promoter were characterized by the generation of two fragments (approximately 2809 and 856 bp) upon digestion with BamHI and EcoRI. These were designated p566. The HSA cDNA was then introduced into p566. Construct p566 was digested with the blunt cutter NaeI and EcoRI just downstream of NaeI (both sites are within the polylinker between the major late promoter and the downstream SV40 splicing signals and poly(A) site). The HSA cDNA was obtained as follows. Construct pHSA-F1⁻ was digested with BamHI (at the 5'-end of the HSA cDNA) and ethanol precipitated. The digested BamHI site was blunted with Klenow enzyme in the presence of excess dNTPs. The DNA was ethanol precipitated and digested with EcoRI (at the 3'-end of the HSA cDNA). The resultant cDNA fragment (1983 bp) was gel and elutip purified. It was then ligated into the prepared p566 DNA and ligation products introduced into DH5 cells by transformation to ampicillin resistance. Correct recombinants were characterized by the restoration of the unique EcoRI site and the generation of fragments (approximately 4208, 1399 and 36 bp) upon digestion with BgIII. This in vitro analysis construct with the HSA cDNA under the control of the major late promoter was designated p582.

HSA introns 12–14 were introduced into p658 as follows. Construct p658 was digested with NcoI (within HSA exon 7) and partially with SalI (at the downstream end of the SV40 poly(A) site; a second SalI site is found at the upstream end of the BLG promoter). The DNA fragment of approximately 6000 bp deleted of HSA sequences downstream of the NcoI site in exon 7 and the SV40 poly(A) site was gel and elutip purified. Construct p674 was digested with NcoI (within HSA exon 7) and SalI (at the downstream end of the adjacent SV40 poly(A) site). The DNA fragment of approximately 4000 bp made up of HSA sequences downstream of the NcoI site in exon 7, including exons 12–14, and the poly(A) site was gel and elutip purified. These two fragments were ligated together and products were introduced into *E. coli* MC1061 cells by electroporation to ampicillin resistance. Correct recombinants were characterized by 2 DNA fragments (approximately 8021 and 2824 bp) upon digestion with SalII and 3 fragments (approximately 7229, 2757 and 859 bp) upon digestion with XbaI. This new in vitro analysis construct contains an HSA minigene with introns 12–14.

A construct containing an HSA minigene with introns 7–14 was made by first digesting p658 (containing an HSA cDNA) with NcoI (within HSA exon 7) and PvuI (within pGEM). The large DNA fragment (approximately 5569 bp) made up of the BLG promoter with introduced SV40 enhancer and HSA cDNA to the NcoI site in exon 7, as well as pGEM sequences to the PvuI site adjacent to BLG sequences was gel and elutip purified. Construct p683 was also digested with NcoI (within HSA exon 7) and PvuI (within pGEM). The DNA fragment (approximately 10400 bp) made up of HSA sequences downstream of the NcoI site, including introns 7–14, the SV40 poly(A) site and adjacent pGEM sequences (complementary to those found in the fragment above) was gel and elutip purified. The two purified fragments were ligated together and ligation products were introduced into *E. coli* DH5 alpha cells by electroporation to ampicillin resistance. Correct recombinants were identified by the generation of 2 fragments each upon digestion with BamHI (approximately 11998 and 4185 bp) or HindIII (approximately 9973 and 6210 bp). This new in vitro analysis construct with an HSA minigene with introns 7–14 was designated p684.

HSA introns 1 or 2 or 1 and 2 were introduced into the new in vitro analysis constructs already containing HSA minigenes with either introns 12–14 (p682) or introns 7–14 (p684). Constructs p682 and p684 were each digested with BstEII (within HSA exon 1) and NcoI (within HSA exon 7) and the resultant large DNA fragments deleted of HSA sequences between these two sites were gel and elutip purified. Into each were individually ligated the purified DNA fragments, discussed above, (1510, or 2255 or 2964 bp) of HSA sequences between the BstEII and NcoI sites including intron 1 or intron 2 or introns 1 and 2, respectively. Ligation products were either introduced into *E. coli* DH5 cells by transformation or *E. coli* DH10B cells by electroporation. Correct recombinants were identified for each set of parental clones, p682 and p684, by the generation of 1510 bp (for the introduction of intron1 ) 2255 bp (for the introduction of intron 2) or 2964 bp (for the introduction of introns 1 and 2) DNA fragments upon digestion with BstEII and NcoI. The designations of the new in vitro analysis constructs and their specific HSA minigene structure is listed below.

| | |
|---|---|
| p694 HSA minigene with introns | 1 + 12 – 14 |
| p695 HSA minigene with introns | 2 + 12 – 14 |
| p697 HSA minigene with introns | 1 + 2 + 12 – 14 |
| p693 HSA minigene with introns | 1 + 7 – 14 |
| p692 HSA minigene with introns | 2 + 7 – 14 |
| p698 HSA minigene with introns | 1 + 2 + 7 – 14 |

An in vitro analysis construct containing the entire HSA gene with all 14 introns was made as follows. Construct p656 was digested with NcoI (within HSA exon 7) and PvuI (within pGEM). The DNA fragment (approximately 12326 bp) made up of pGEM sequences (from the PvuI site) adjacent BLG promoter with introduced SV40 enhancer and the HSA sequences to the NcoI site within exon 7 including introns 1–6 was gel and elutip purified. To this fragment was ligated the purified p683 NcoI to PvuI fragment (approximately 10400 bp), discussed above, made up of HSA sequences downstream of the NcoI site in exon 7, including introns 7–14, the SV40 poly(A) site and adjacent pGEM sequences to the PvuI site. Ligation products were introduced into *E. coli* DH10B cells by electroporation to ampicillin resistance. Correct recombinants were characterized by the generation of two fragments (approximately 18929 and 4186 bp) upon digestion with BamHI. This in vitro analysis construct containing the entire HSA gene with introns 1–14 was designated p685.

The In vitro tissue culture expression was accomplished by transient transfection. Tissue culture mammalian cell line COS-7 cells were split equally into 100 mm tissue culture dishes in DMEM medium plus 10% fetal calf serum (FCS) so that they were approximately 50–75% confluent (approximately $5 \times 10^6$ cells). They were incubated overnight at 37° C. in a $CO_2$ incubator. The next morning the medium was replaced with 5 ml of fresh medium and cells incubated for 1–2 hours. They were then transfected with BLG/HSA constructs (which included the SV40 enhancer) using the calcium phosphate technique (reagents supplied by 5 Prime→3 Prime, Inc.) by the supplier's protocol. Within each experiment the total amount of the largest construct (kb), for that experiment, transfected into cells within a plate was 25 ug. In order to transfect equal molar amounts of smaller constructs, the amounts of each of these constructs were reduced proportionally to their size differences to the largest construct and the total amount of DNA for the each construct was brought up to 25 ug using high molecular weight (HMW) salmon sperm (ss) DNA. Following transfection of cells for 4–5 hours, cells were glycerol shocked (3 ml, 2 minutes) and washed according to supplier's protocol and subsequently incubated in 10 or 15 ml of DMEM medium plus 10% FCS for 3 days.

In order to detect the transient expression and secretion of HSA, transfected cells were starved for amino acids cysteine (Cys) and methionine (Met) by first washing with and then incubating cells in DMEM medium (plus glutamine) lacking Cys and Met plus 5% dialyzed FCS (dFCS) for 1–3 hours. Following removal of medium from cells, cells (and de novo synthesized proteins) were metabolically labeled with 3 ml DMEM (plus glutamine, without Cys or Met, plus 10% dialyzed FCS) containing $^{35}$S-Cys and $^{35}$S-Met (Expre$^{35}$S$^{35}$S$^{35}$S-Protein labeling mix; New England Nuclear, Inc.) at approximately 200 uCi/ml for 4–5 hours.

After metabolic labeling, the supernatants were harvested from dishes and centrifuged to remove any contaminating cells. Metabolically labeled HSA expressed and secreted into supernatants was detected by immuno-precipitation using rabbit anti-HSA antibodies (DAKO-immunoglobulins Cat. #A001). Supernatants were first precleared with 200 ul of 50% slurry of protein A-Sepharose beads in immunoprecipitation (IPP) buffer (20 mM Tris, pH 8, 150 mM NaCl, 1% NP-40, 0.1% SDS, 2 ug/ml aprotinin) at 4° C. for 30–60 minutes with rocking. Cleared supernatants were separated from beads by centrifugation and treated with rabbit anti-HSA IgG prebound to protein A-Sepharose Sepharose beads, at 4° C. for 3–4 hours. Beads were washed 6 times with cold IPP buffer, resuspended in 2× SDS-PAGE Laemmli sample buffer, heated to 95° C. for 5 minutes and run on 8% SDS-PAGE gels. Following electrophoresis, gels were fixed (10% acetic acid, 25% isopropanol), treated with the fluorographic reagent Amplify (Amersham, Inc.), dried onto Whatman 3MM paper and used to expose X-ray film.

Developed films (autoradiographs) allowed visualization of the relative levels of expression and secretion of metabolically labeled HSA from each of the tissue culture transient assay plates supported by each of the analyzed BLG/HSA constructs.

The first in vitro analysis demonstrated that HSA can be expressed from constructs containing the HSA cDNA within a BLG construct containing the BLG coding as well as BLG 3'-sequences and polyadenylation [poly(A)] site (p615), an HSA minigene containing intron 1 within constructs lacking the BLG coding sequences but which possess either the BLG poly(A) site (p606), or the SV40 poly(A) site (p608), or an HSA minigene with introns 1 and 2 within a construct with the BLG poly(A) site (p610). The HSA produced from these vectors comigrate with HSA produced from a non-BLG transient vector with the HSA cDNA under the control of an SV40 enhancer/Adenovirus major late promoter (p582). As expected BLG constructs which lack the SV40 enhancer (p600) do not express HSA in vitro. The immunoprecipitation of the band seen in this in vitro analysis is specific to the anti-HSA serum and is not precipitated with a non-specific antiserum demonstrating that the band is in fact HSA. Significantly, the levels of expression increase with the increase in number of introns with the cDNA being expressed least and the HSA minigene with introns 1 and 2 expressed to the highest level in this group. The levels of expression from p606 and p608 (HSA minigenes with intron 1) are equivalent indicating that the origin (SV40 or BLG) of the 3'-poly(A) site does not affect levels of expression in this assay.

This previous analysis was performed on constructs which varied in components in addition to the HSA intron variations. In order to specifically analyze the effect of HSA intron number and position on levels of expression in this in vitro assay, constructs which vary only in HSA introns (FIG. 3A) were tested. All of these constructs contain the same BLG 5'-flanking sequences (promoter) with introduced SV40 enhancer as well as the same 3'-sequences (SV40 poly(A) site). A wide range of levels of expression are obtained from constructs with different HSA minigenes. As before, the very low level of HSA expression with the HSA cDNA (lane 1) is increased with the HSA minigene with intron 1 (lane 2) and further increased with introns 1 and 2 (lane 3). Inclusion of intron 2 alone (lane 9) has a similar effect as both introns 1 and 2 (lane 3) and clearly intron 2 is more efficacious than intron 1 alone (lane 2). This finding demonstrates that specific introns are more effective than others in providing expression of HSA. In addition, simply increasing the number of introns does not necessarily further increase expression as seen by the fact that the presence of the last 3 HSA introns, 12–14 (lane 6) results in a lower level of expression than intron 2 alone (lane 9) but a similar level as with intron 1 alone (lane 2). This may be due to the nature of the specific introns and/or to their relative positions within the gene, with introns 12–14 at the 3'-end rather than the 5'-end. Significantly, similar and higher levels of expression are obtained with constructs containing either HSA minigenes containing the first 6 introns (introns 1–6, lane 4), the last 8 introns (introns 7–14, lane 7) or the entire HSA gene with all of its introns, 1–14 (lane 8). While the specific reasons for the increased and similar levels of expression obtained when using introns 1–6 or 7–14 are unknown, it is clear that the inclusion of either of these subsets results in expression as high as the inclusion of all HSA introns. The extremely high level of expression obtained with an HSA minigene containing introns 2 and 7–14 (lane 10) demonstrates the synergistic effects of specific intron combinations on levels of expression, and that expression of HSA can be increased several fold by incorporating these specific intron combinations as opposed to the inclusion of the entire gene with all of its introns.

The synergistic effects of specific HSA intron combinations on levels of expression of HSA (FIG. 3B) were investigated. The same relative levels of expression from constructs previously discussed, including the synergistic effect of introns 2 and 7–14 (lane 14) where expression is extremely high and much higher than what would result from an additive effect of intron 2 (lane 3) and introns 7–14 (lane 12). The combination of introns 1 and 7–14 (lane 13) was not synergistic since the level of expression supported by this construct is about the same as that supported by the construct with only introns 7–14 (lane 12). Additional synergistic combinations were also demonstrated. While the levels of expression from constructs with either HSA introns 1 (lane 2) or introns 12–14 (lane 8) are very low, introns 1 and 12–14 (lane 9) result in significantly higher levels than either alone or the additive effect of both together. The levels of expression due to the synergy between introns 2 and 12–14 (lane 10) were even higher. An even greater three part synergy involving introns 1 and 2 and 12–14 (lane 11) demonstrating levels of expression higher than that expected from an additive effect of the three alone or the additive effects of 1 with 12–14 and 2 or 2 with 12–14 and 1. The resultant level of expression with introns 1 and 2 and 12–14 was higher than with introns 1–6 (lane 6) or introns 7–14 (lane 12) or the entire gene with introns 1–14 (lane 5). The highest level of expression in these experiments was supported by a construct with HSA introns 2 and 7–14 (lane 14), similar to introns 1 and 2 and 7–14 (lane 15). This was several fold higher than that supported by other construct s tested including one with the entire HSA gene with all 14 of its introns.

These results demonstrate that in living cells the level of expression of HSA is modulated by the specific complement of HSA introns, i.e., the number of HSA introns present in the construct, the specific introns incorporated, the relative location of introns, and the synergies between specific introns. Several fold higher levels of expression are obtained with constructs containing HSA minigenes with specific subsets of introns as compared with the entire HSA gene with all of its introns or with HSA cDNA.

EXAMPLE 12

GENERATION AND IDENTIFICATION OF TRANSGENIC MICE

A. Collection of Fertilized Eggs

Mice used for the collection of fertilized eggs are the inbred line FBV/N, established at the NIH (Proc. Natl. Acad. Sci. USA 88:2065–2069, 1991 ). They were obtained from the National Institute of Health Animal Genetic Resource. To induce superovulation, 5–6 week females are injected with 5 i.u. of PMSG (Intervet), followed 44–48 hours later by injection of 5 i.u. of Human Chorionic Gonadotropin (HCG) (Sigma Chemical Company). The females are then mated with mature FBV/N males. The following morning, mated females are identified by the presence of vaginal plug. The flushing of fertilized eggs from the oviduct, treatment with hyaluronidase and culture conditions in M16 or M2 media are performed as described by Hogan, Costantini and Lacy "Manipulating and Mouse embryo, A laboratory manual" Cold Spring Harbor Laboratory (1986).

B. Preparation of DNA for Microinjection

To purify DNA sequences for microinjection, plasmids carrying the BLG or BLG/HSA genes were digested with SalI, fragments separated on 1.5% agarose gels, electro-eluted and purified on elutip column (Scheicher & Schuell). DNA was suspended in 10 mM Tris pH 7.5 containing 0.5 mM EDTA at a concentration of 3 ug/ml and microinjected into the pronuclei of FBV/N eggs, which were subsequently implanted into the oviducts of CDI pseudopregnant recipient mice.

C. Microinjection

Injection pipettes are made from 10 cm long, 1.0 mm outside diameter, thin wall, borosillicate glass capillaries with filament (Cat. No. TW100F-4; World Precision Instruments, Inc. 375 Quinniplac Ave., New Haven Conn. 06513, USA). The holding pipettes are prepared from 9.0 cm long, 1.0 mm outside diameter glass capillaries (Cat. No. 105G; Drummond Scientific Co. 500 Pkwy., Broomall, Pa. 19008, USA), as described by Hogan, Costantini and Lacy "Manipulating the mouse embryo: A laboratory manual" CSHL (1986).

Microinjection is carried out in a drop of M42 medium overlaid with Silicone oil (Cat. No. 6428-R20; Thomas Scientific, P.O. Box 99, Swedesboro, N.J. 08085–0099, USA), in a glass microscope slide chamber. The chamber is mounted on the microscope (Diaphot, Nikon) equipped with ×20 and ×40 differential interferences contrast (DIC) objectives and ×10 eyepieces. 3D Hydraulic micromanipulators (Cat. No. MN-188, Nikon) are mounted on the stage of the microscope.

DNA (about 1 ul) is introduced into the injection pipette at the broad side and it is carried to the tip by capillary action along the inner filament. The injection capillary is filled up with Flurinet FC77 (Cat. No. F4758; Sigma Chemical Company) and mounted onto the micromanipulator via the instrument collar (Cat. No. 070 321; Bunton Instrument Co. Inc. Rockville, Md. 20850, USA), which is connected to the hydraulic drive unit (HDU; Bunton Instrument Co. Inc.; Rockville, Md. 20850, USA) by a tubing (PE-100; Bunton Instrument Co. Inc.; Rockville, Md. 20850, USA). The holding capillary is similarly mounted. The entire set up is filled with Flurinet FC77 (Sigma).

Batches of 20–30 pronuclear stage eggs are placed in the injection chamber. The holding and injection pipettes are brought to the chamber. While the holding pipette picks up the egg, the injection pipette is inserted into the pronucleus and about 2 pl of the DNA solution is injected. When all the eggs in the chamber are injected, they are harvested and cultured for at least 1 hour before implantation.

D. Embryo Transfer

For routine embryo transfer we use the outbred CD1 females mated with vasectomized CD1 males. Between 10–15 microinjected eggs are transferred to each oviduct, essentially as described by Hogan, Costantini and Lacy "Manipulating the mouse embryo: A laboratory manual" CSHL (1986).

E. Identification of Transgenic Mice

To purify DNA sequences for microinjection, plasmids carrying the BLG or BLG/HSA genes were digested with SalI, fragments separated on 1.5% agarose gels, electro-eluted and purified on elutip column (Scheicher & Schuell). DNA was suspended in 10 mM Tris pH 7.5 containing 0.5 mM EDTA at a concentration of 3 ug/ml and microinjected into the pronuclei of FBV/N eggs, which were subsequently implanted into the oviducts of CDI pseudopregnant recipient mice as described (25,26). Transgenic animals were identified by tail biopsies (2 cm) taken 3 weeks after birth. Biopsies were incubated in 1 ml of 50 mM Tris pH 8.0 containing 0.5% SDS, 0.1M EDTA and 200 ug proteinase K overnight at 55° C. Genomic DNA was purified from the homogenates by extraction with phenol/chloroform. Approximately 10 µg of DNA from each sample was digested with BamHI, fractionated on 0.8% agarose gel and transferred to Gene Screen filters (Du Pont). Hybridization was performed at 42° C. in 50% formamide, with probe made from the insert of plasmid p598, 32P-CTP labeled using random primed DNA labeling kit (Boehringer Mannheim). Filters were washed with 0.2× SSC containing 1% SDS at 60° C., and exposed to Kodak XAR-5 film at −80° C. (FIG. 4) Lanes are the analysis of DNA from transgenics #9 through #23 (followed by a blank (one) #25 and #26.

EXAMPLE 13

ANALYSIS OF MAMMARY GLAND EXPRESSION

A. Collection and fractionation of milk.

Milk was collected from nursing transgenic mice 10–12 days after parturition. Three hours after mothers were separated from their pups they were injected intraperitonealy with 0.3 IU oxytocin (Sigma). Milk was collected 10 min later by gentle massage of the mammary gland and taken up in a capillary tube. Milk samples were diluted 1:5 in water containing 2 mM PMSF and Aprotinin (Sigma) and defatted by centrifugation. To prepare whey, the caseins were first precipitated by addition of 1M HCl to pH 4.5. Whey proteins were subsequently precipitated in 10% trichloroacetic acid (TCA), washed with acetone and solubilized in SDS polyacrylamide gel electrophoresis (PAGE) sample buffer.

B. Milk protein analysis.

Milk proteins were analyzed for the presence of either sheep BLG or HSA. Diluted (1:5) and defatted milk collected from lactating Go or G1 females from the seven transgenic lines (transgenic strain #30, 35, 37, 38, 39, 40 and 41) were analyzed for the presence of sheep BLG by immuno-dot blot using rabbit anti-bovine BLG antibodies and iodinated protein A (FIG. 5A). The amount of material spotted on the nitrocellulose filters is indicated as well as the transgenic strain # from which the milk sample was obtained. C indicates control mouse milk. S indicates sheep milk sample. BLG indicates purified BLG protein. All seven transgenic lines expressed sheep BLG in their milk (FIG. 5A and Table 1). Expressed levels, ranging from 1.0 mg/ml (line #37) to 8.5 mg/ml (line #30)) were estimated from the intensity of the immuno-dot blot signals as compared with BLG standards and corrected for the dilution factor. As expected no signal was detected with control mouse milk which does not naturally contain BLG. In order to determine if levels of expression of BLG could be increased by increasing the length of 5'-sequences flanking the BLG transcription unit transgenic mice were produced from vectors p644 possessing approximately 5.5 kb of this region. Milk samples from two resultant transgenic lines, 46 and 48, were analyzed and found to express BLG at levels within the same range as obtained from transgenics produced from vector p585. Therefore, it appears that increasing the 5'-flanking region, containing regulatory sequences, from 3 kb (p585) to 5.5 kb (p644) did not increase levels of expression of BLG.

For the detection of BLG, whey samples were fractionated on 15% SDS polyacrylamide gels. Proteins were either stained with Coomassie blue or transferred onto nitrocellulose filter in a Bio Rad trans-blot cell (Bio Rad). Filters were blocked with TBS (20 mM TRIS/100mM NaCl) containing 2% Bovine Serum Albumin (BSA, Sigma) and subsequently reacted for 2 hours with rabbit anti-BLG antiserum (Nordic Immunological Laboratories, Capistrano Beach, Calif.). The complex was incubated with goat anti-rabbit IgG (Bio Makor, Nes Ziona Israel) and then with rabbit peroxidase anti-peroxidase (PAP, Bio Makor). Peroxidase activity was revealed using diaminobenzidine as substrate. Alternatively, sheep BLG was detected using $^{125}$I-protein A following the incubation with anti-BLG antiserum.

The whey fraction of milk obtained from the two highest expressing lines (30 and 35) were further analyzed by SDS polyacrylamide gel electrophoresis (SDS-PAGE) and immunoblot using anti-BLG antiserum. An immunoreactive band of approximately 18 kd was detected co-migrating with purified bovine BLG and native BLG in sheep milk (FIG. 5B) thus verifying the expression of authentic BLG in the milk of the transgenic lines. The amounts (μg or μl) of material loaded on the gel shown on FIG. 5B is indicated as well as the strain number from which the milk sample was obtained. C indicates control mouse milk. S indicates sheep milk sample. BLG indicates purified BLG protein. These results indicated that the basic transgenic vector with 3 kb of 5'-flanking sequences contained sufficient information to target high level expression of protein to the mammary gland of transgenic mice. A summary of results is shown in Table 2.

washings with TBS containing 0.5% tween, filters were exposed to Kodak XAR-5 film at −80° C. The initial attempt to produce transgenic mice expressing HSA in their milk was by introducing the HSA cDNA into the 5'-untranslated region of the first exon of the BLG gene of vector p585, resulting in vector p575 (FIG. 2A). The milks of lactating females from 8 transgenic lines produced from vector p575 were analyzed for the presence of HSA by immuno-dot blot using iodinated anti-HSA monoclonal antibodies. None of the 8 lines secreted detectable levels of the human protein (Table 1). It appeared that although the BLG vector was able to drive expression of its own BLG gene, it was unable to support the expression of the inserted HSA cDNA. Therefore, a series of vectors was tested in which the sheep BLG promoter was fused to HSA minigenes possessing either their first or first and second introns within their native sites of the HSA cDNA (FIG. 2A). Vector p599 differs from vector p575 only by the presence of HSA intron 1. Vector p600 also includes an HSA minigene with intron 1, but has had the BLG coding sequences deleted though it maintains the untranslated BLG exon 7 with its polyadenylation signal and site as well as BLG 3'-flanking sequences. In vector p598, with an HSA minigene containing intron 1, BLG coding sequences, exon 7 and 3'-flanking sequences were

TABLE 2

| Vector | Strain | Expression | Vector | Strain | Expression |
|---|---|---|---|---|---|
| | | EXPRESSION OF BLG | | | |
| p585 | 30 | 8.4 | p644 | 43 | UD |
| | 35 | 8.5 | | 44 | 2.1 |
| | 37 | 1.0 | | 46 | 4.2 |
| | 38 | 6.0 | | 48 | UD |
| | 39 | 8.3 | | 49 | UD |
| | 40 | 4.7 | | | |
| | 41 | 1.0 | P646 | 52 | 1.0–2.0 |
| | | | | 54 | 1.0–2.0 |
| | | | | 56 | UD |
| | | EXPRESSION OF HSA | | | |
| p575 | 1–8 | UD | p600 | 9, 11, 12, 14, 16, 17 | UD |
| p598 | 15, 18, 21, 25 | UD | p599 | 19, 20, 22, 24, 26 | UD |
| | 23 | 2.5 | | 26 | UD |
| p607 | 27, 28 | UD | p652 | 61 | 6.0 or 7.0 |
| | 31 | 0.005 | | 62 | 0.02 |
| | 34 | 0.001 | | 63, 65, 67 | Not yet determined |
| | 36 | 0.035 | | 66 | 0.04 |
| | 42 | 0.002 | | 69 | 1.5 |
| | | | | 71, 72, 73, 74 | Low level |
| | | | | 75, 77 | Not yet determined |
| p643 | 45, 47 | UD | | | |
| | | | p654 | 68, 77 | UD |
| p647 | 50, 51, 53, 55 | UD | | 76, 78, 79, 80 | Low level |
| | 57, 58, 64 | UD | | | |
| | 59 | 0.002 | p686 | 83 | Not yet determined |
| | | | p687 | 81, 82 | Not yet determined |

"Not yet determined" means that transgenic has been produced but the presence of HSA in the milk has not yet been determined.
"Low level" means that the level of HSA in the milk is between 0.01 and 0.1 mg/ml.
"UD" means undetectable.

HSA was detected in milk samples fractionated on 7.5% SDS or native polyacrylamide gels. Proteins were either stained with Coomassie blue or transferred onto nitrocellulose filters. The filters were blocked with 3% gelatin at 37° C. and then reacted overnight at room temperature with iodinated anti-HSA monoclonal antibodies. After extensive deleted and replaced with an SV40 polyadenylation signal and site. Vector p607 is similar to p600 except that it includes both HSA introns 1 and 2.

Figure 6A:
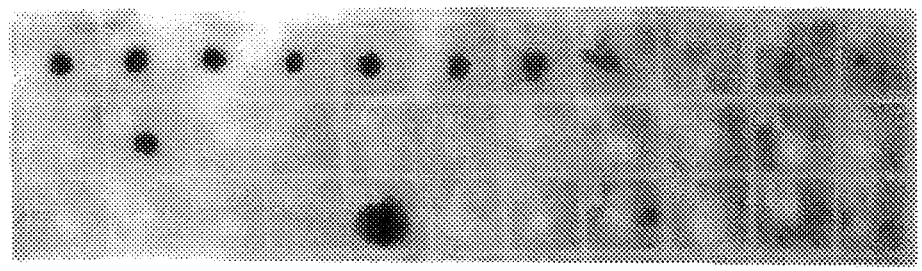
FIG. 6 demonstrates a dot blot analysis for detection (6A) and quantitation (6B) and a Western analysis (6C) of HSA expression in the milk of transgenic animals.
Figure 6B:
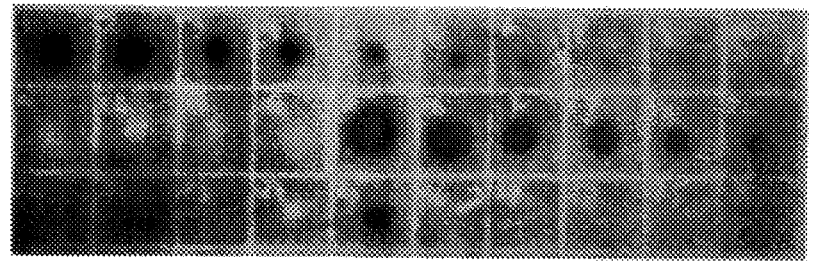

From a total of 16 individual transgenic lines produced from vectors with an HSA minigene with intron 1 (p599, p600, p598), only one (#23 from p598) expressed detectable levels of HSA in its milk (FIG. 6A and Table 1). The top row represents the spotting of the indicated amounts (ng) of commercially purified HSA (Sigma). The middle and bottom rows represent the spotting of milk samples from the indicated transgenic mouse strains, control mouse (C), human milk (H) and sheep milk(S). The milk from line 23 was estimated to contain about 2,000-3,000 ug/ml HSA as determined by comparison of its signal with HSA standards in the immuno-dot blot (FIG. 6B). The top row represents the spotting of the indicated amounts(ng) of purified HSA. The middle and bottom rows represent the spotting of indicated amounts of milk samples from indicated transgenic mouse strains, control mouse milk (C) and human milk (HM). Significantly, four of the six transgenic lines produced from vector p607, containing an HSA minigene with its first 2 introns, expressed detectable levels of HSA in their milk, ranging from 1 to 35 ug/ml (Table 1).

Similar levels of HSA expression were supported by constructs which contained the same HSA minigene whether they possessed the SV40 or BLG poly(A) site.

Figure 6C:
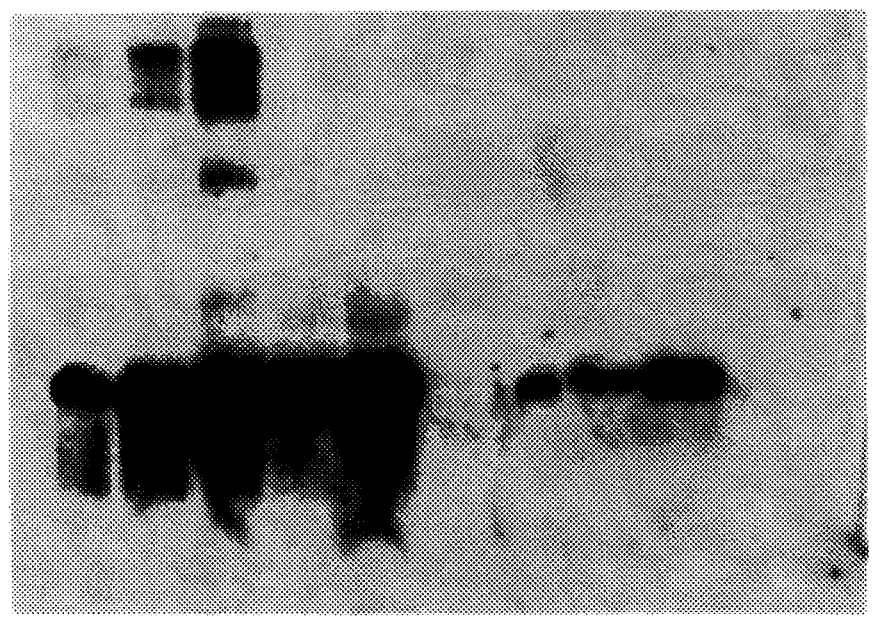
Figure 7A:
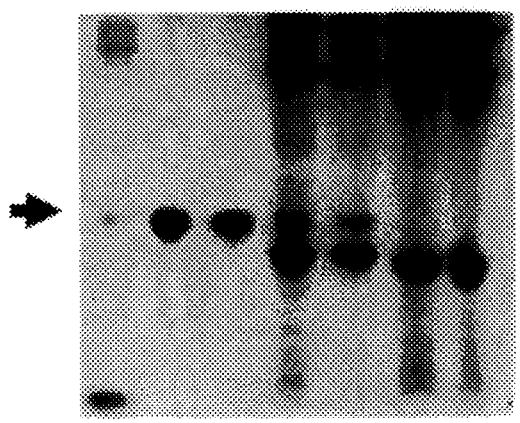
FIG. 7 demonstrates a non-denaturing gel analysis of protein in the milk of transgenic animals by coomassie stain (7A) and western analysis (7B) of HSA expression in the milk of transgenic animals.
Figure 7B:
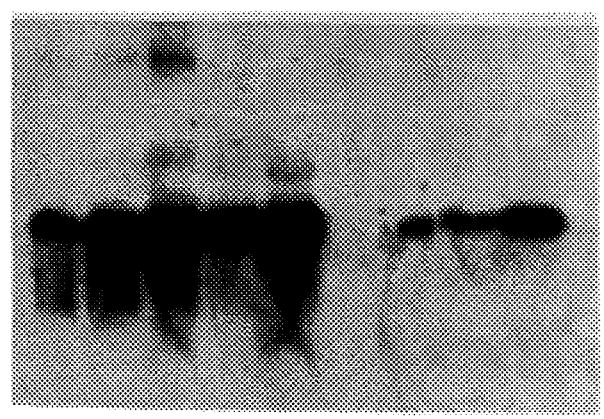

Milk samples from the 5 expressing lines, as identified by immuno-dot assay were subjected to SDS-PAGE and immunoblot (FIG. 6C). HSA represents analysis of commercial HSA. HM represents human milk. HSA 23 represents analysis of milk sample from transgenic strain #23. An immunoreactive band co-migrating with purified HSA (65 kd) was detected in the milk of all immuno-dot positive lines. Densitometry of the autorads confirmed the quantitative estimates of HSA based upon the immuno-dot blot. Mouse milk contains a significant amount of endogenous mouse serum albumin which co-migrates with human serum albumin in SDS-PAGE gels. However, as demonstrated in the immuno-detection assays (FIG. 7A and 7B), the anti-HSA monoclonal antibody specifically detected the human protein and not the mouse protein. In FIG. 7A and 7B, HM represents human milk, HSA represents commercially purified HSA (Sigma) and C represents control mouse milk. The human and mouse proteins were also distinguishable by their distinct electrophoretic mobilities on native polyacrylamide gels. Milk from expressing line 23 clearly contains both the human (low mobility) and mouse (high mobility) albumins as seen by generalized protein staining with coomassie (FIG. 7A). The lower mobility band was confirmed to be HSA by native gel and immunoblot analysis (FIG. 7B). A summary of the expression is shown in Table 2.

C. Expression of HSA RNA in different tissues of transgenic mice.

In order to examine the tissue specificity of expression of HSA RNA total RNA was isolated from various tissues of transgenic female mice on day 10–12 of lactation. Total RNA from various tissues of transgenic lactating mice was isolated by the LiCl/Urea procedure. RNA (10–15 µg) was fractionated on MOPS/formaldehyde agarose gels and blotted onto Zeta nylon filter and hybridized to a $^{32}$P-labeled anti-sense RNA probe synthesized with the RNA labeling kit (Boehringer Mannheim), according to the supplier's protocol, using HSA cDNA in pSK (Stratagene) plasmid. The HSA probe crosshybridizes to endogenous mouse serum albumin mRNA in liver.

Two patterns of HSA RNA expression were observed as represented by line 23, produced from vector p598, whose milk contains large quantities of HSA and line 19, produced from vector p599, whose milk contains no detectable HSA (FIG. 8). B represents brain; H represents heart; K represents, kidney; L represents liver; M represents mammary gland; S represents spleen; and SK represents skeletal muscle. In line 23 transcripts of the transgene were clearly detected in the mammary gland and to a lesser extent in skeletal muscle. No detectable signal was found in the other tissues examined, even after a long exposure of the autoradiogram. The HSA transgene RNA migrated slightly slower than the endogenous mouse serum albumin mRNA (2070 ribonucleotides). This is consistent with an expected transgenic mRNA size of about 2230 ribonucleotides composed of the untranslated portion of BLG exon 1 from its cap site to the site of introduction of the HSA minigene, the HSA transcription unit itself minus introns 1 sequences removed by splicing, and SV40 sequences upstream of its polyadenylation site.

In mouse line 19, as well as six of the transgenic lines carrying vector p575 (all of whose milk contains no HSA), transgene transcripts were not detected in the mammary gland. However, significant levels of transcripts were found in the kidney. Their higher mobility than the endogenous mouse albumin mRNA indicates an RNA smaller than the size expected (2783 ribonucleotides) of a polycistronic mRNA composed of both HSA and BLG sequences as would be produced from vectors p599 and p575. Endogenous mouse serum albumin mRNA was also detected in the kidney of control mice.

D. In situ hybridization

In situ hybridization was performed on paraffin sections of mammary glands of virgin and lactating transgenics and control mice as described in Sassoon, D., Lyons, G., Wright, W., Lin, V., Lassar, A., Weintraub, H. and Buckingham, M. 1989. Expression of two myogenic regulatory factors myogenin and MyoD1 during mouse embryogenesis. Nature 341:303–307. The probe used was $^{35}$S-UTP labeled antisense RNA synthesized from the HSA cDNA with T7 polymerase. (FIG. 9) The top panels show virgin ducts of control mammary gland. The bottom panels show virgin ducts of transgenic strain #23 mammary gland. The right side shows detection of HSA probe under bright field illumination. On the left side are dark field micrographs of the same samples.

E. Explant studies

Figure 10:
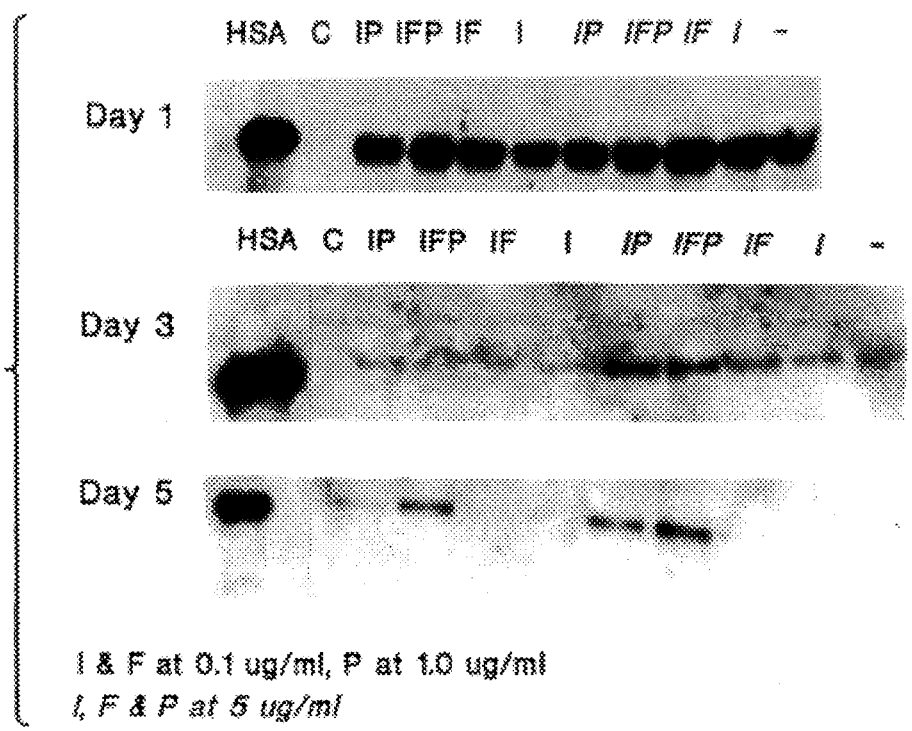
FIG. 10 demonstrates a Western analysis of HSA expression by mammary explants of transgenic animals.

Explant cultures of mammary glands of virgin and lactating mice were performed as described by Pittius, C. W., Sankaran, L., Topper, Y. J., and Hennighausen, L. 1988. Mol. Endocrinol 2:1027–1032. Briefly, after mincing, pieces of approximately 1 mm were cultivated on lens paper floats in serum free M199 medium. For hormonal stimulation, bovine insulin (0.1 or.5 ug/ml), hydrocortisone (0.1 or 5 ug/ml) and ovine prolactin (1 or 5 ug/ml) were added to the medium. All hormones were purchased form Sigma (ST. Louis, Mo.). The medium was collected for several days, and then screened for the presence of HSA or other milk proteins. (FIG. 10) HSA represents commercially purified HSA signal. C represents control mouse explants. I represents insulin; P represents prolactin; F represents hydrocortisone. First set IP, IFP, IF, I) represent treatments with the lower concentrations of hormones. Second set represent treatments with the higher concentration of hormones.

EXAMPLE 14

PRODUCTION OF TRANSGENIC GOATS

A. Induction of Superovulation

Embryos were recovered from Saanen goat does that have been induced to superovulate by treating them for 12 days with intravaginal sponges impregnated with 30 mg of fluorogestone acetate (Chrono-Gest, Intervet International B. V.-Boxmeer-Holland). From the evening of the 9th day after sponge insertion, 5 intramuscular injections of follicle stimulating hormone (FSH-P, Schering Corp.) were administered every 12 hours (5, 4, 3, 3 and 2 mg FSH-P). On the evening of the 11th day when the last FSH injection was administered the sponges were withdrawn. Does were checked for estrus every 4 to 12 hours, beginning 12 hours after sponge removal. They were mated by 2 bucks at 20 and 36 hours after sponge withdrawal. One to two cell eggs were collected about 62 hours after sponge removal. The recipients are similarly synchronized with intravaginal sponges. On the evening of the 11th day sponges are removed and the recipient does are injected with 500 units of PMSG (Intervet).

B. Surgery

Does were taken off food (36 hours) and water (12 hours) prior to surgery. Anaesthesia is induced by intravenous injection of thiopentone sodium and maintained by mixtures of oxygen (1–2 liters/min) and halothane (1–2%) (Halocarbon Laboratories, N. Augusta, S.C.). The reproductive tract is exposed through mid-central incision and a glass catheter inserted into the oviduct through the fimbria. Five ml PBS containing 5% FCS were introduced into the uterine lumen through a blunted 18-gauge needle and forced through the uterotubal junction and along the oviduct.

C. Microinjection

DNA (1–4 ug/ml) is injected into one pronucleus of 1 or 2 cell eggs placed in a chamber filled with ovum culture medium (Flow Labs, Irving, Scotland) containing 20% FCS and covered with Flurinet 70 (Sigma). Pronuclei are visualized using the Nikon Diaphet Inverted microscope equipped with Nomarski optics at ×400. Eggs are microinjected essentially as described by Hogan et al. (Manipulating the mouse embryo- a laboratory manual, Cold Spring Harbor Laboratory, 1986). Surviving embryos were surgically transferred to the oviduct of recipient does using the Socorex 1–5 ul micropipette. Up to 10 embryos are transferred to each recipient.

Deposit of Strains Useful in Practicing the Invention

Deposits of biologically pure cultures of the following strains were made under the Budapest Treaty with the American Type Culture Collection, 12301 Parklawn Drive, Rockville, Md., The accession numbers indicated were assigned after successful viability testing, and the requisite fees were paid.

Access to said cultures will be available during pendency of the patent application to one determined by the Commissioner of the United States Patent and Trademark Office to be entitled thereto under 37 C.F.R. §1.14 and 35 U.S.C. §122, or if and when such access is required by the Budapest Treaty. All restriction on availability of said cultures to the public will be irrevocably removed upon the granting of a patent based upon the application and said cultures will remain permanently available for a term of at least five years after the most recent request for the furnishing of samples and in any case for a period of at least 30 years after the date of the deposits. Should the cultures become nonviable or be inadvertently destroyed, they will be replaced with viable cultures(s) of the same taxonomic description.

| Strain/Plasmid | ATCC No. | Deposit Date |
| --- | --- | --- |
| p652.2 | 68653 | July 25, 1991 |
| p696.9 | 68654 | July 25, 1991 | p652.2 is an isolate of *E. coli* containing the plasmid p652, and p696.9 is an isolate of *E. coli* containing the plasmid p696.

One skilled in the art will readily appreciate the present invention is well adapted to carry out the objects and obtain the ends and advantages mentioned, as well as those inherent therein. The peptides, antibodies, methods, procedures and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

What is claimed as new and is desired to be covered under Letters Patent is:

1. A DNA construct adapted for the expression of human serum albumin in mammalian cells that do not normally express human serum albumin, comprising a promoter from a mammalian gene and a sequence coding for human serum albumin,
   (a) wherein the human serum albumin sequence comprises at least one, but not all, of the introns in the naturally occurring gene encoding the HSA protein;
   (b) wherein said introns are selected to provide for expression of HSA in said mammalian cells at levels equal to or greater than levels resulting from the expression of the naturally occurring HSA gene in said mammalian cells; and
   (c) wherein said naturally occurring HSA gene encodes the HSA protein and includes exons and introns in their native positional relationships.

2. The construct of claim 1 wherein said mammalian gene is a milk protein gene.

3. The genetic construct of claim 1 wherein said introns are selected from the group consisting of 1–6, 7–14, 1+7–14, 1+2+12–14, 2+7–14 and 1+2+7–14.

4. A DNA construct encoding HSA adapted for the expression of human serum albumin in mammalian cells that do not normally express human serum albumin, comprising one but not all of the first 7 introns of the HSA gene, and one of the last 7 introns of the HSA gene,
   (a) wherein said introns are selected to provide for expression of HSA in said mammalian cells at levels equal to or greater than the naturally occurring HSA gene in said mammalian cells; and
   (b) wherein said naturally occurring HSA gene encodes the HSA protein and includes exons and introns in their native positional relationships.

5. A DNA construct according to claim 1 comprising DNA sequences encoding human serum albumin operably linked to a mammary tissue specific promoter, said DNA construct expressed by the mammary glands of a lactating female transgenic mammal.

6. A DNA construct adapted for the expression of human serum albumin in mammalian cells that do not normally express human serum albumin comprising a sequence coding for human serum albumin and a promoter from a mammalian gene, said mammalian gene not encoding human serum albumin,
   (a) wherein the human serum albumin sequence comprises at least one, but not all, of the introns in the naturally occurring gene encoding the HSA protein,
   (b) wherein said introns are selected to provide for expression of HSA in said mammalian cells at levels equal to or greater than levels resulting from the expression of the naturally occurring HSA gene in said mammalian cells; and
   (c) wherein said naturally occurring HSA gene encodes the HSA protein and includes exons and introns in their native positional relationships.

7. A DNA construct comprising a promoter from a mammalian gene, and a sequence coding for human serum albumin,
   wherein the human serum albumin sequence contains an intron complement which is selected to provide expression of HSA in mammalian cells at levels greater than the levels of expression provided by a construct containing said promoter and the entire HSA gene with all 14 of its introns, in said mammalian cells.

8. A method of making human serum albumin in a mammalian cell that does not normally express human serum albumin comprising introducing the DNA construct of claim 1 into the mammalian cell, wherein human serum albumin is expressed in said mammalian cell at levels equal to or greater than levels resulting from the expression of the naturally occurring HSA gene in said mammalian cell.

9. The method of claim 8, further comprising the step of purifying the expressed human serum albumin.

10. A method of making human serum albumin in a mammalian cell that does not normally express human serum albumin comprising introducing the DNA construct of claim 2 into the mammalian cell, wherein human serum albumin is expressed in said mammalian cell at levels equal to or greater than levels resulting from the expression of the naturally occurring HSA gene in said mammalian cell.

11. The method of claim 10, further comprising the step of purifying the expressed human serum albumin.

12. A method of making human serum albumin in a mammalian cell that does not normally express human serum albumin comprising introducing the DNA construct of claim 3 into the mammalian cell, wherein human serum albumin is expressed in said mammalian cell at levels equal to or greater than levels resulting from the expression of the naturally occurring HSA gene in said mammalian cell.

13. The method of claim 12, further comprising the step of purifying the expressed human serum albumin.

14. A method of making human serum albumin in a mammalian cell that does not normally express human serum albumin comprising introducing the DNA construct of claim 7 into the mammalian cell, wherein human serum albumin is expressed in said mammalian cell at levels equal to or greater than levels resulting from the expression of the naturally occurring HSA gene in said mammalian cell.

15. The method of claim 14, further comprising the step of purifying the expressed human serum albumin.

16. A method of making human serum albumin in a mammalian cell that does not normally express human serum albumin comprising introducing the DNA construct of claim 5 into the mammalian cell, wherein human serum albumin is expressed in said mammalian cell at levels equal to or greater than levels resulting from the expression of the naturally occurring HSA gene in said mammalian cell.

17. The method of claim 16, further comprising the step of purifying the expressed human serum albumin.

18. A method of making human serum albumin in a mammalian cell that does not normally express human serum albumin comprising introducing the DNA construct of claim 6 into the mammalian cell, wherein human serum albumin is expressed in said mammalian cell at levels equal to or greater than levels resulting from the expression of the naturally occurring HSA gene in said mammalian cell.

19. The method of claim 18, further comprising the step of purifying the expressed human serum albumin.

\* \* \* \* \*